(12) United States Patent
Walter et al.

(10) Patent No.: US 8,486,986 B2
(45) Date of Patent: Jul. 16, 2013

(54) MICROBIOCIDES

(75) Inventors: Harald Walter, Stein (CH); Daniel Stierli, Stein (CH); Hans Tobler, Basel (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 466 days.

(21) Appl. No.: 12/664,415

(22) PCT Filed: Jun. 13, 2008

(86) PCT No.: PCT/EP2008/004789
§ 371 (c)(1),
(2), (4) Date: Dec. 14, 2009

(87) PCT Pub. No.: WO2008/151828
PCT Pub. Date: Dec. 18, 2008

(65) Prior Publication Data
US 2010/0222389 A1 Sep. 2, 2010

(30) Foreign Application Priority Data

Jun. 15, 2007 (EP) ..................................... 07011797
Mar. 11, 2008 (EP) ..................................... 08004438

(51) Int. Cl.
*A01N 43/56* (2006.01)
*C07D 409/12* (2006.01)

(52) U.S. Cl.
USPC .......................... 514/407; 514/406; 548/365.7

(58) Field of Classification Search
USPC ................................ 548/365.7; 514/406, 407
See application file for complete search history.

(56) References Cited

FOREIGN PATENT DOCUMENTS

| | | |
|---|---|---|
| EP | 1710237 | 10/2006 |
| WO | 2006108791 | 10/2006 |
| WO | 2007006739 | 1/2007 |

*Primary Examiner* — Patricia L Morris
(74) *Attorney, Agent, or Firm* — R. Kody Jones

(57) ABSTRACT

Compounds of the formula (I), in which the substituents are as defined in claim 1 are suitable for use as microbiocides.

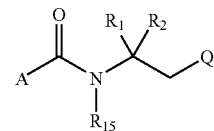

(I)

11 Claims, No Drawings

MICROBIOCIDES

This application is a 371 of International Application No. PCT/EP2008/004789 filed Jun. 13, 2008, which claims priority to EP 07011797.3 filed Jun. 15, 2007, and EP 08004438.1 filed Mar. 11, 2008, the contents of which are incorporated herein by reference.

The present invention relates to novel microbiocidally active, in particular fungicidally active, thienyl/benzthienyl ethyl amides. It further relates to intermediates used in the preparation of these compounds, to compositions which comprise these compounds and to their use in agriculture or horticulture for controlling or preventing infestation of plants by phytopathogenic microorganisms, preferably fungi.

Thienyl ethyl amides and their use as fungicides are described in WO 2006/108791 and EP-1710237A1. Benzthienyl ethyl amides and their use as fungicides are described in WO 2007/006739.

It has been found that novel thienyl/benzthienyl ethyl amides have microbiocidal activity. The present invention thus provides compounds of the formula I

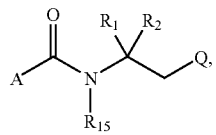
(I)

wherein

A is a 5- or 6-membered heterocyclic ring containing one to three heteroatoms, each independently selected from oxygen, nitrogen and sulphur, or a phenyl ring; the heterocyclic ring or the phenyl being substituted by the groups $R_6$, $R_7$ and $R_8$;

$R_6$, $R_7$ and $R_8$ are each, independently, hydrogen, halogen, cyano, nitro, $C_{1-4}$ alkyl, $C_{1-4}$ halogenalkyl, $C_{1-4}$ halogenalkoxy, $C_{1-4}$ alkoxy($C_{1-4}$)alkyl or $C_1$ halogenalkoxy ($C_{1-4}$)alkyl, provided that at least one of $R_6$, $R_7$ and $R_8$ is not hydrogen;

$R_1$ and $R_2$ independently of each other stand for hydrogen, halogen, $C_1$-$C_4$ alkyl or $C_1$-$C_4$ halogenalkyl;

Q is $Q_1$

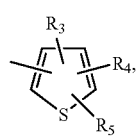
($Q_1$)

or Q is $Q_2$

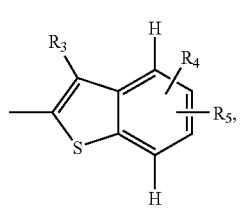
($Q_2$)

wherein
$R_3$ is halogen or $C_1$-$C_4$ halogenalkyl;
$R_4$ is $C_3$-$C_7$ cycloalkyl acetynyl, phenyl acetynyl, halogenphenyl acetynyl or halogenphenyl;
$R_5$ is hydrogen, halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl;
$R_{15}$ is hydrogen or $C_3$-$C_7$ cycloalkyl;
and tautomers/isomers/enantiomers of these compounds.

According to the invention, the term "acetynyl", as used in the definition of substituents $R_4$ and $R_5$, stands for the group "—C≡C—". As example, $C_3$ cycloalkyl acetynyl stands for the group

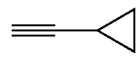

and is present, for example, as substituent $R_4$ in compound 1.1.

The alkyl groups occurring in the definitions of the substituents can be straight-chain or branched and are, for example, methyl, ethyl, n-propyl, n-butyl, n-pentyl, n-hexyl, iso-propyl, n-butyl, sec-butyl, iso-butyl or tert-butyl. Alkoxy, alkenyl and alkynyl radicals are derived from the alkyl radicals mentioned. The alkenyl and alkynyl groups can be mono- or di-unsaturated.

The cycloalkyl groups occurring in the definitions of the substituents are, for example, cyclopropyl, cyclobutyl, cyclopentyl, cyclohexyl or cycloheptyl.

Halogen is generally fluorine, chlorine, bromine or iodine, preferably fluorine, bromine or chlorine. This also applies, correspondingly, to halogen in combination with other meanings, such as halogenalkyl or halogenalkoxy.

Halogenalkyl groups preferably have a chain length of from 1 to 4 carbon atoms. Halogenalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy is, for example, methoxy, ethoxy, propoxy, i-propoxy, n-butoxy, isobutoxy, sec-butoxy and tert-butoxy; preferably methoxy and ethoxy. Halogenalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Halogenphenyl is preferably phenyl substituted by 1, 2 or 3 halogen atoms, for example 4-chloro-phenyl.

In the context of the present invention a "5- or 6-membered heterocyclic ring containing one to three heteroatoms, each independently selected from oxygen, nitrogen and sulphur" preferably means pyrazolyl (especially pyrazol-4-yl), thiazolyl (especially thiazol-5-yl), pyrrolyl (especially pyrrol-3-yl), 1,2,3 triazolyl, oxazolyl (especially oxazol-5-yl), pyridyl (especially pyrid-3-yl) or 2,3 dihydro-[1,4]oxathiinyl (especially 2,3 dihydro-[1,4]oxathiin-5-yl).

The compounds of formula I, wherein $R_{15}$ is hydrogen, can occur in different isomeric forms; the invention covers all those isomers and mixtures thereof. The compounds of the formula I may occur in different tautomeric forms. For example, compounds of formula I exist in the tautomeric forms $I_I$ and $I_{II}$:

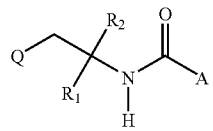

$I_I$

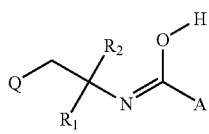

$I_{II}$

The invention covers all those tautomeric forms and mixtures thereof.

Preferably $R_{15}$ is hydrogen. In a preferred group of compounds A is a 5-membered heterocyclic ring containing one to three heteroatoms, each independently selected from oxygen, nitrogen and sulphur; the heterocyclic ring being substituted by the groups $R_6$, $R_7$ and $R_8$.

Within said preferred group of compounds, further preferably A is $A_1$

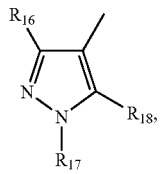

(A₁)

in which $R_{16}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;

$R_{17}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and $R_{18}$ is hydrogen, halogen or cyano;

or A is $A_2$

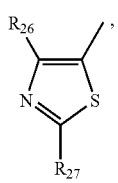

(A₂)

in which $R_{26}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and $R_{27}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;

or A is $A_3$

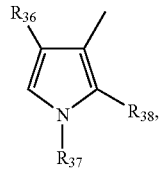

(A₃)

in which $R_{36}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;

$R_{37}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and $R_{38}$ is hydrogen, halogen or cyano;

or A is $A_4$

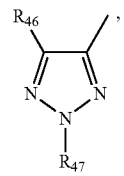

(A₄)

in which $R_{46}$ and $R_{47}$ independently of one another are halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl.

Within said preferred group of compounds, further preferably A is $A_1$.

Within said preferred group of compounds, further preferably A is $A_2$.

Within said preferred group of compounds, further preferably A is $A_3$.

Within said preferred group of compounds, further preferably A is $A_4$.

In another preferred group of compounds A is a phenyl ring or a 6-membered heterocyclic ring containing one to three heteroatoms, each independently selected from oxygen, nitrogen and sulphur; the phenyl ring or the heterocyclic ring being substituted by the groups $R_6$, $R_7$ and $R_8$.

Within said preferred group of compounds, further preferably A is $A_5$

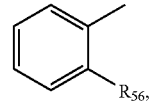

(A₅)

in which $R_{56}$ is halogen, $C_1$-$C_4$halogenalkyl, $C_1$-$C_4$halogenalkoxy, or $C_1$-$C_4$halogenalkoxy-$C_1$-$C_4$alkyl;

or A is $A_6$

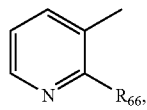

(A$_6$)

in which $R_{66}$ is halogen, cyano, nitro, $C_1$-$C_4$alkyl, $C_1$-$C_4$halogenalkyl, $C_1$-$C_4$alkoxy-$C_1$-$C_4$alkyl or $C_1$-$C_4$halogenalkoxy-$C_1$-$C_4$alkyl;

or A is $A_7$

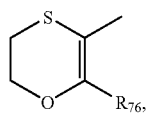

(A$_7$)

in which $R_{76}$ is $C_1$-$C_4$alkyl or $C_1$-$C_4$halogenalkyl.

Within said preferred group of compounds, further preferably A is $A_5$.

Within said preferred group of compounds, further preferably A is $A_6$.

Within said preferred group of compounds, further preferably A is $A_7$.

In a particular preferred group of compounds A is $A_1$, wherein $R_{18}$ is hydrogen. In another particular preferred group of compounds A is $A_1$, wherein $R_{16}$ is $C_1$-$C_4$alkyl or $C_1$-$C_4$halogenalkyl, preferably $C_1$-$C_4$halogenalkyl; $R_{17}$ is $C_1$-$C_4$alkyl; and $R_{18}$ is hydrogen or halogen, preferably hydrogen.

In another particular preferred group of compounds A is $A_2$, wherein $R_{26}$ is $C_1$-$C_4$alkyl or $C_1$-$C_4$halogenalkyl; and $R_{27}$ is $C_1$-$C_4$alkyl.

In yet another particular preferred group of compounds A is $A_3$, wherein $R_{36}$ is $C_1$-$C_4$alkyl or $C_1$-$C_4$halogenalkyl; $R_{37}$ is $C_1$-$C_4$alkyl; and $R_{38}$ is hydrogen or halogen.

In yet another particular preferred group of compounds A is $A_4$, wherein $R_{46}$ is $C_1$-$C_4$alkyl or $C_1$-$C_4$halogenalkyl; and $R_{47}$ is $C_1$-$C_4$alkyl.

In yet another particular preferred group of compounds A is $A_4$, wherein $R_{46}$ halogenmethyl, preferably $R_{46}$ is selected from $CF_3$, $CF_2H$ and $CFH_2$; and $R_{47}$ is $C_1$-$C_4$alkyl.

In yet another particular preferred group of compounds A is $A_5$, wherein $R_{56}$ is halogen or $C_1$-$C_4$halogenalkyl.

In yet another particular preferred group of compounds A is $A_6$, wherein $R_{66}$ is halogen or $C_1$-$C_4$halogenalkyl.

In yet another particular preferred group of compounds A is $A_7$, wherein $R_{76}$ is $C_1$-$C_4$alkyl or $C_1$-$C_4$halogenalkyl.

In a preferred group of compounds $R_1$ is hydrogen or methyl. In one embodiment, $R_1$ is hydrogen. In one embodiment, $R_1$ is methyl.

In a preferred group of compounds $R_2$ is hydrogen.

In one embodiment Q is $Q_1$.

In one embodiment $Q_1$ is $Q_{1A}$.

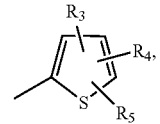

(Q$_{1A}$)

wherein $R_3$, $R_4$ and $R_4$ are as defined under formula I.

Preferably, $Q_{1A}$ is $Q_{1A\text{-}1}$

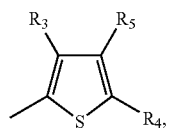

(Q$_{1A\text{-}1}$)

wherein $R_3$, $R_4$ and $R_4$ are as defined under formula I. In yet more preferred compounds within this embodiment, $R_3$ is halogen, more preferably chloro or bromo; $R_4$ is $C_3$-$C_7$ cycloalkyl acetynyl, phenyl acetynyl, halogenphenyl acetynyl or halogenphenyl; and $R_5$ hydrogen. These compounds are shown in tables 1 to 6.

In one embodiment $Q_1$ is $Q_{1B}$

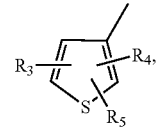

(Q$_{1B}$)

wherein $R_3$, $R_4$ and $R_4$ are as defined under formula I.

Preferably, $Q_{1B}$ is $Q_{1B\text{-}1}$

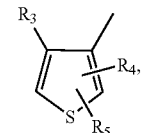

(Q$_{1B\text{-}1}$)

wherein $R_3$, $R_4$ and $R_4$ are as defined under formula I.

Preferably, $Q_{1B}$ is $Q_{1B\text{-}2}$

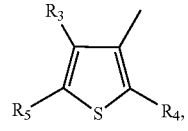

(Q$_{1B\text{-}2}$)

wherein $R_3$, $R_4$ and $R_4$ are as defined under formula I. In yet more preferred compounds within this embodiment, $R_3$ is halogen, more preferably chloro; $R_4$ is $C_3$-$C_7$ cycloalkyl acetynyl, phenyl acetynyl, halogenphenyl acetynyl or halogenphenyl; and $R_5$ is halogen, even more preferably chloro.

These compounds are shown in tables 7 to 12.

Further preferably, $Q_{1B}$ is $Q_{1B\text{-}3}$

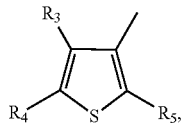

(Q$_{1B\text{-}3}$)

wherein $R_3$, $R_4$ and $R_4$ are as defined under formula I. In yet more preferred compounds within this embodiment, $R_3$ is halogen, more preferably chloro; $R_4$ is $C_3$-$C_7$ cycloalkyl acetynyl, phenyl acetynyl, halogenphenyl acetynyl or halogenphenyl; and $R_5$ is halogen, even more preferably chloro. These compounds are also shown in tables 7 to 12.

In one embodiment Q is $Q_2$. This embodiment is represented by compounds of tables 13 and 14.

$R_3$ is preferably halogen, more preferably chloro or bromo.

In a preferred group of compounds $R_4$ is $C_3$-$C_7$ cycloalkyl acetynyl, phenyl acetynyl or halogenphenyl acetynyl.

In another preferred group of compounds $R_4$ is $C_3$-$C_7$ cycloalkyl acetynyl.

In another preferred group of compounds $R_4$ is halogenphenyl acetynyl, more preferably 4-halogen-phenyl.

In yet another preferred group of compounds $R_4$ is halogenphenyl, more preferably 4-halogen-phenyl.

$R_5$ is preferably hydrogen or halogen.

In one embodiment, $R_5$ is hydrogen.

In another embodiment $R_5$ is halogen, preferably chloro.

Compounds of formula I, wherein Q is $Q_{1A}$ and $R_2$, $R_5$ and $R_{15}$ are hydrogen may be prepared according to scheme 1.

Scheme 1:

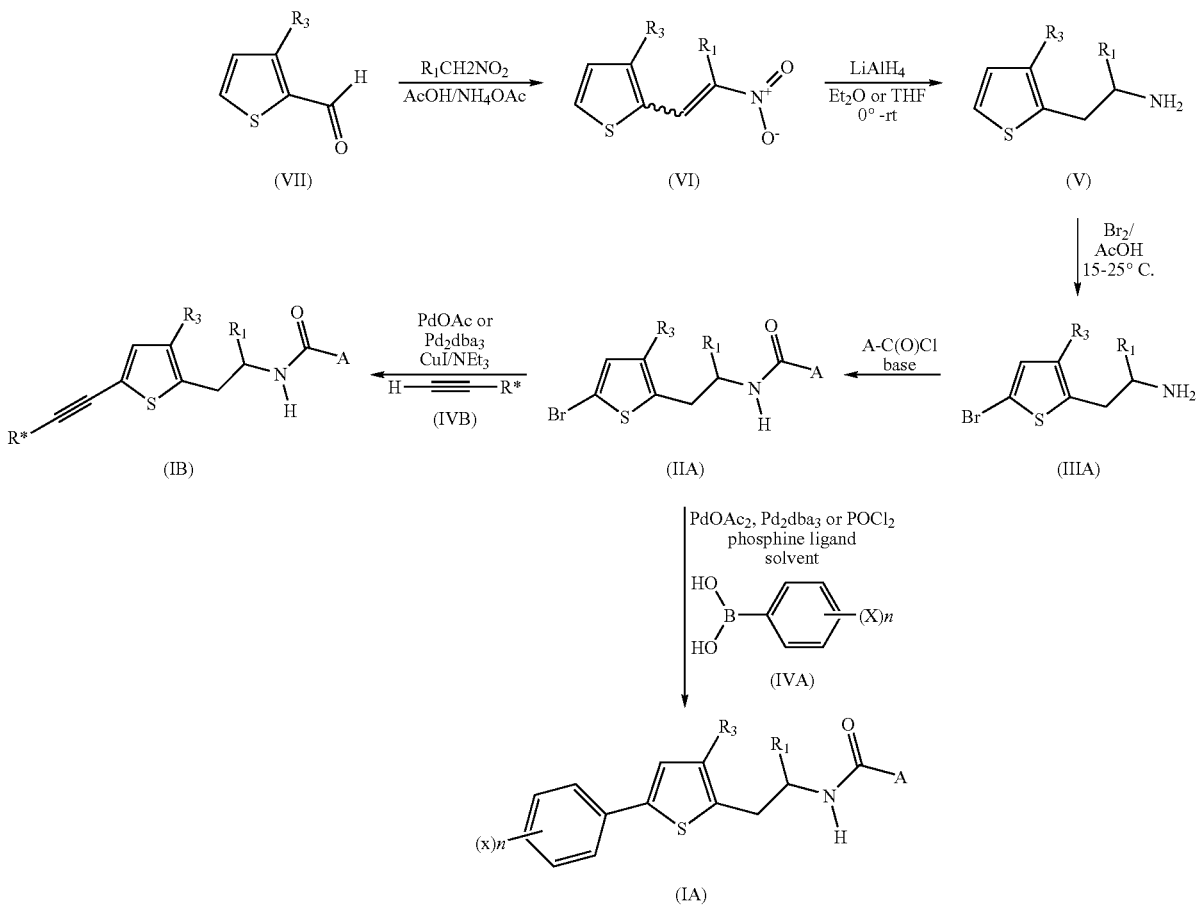

A thiophene-2-aldehyde of formula VII, wherein $R_3$ is as defined under formula I can be reacted with a nitroalkane of the formula $R_1CH_2NO_2$, wherein $R_1$ is as defined under formula I to form the nitroalkenes of formula VI, in which $R_1$ and $R_3$ are as defined under formula I. Said reaction is carried out conveniently in the presence of acetic acid and ammonium acetate at temperatures between ambient temperature and reflux temperature.

The nitroalkenes of formula VI can be reduced to the amines of formula V, wherein $R_1$ and $R_3$ are as defined under formula I, by using LiAlH$_4$ in an ether solvent, such as diethylether or tetrahydrofurane.

Subsequently the amines of formula V can be brominated, for example with bromine in the presence of acetic acid, to the amines of formula IIIA, wherein $R_1$ and $R_3$ are as defined under formula I.

The brominated amines of formula IIIA can then be amidated by using the corresponding acid derivatives, such as acid chlorides of the formula A-C(O)Cl, wherein A is as defined under formula I, to form the brominated amides of formula IIA, wherein A, wherein $R_1$ and $R_3$ are as defined under formula I. Said amidations are conveniently carried out in the presence of a base, such as triethylamine, Hunig base, sodium bicarbonate, sodium carbonate, potassium carbonate, pyridine or quinoline, but preferably triethylamine, and in a solvent, such as diethylether, TBME, THF, dichloromethane, chloroform, DMF or NMP, for between 10 minutes and 48 hours, preferably 12 to 24 hours, and between 0° C. and reflux, preferably 20 to 25° C.

Compounds of the formula IA may be prepared by reacting the brominated amine of formula IIA with a compound of formula VIA, wherein X is halogen and n is 1, 2, 3, 4 or 5, preferably 1, using the well known Suzuki coupling methodology. The Suzuki reaction has also become one of the standard methods for the direct coupling of two aromatic ring systems and is described, for example, in Journal of the American Chemical Society 121(41), 9550 (1999) and in Journal für Praktische Chemie 342(4), 334-339 (2000).

Compounds of the formula IB may be prepared by reacting the brominated amine of formula IIA with an acetynyl compound of the formula IVB, wherein R* is $C_3$-$C_7$ cycloalkyl, phenyl or halogenphenyl using the well known Sonogashira coupling methodology. The Sonogashira reaction has become one of the standard methods for introducing an alkynyl function into unsaturated and aromatic or heteroaromatic molecules. It is reviewed, for example, in the *Handbook of Organopalladium Chemistry for Organic Synthesis* Vol. 1, 767-789 (2002); by I. B. Campbell in *Organocopper reagents* (IRL-Press, 1994); by K. C. Nicolaou et. al. in *Angewandte Chemie Int. Ed.*, 44, 4442 (2005); by R. Tykwinski et. al., ibid. 42, 1433 (2002); and by A. Zapf et. al. in *Topics in Catalysis*, 19, 101 (2002).

Compounds of formula I, wherein Q is $Q_{1B}$, $R_2$ is hydrogen and $R_5$ is chloro may be prepared according to scheme 2.

Scheme 2:

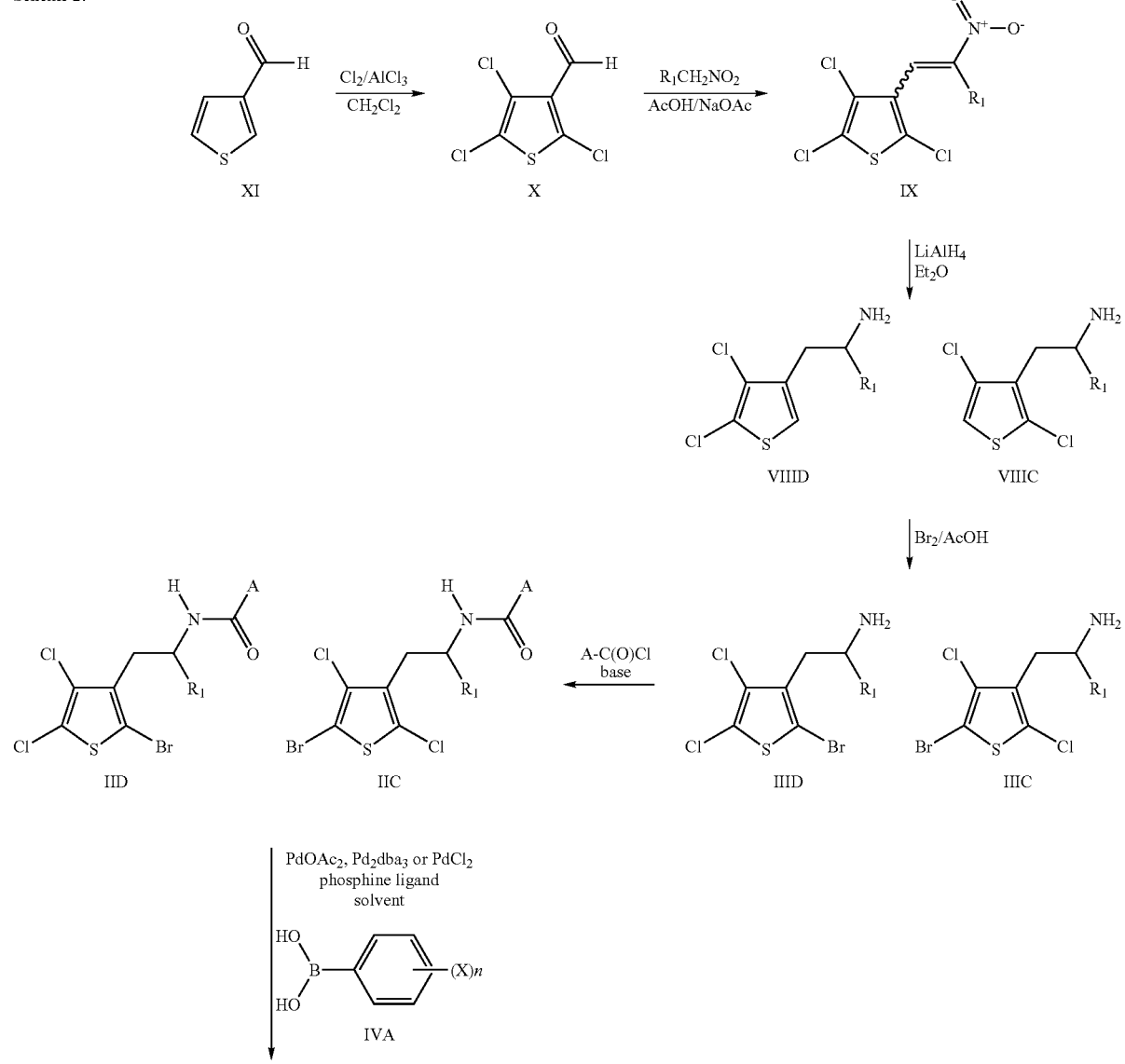

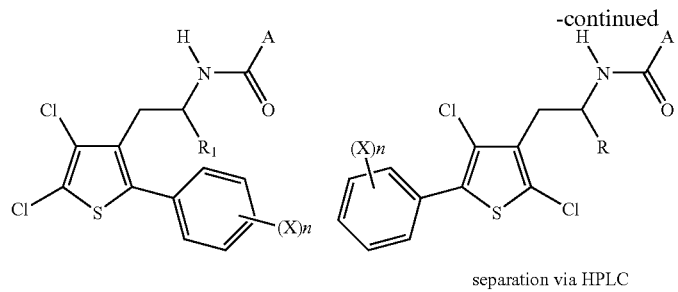

ID    IC separation via HPLC

Thiophene-3-aldehyde (compound of formula XI) can be exhaustively chlorinated with $Cl_2/AlCl_3$ according to known methods to generate the tri-chlorinated thiophene aldehyde of formula X.

The compound of formula X can be reacted with a nitroalkane of the formula $R_1CH_2NO_2$, wherein $R_1$ is as defined under formula I to form the nitroalkene of formula IX, in which $R_1$ is as defined under formula I. The nitroalkenes of formula IX can be reduced to the di-chlorinated amines of formulae VIIIC and VIIID, wherein $R_1$ is as defined under formula I. Subsequently the amines of formulae VIIIC and VIIID can be brominated to form the amines of formulae IIIC and IIID, wherein $R_1$ is as defined under formula I.

The brominated amines of formulae IIIC and IIID can then be amidated by using the corresponding acid derivatives, such as acid chlorides of the formula A-C(O)Cl, wherein A is as defined under formula I, to form the brominated amides of formulae IIC and IID, wherein A, wherein $R_1$ and $R_3$ are as defined under formula I.

Compounds of the formulae IC and ID may be prepared by reacting the brominated amines of formulae IIC and IID with a compound of formula VIA, wherein X is halogen and n is 1, 2, 3, 4 or 5, preferably 1, via the Suzuki reaction.

Suitable reaction conditions for the formation of the compounds of formulae VIIIC, VIIID, IIIC, IIID, IIIC, IIID, IC and ID are as described for scheme 1 above.

Compounds of formula IE and IF

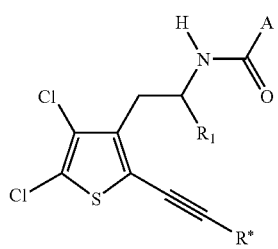

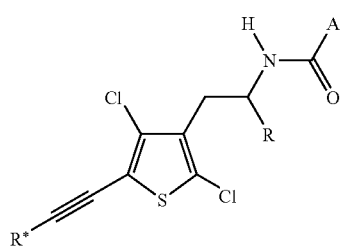

wherein A and $R_1$ are as defined under formula I and R* is $C_3$-$C_7$ cycloalkyl, phenyl or halogenphenyl, can be formed from compounds of formula IIC and IID via the Sonogashira reaction as described for scheme 1 above.

Compounds of formula I, wherein Q is $Q_2$, $R_2$ is hydrogen and $R_3$ is chloro may be prepared according to scheme 3.

Scheme 3:

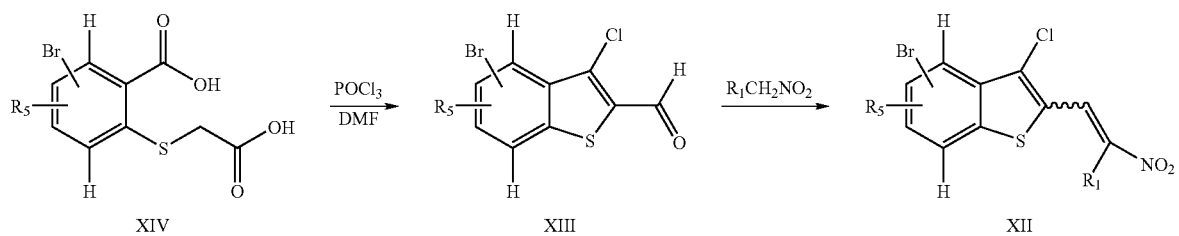

XIV    XIII    XII

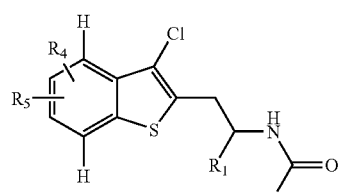 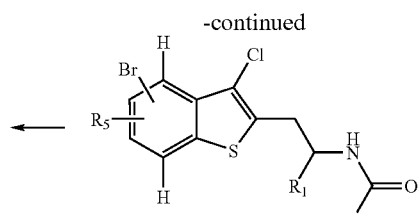 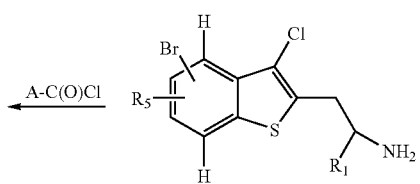

IG                                        IIG                                        IIIG

Benzthiophenes of formula XIII, wherein $R_5$ is as defined under formula I, can be prepared from compounds of formula XIV, wherein $R_5$ is as defined under formula I, as described in J. Org. Chem. 1996, 61(9), 6523-25.

Starting from the benzthiophenes of formula XIII, the compounds of formulae XII, IIIG and IIIG, wherein A, $R_1$ and $R_5$ are as defined under formula I, can be prepared as described above for scheme 1.

Compounds of formula IG may be prepared by reacting the brominated amide of formula IIG with a compound of formula VIA or VIB as described above for scheme 1 via the Suzuki reaction or Sonogashira reaction.

The compounds of the formulae VII, IVA, IVB, XI and XIV, wherein the substituents as described above, and the nitroalkanes of formula $R_1CH_2NO_2$, wherein $R_1$ is as defined under formula I, are known and commercially available or can be prepared according to the above-mentioned references or according to methods known in the art.

Compounds of the formula A-C(O)Cl are known and partially commercially available. They can be prepared analogously as described, for example, in WO 00/09482, WO 02/38542, WO 04/018438, EP-0-589-301, WO 93/11117 and Arch. Pharm. Res. 2000, 23(4), 315-323.

Compounds of formula I, wherein $R_{15}$ is $C_3$-$C_7$cycloalkyl can be, for example, prepared according to the following reaction scheme:

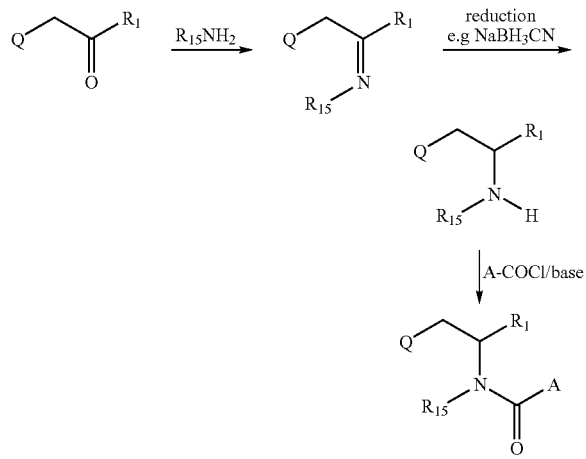

For preparing all further compounds of the formula I functionalized according to the definitions of A, Q, $R_1$ and $R_2$, there are a large number of suitable known standard methods, such as alkylation, halogenation, acylation, amidation, oximation, oxidation and reduction. The choice of the preparation methods which are suitable are depending on the properties (reactivity) of the substituents in the intermediates.

The reactions to give compounds of the formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at room temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

The compounds of formula I can be isolated in the customary manner by concentrating and/or by evaporating the solvent and purified by recrystallization or trituration of the solid residue in solvents in which they are not readily soluble, such as ethers, aromatic hydrocarbons or chlorinated hydrocarbons.

The compounds I and, where appropriate, the tautomers thereof, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

The compounds I and, where appropriate, the tautomers thereof, can, if appropriate, also be obtained in the form of hydrates and/or include other solvents, for example those which may have been used for the crystallization of compounds which are present in solid form.

It has now been found that the compounds of formula I according to the invention have, for practical purposes, a very advantageous spectrum of activities for protecting useful plants against diseases that are caused by phytopathogenic microorganisms, such as fungi, bacteria or viruses.

The invention relates to a method of controlling or preventing infestation of useful plants by phytopathogenic microorganisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus). Good activity has been observed against Asian soybean rust (*Phakopsora pachyrhizi*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as active ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as active ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

Surprisingly, it has now been found that the compounds of formula I can also be used in methods of protecting crops of useful plants against attack by phytopathogenic organisms as well as the treatment of crops of useful plants infested by phytopathogenic organisms comprising administering a combination of glyphosate and at least one compound of formula I to the plant or locus thereof, wherein the plant is resistant or sensitive to glyphosate.

Said methods may provide unexpectedly improved control of diseases compared to using the compounds of formula I in the absence of glyphosate. Said methods may be effective at enhancing the control of disease by compounds of formula I. While the mixture of glyphosate and at least one compound of formula I may increase the disease spectrum controlled, at least in part, by the compound of formula I, an increase in the activity of the compound of formula I on disease species already known to be controlled to some degree by the compound of formula I can also be the effect observed.

Said methods are particularly effective against the phytopathogenic organisms of the kingdom Fungi, phylum Basidiomycot, class Uredinomycetes, subclass Urediniomycetidae and the order Uredinales (commonly referred to as rusts). Species of rusts having a particularly large impact on agriculture include those of the family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal crops and *Puccinia recondita*, also known as brown rust.

An embodiment of said method is a method of protecting crops of useful plants against attack by a phytopathogenic organism and/or the treatment of crops of useful plants infested by a phytopathogenic organism, said method comprising simultaneously applying glyphosate, including salts or esters thereof, and at least one compound of formula I, which has activity against the phytopathogenic organism to at least one member selected from the group consisting of the plant, a part of the plant and the locus of the plant.

The compounds of formula (I), or a pharmaceutical salt thereof, described above may also an advantageous spectrum of activity for the treatment and/or prevention of microbial infection in an animal.

"Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula (I) in the manufacture of a medicament for use in the treatment and/or prevention of microbial infection in an animal. There is also provided the use of a compound of formula (I) as a pharmaceutical agent. There is also provided the use of a compound of formula (I) as an antimicrobial agent in the treatment of an animal. According to the present invention there is also provided a pharmaceutical composition comprising as an active ingredient a compound of formula (I), or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula (I) may be effective against various microbial species able to cause a microbial infection in an animal. Examples of such microbial species are those causing Aspergillosis such as *Aspergillus fumigatus, A. flavus, A. terrus, A. nidulans* and *A. niger*, those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia colymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in greater detail without limiting it.

PREPARATION EXAMPLES

Example P1

Preparation of 3-difluoromethyl-1-methyl-1H-pyrazole-4-carboxylic acid[2-(3-chloro-5-cyclopropylethinylthiophen-2-yl)-1-methylethyl]amide (Compound 1.26)

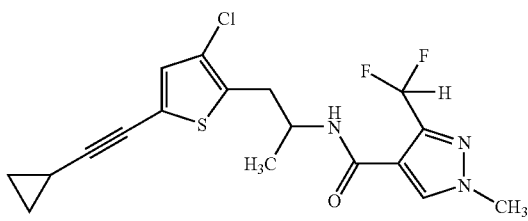 [SMILES: CC(Cc1sc(C#CC2CC2)cc1Cl)NC(=O)c1cn(C)nc1C(F)F]

In a sulfonation flask a mixture containing of 240 mg (0.58 mmol) 3-difluoromethyl-1-methyl-1H-pyrazole-4-carboxylic acid[2-(5-bromo-3-chlorothiophen-2-yl)-1-methylethyl] amide, 80 mg (1.15 mmol) cyclopropyacetylene, 10 mg copper(I)iodide, 36 mg (0.05 mmol) bistriphenylphosphine palladium dichloride and 30 ml triethylamine is stirred at 60° C. for 2 days. Then another 80 mg of cyclopropylacetylene is added and stirring continued for 24 hours. After cooling to ambient temperature ethylacetate and water is added and the organic layer separated and washed again twice with water. After drying (sodium sulphate) and distilling off the solvent in a water jet vacuum, the crude product is obtained. Purification is achieved by column chromatography over silicagel (eluent: ethylacetate/heptane 1:1). Yield: 90 mg (23% of theory) of a slightly brown resin ($^1$H-NMR: 0.8/m/2H, 0.9/m/2H, 1.22/d/3H, 1.45/m/1H, 3.01/d/2H, 3.9/s/3H, 4.40/m/1H, 6.28/s (broad)/1H, 6.88/t/1H—CF$_2$H, 6.89/s/1H, 7.85/s/1H).

Example P2

Preparation of 3-difluoromethyl-1-methyl-1H-pyrazole-4-carboxylic acid{2-[3-chloro-5-(4-fluorophenyl)thiophen-2-yl]-1-methylethyl}amide (Compound 1.46)

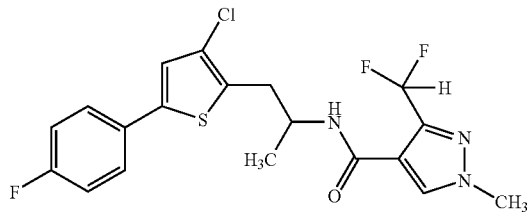 [SMILES: CC(Cc1sc(-c2ccc(F)cc2)cc1Cl)NC(=O)c1cn(C)nc1C(F)F]

In a sulfonation flask a mixture containing of 207 mg (0.5 mmol) 3-difluoromethyl-1-methyl-1H-pyrazole-4-carboxylic acid[2-(5-bromo-3-chlorothiophen-2-yl)-1-methylethyl] amide, 90 mg (0.64 mmol) 4-fluorophenylboronic acid, 151 mg (1.8 mmol) sodiumbicarbonate, 36 mg (0.05 mmol) bistriphenylphosphine palladium dichloride, 10 ml dimethoxyethane and 5 ml of water is stirred at reflux for 6 hours. After cooling to ambient temperature ethylacetate and water is added and the organic layer separated and washed again twice with water. After drying (sodium sulphate) and distilling off the solvent in a water jet vacuum, the crude product is obtained. Purification is achieved by column chroma-tography over silicagel (eluent: ethylacetate/heptane 1:1). Yield: 180 mg (80% of theory) of a slightly brown oil (1H-NMR: 1.29/d/3H, 0.9/m/2H, 3.09/m/2H, 3.89/s/3H, 4.42/m/1H, 6.38/s (broad)/1H, 6.89/t/1H—CF$_2$H, 7.05/m/2H, 7.48/m/2H, 7.89/s/1H).

Example P3

Preparation of 1-methyl-3-trifluoromethyl-1H-pyrazole-4-carboxylic acid {2-[2,4-dichloro-5-(4-fluorophenyl)-thiophen-3-yl]-1-methylethyl}amide (Compound 7.70) and 1-methyl-3-trifluoromethyl-1H-pyrazole-4-carboxylic acid {2-[4,5-dichloro-2-(4-fluorophenyl)-thiophen 3-yl]1-methylethyl}amide (Compound 7.72)

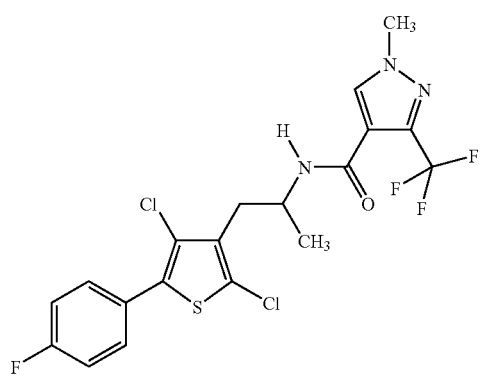

-continued

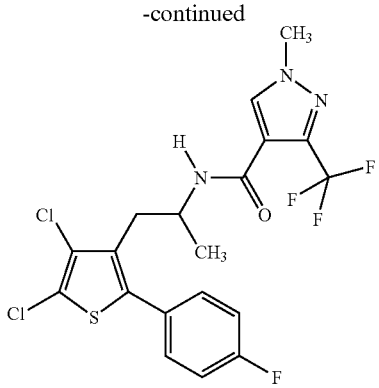

In a sulfonation flask 280 mg (0.6 mmol) of the isomeric amide mixture obtained in example P5c) is dissolved in 10 ml of 1,2-dimethoxyethane. After addition of 105 mg (0.75 mmol) 4-fluorophenylboronic acid, 35 mg (0.05 mmol) bis (triphenylphosphine)palladium dichloride and 225 mg (2.7 mmol) sodium bicarbonate dissolved in 5 ml water, the resulting mixture is stirred for 3 hours at 70-75° C. After cooling 100 ml of water is added and the mixture extracted 3 times with ethylacetate. The organic layer is washed with brine and after drying (sodium sulphate) and evaporation of the solvent the crude isomer mixture is obtained. A first purification is achieved by column chromatography over silicagel (eluent: ethylacetate/heptane 1:1). The isolation of the two fluorophenyl-isomers is achieved by HPLC (high pressure liquid chromatography). Regioisomer I (compound 7.70) is obtained in pure form as a colourless oil ($^1$H-NMR: 1.31/d/3H, 2.9/m/2H(diastereotopic protons), 3.97/s/3H, 4.55/m/1H, 5.98/d (broad)/1H, 7.12/t/2H, 7.53/m/2H, 7.87/s/1H). Regioisomer 2 (compound 7.72) could also be obtained in pure form (84 mg=29% of theory) in the form of white crystals (m.p.: 127-130° C.).

Example P4

Preparation of 3-difluoromethyl-1-methyl-1H-pyrazole-4-carboxylic acid[2-(5-bromo-3-chlorothiophen-2-yl)-1-methylethyl]amide (Compound Z1.2)

a) Preparation of 3-chloro-2-((E)-nitropropenyl)thiophene

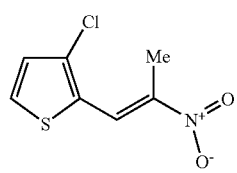 [SMILES: C/C(=C\c1sccc1Cl)[N+](=O)[O-]]

In a sulfonation flask, a mixture containing 11.7 g (0.08 mol) 3-chlorothiophene-2-carbaldehyde, 48 g (0.64 mol) nitroethane, 15.4 g (0.2 mol) ammoniumacetate and 160 ml acetic acid is heated at 90° C. for 5 hours. After cooling ethylacetate is added and the organic phase washed three times with water. The organic phase is dried over sodium sulphate and after filtration the organic solvent is distilled off in a water jet vacuum. The residue is purified by column chromatography over silicagel (eluent: ethylacetate/heptane 1:5). Yield: 10.8 g (67% of theory) of a colourless oil ($^1$H-NMR: 2.57/s/3H, 7.12/d/1H, 7.62/d/1H, 8.45/s/1H).

b) Preparation of 2-(3-chlorothiophen-2-yl)-1-methylethylamine

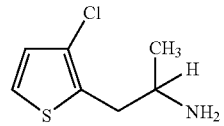

In a sulfonation flask 5.4 g (0.0265 mol) 3-chloro-2-((E)-nitropropenyl)thiophene is added to 120 ml a 1 molar etheral solution of LiAlH$_4$ (0.12 mol) in such a manner that the internal temperature remains constant at 0-5° C. The mixture is then stirred for 4 hours at 20° C. After quenching at 5° C. with the minimum amount of water, sodium sulphate is added. After filtration and distilling off the solvent in a water jet vacuum a solution, the crude material is obtained. Purification is achieved by column chromatography over silicagel (eluent: tert. butylmethylether/EtOH 3:1). Yield: 34.6 g (74% of theoery) of a colourless oil ($^1$H-NMR: 1.18/d/3H, 1.42/s/NH$_2$, 2.72-2.9/m (diasterotopic protons)/2H, 3.25/m/1H, 6.89/d/1H, 7.16/d/1H).

c) Preparation of 2-(5-bromo-3-chlorothiophen-2-yl)-1-methylethylamine (compound Z2.2)

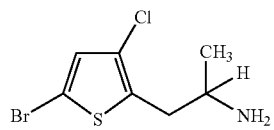

In a sulfonation flask 5 g (0.028 mol) 2-(3-chlorothiphen-2-yl)-1-methylethylamine is dissolved in 70 ml of acetic acid. The mixture is then cooled to 15° C. and 4.8 g (0.30 m) of bromine is added under stirring (internal temperature 15-17° C.). After warming up to rt, the mixture is stirred for 16 hours. Then the mixture is poured to a mixture of tert. butylmethylether (ca. 250 ml) and 2N sodiumhydroxide. The final pH is 11. After washing with brine, drying with sodium sulphate and evaporation of the solvent the crude material is obtained. Purification is achieved by column chromatography over silicagel (eluent: tert. butylmethylether/EtOH 10:1). Yield: 5.4 g (75% of theory) of a colourless oil ($^1$H-NMR: 1.18/d/3H, 2.68-2.87/m (diasterotopic protons)/2H, 3.2/m/1H, 6.87/s/1H).

d) Preparation of 3-difluoromethyl-1-methyl-1H-pyrazole-4-carboxylic acid[2-(5-bromo-3-chlorothiophen-2-yl)-1-methylethyl]amide (compound Z1.2)

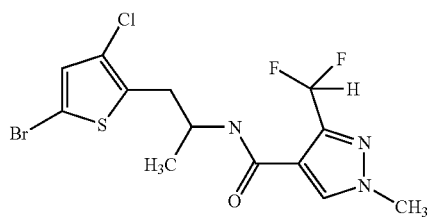 [SMILES: CC(Cc1sc(Br)cc1Cl)NC(=O)c1cn(C)nc1C(F)F]

In a sulfonation flask 1 g (4 mmol) of the amine prepared in example 3 and 1 ml (6 mmol) triethylamine are dissolved in 30 ml of methylenechloride. Then a mixture of 780 mg (4 mmol) 3-difluoromethyl-1-methyl-1-H-pyrazole 4-carboxylic acid chloride and 10 ml methylenechloride is added at room temperature under stirring. After stirring for 16 hours the solvent is evaporated in a water jet vacuum and the residue purified by column chromatography over silicagel (eluent: ethylacetate/hexane 1:1). Yield: 1.65 g (83% of theory) of white crystals. M.p. 157-158° C.

Example P5

Preparation of 3-difluoromethyl-1-methyl-1H-pyrazole-4-carboxylic acid[2-(5-bromo-3-chlorothiophen-2-yl)-1-methylethyl]amide (Compound Z1.2)

a) Preparation of 2-(4,5-dichlorothiophen-3-yl)-1-methylethylamine and 2-(2,4-dichlorothiophen-3-yl)-1-methylethylamine

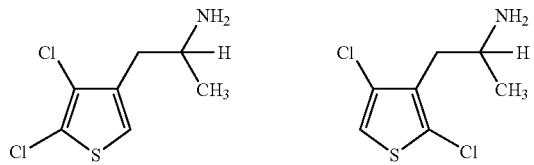

In a sulfonation flask 10 ml (10 mmol) of a 1 molar ethereal LiAlH$_4$ solution is slowly added to 30 ml of tetrahydrofurane. Then a solution of 0.9 g (3.32 mmol) 2,3,5-trichloro-4-((E)-2-nitropropenyl)thiophene is added slowly in such a manner that the internal temperature remains constant between 10-12° C. Stirring continued for 3 hours at 10-12° C. Then the mixture is quenched with 0.4 ml of water and 0.38 g sodium-hydroxide solution (15%). After addition of 5 ml saturated ammoniumchloride solution the suspension is filtered. The liquid layer is dried and then the solvent is distilled off in a water jet vacuum. The raw material is purified by column chromatography over silicagel (eluent: tert.butylmethylether/ethanol 20:1—1:1). The obtained mixture of amines (0.4 g) contains 27% of 2-(4,5-dichlorothiophen-3-yl)-1-methylethylamine, 30% of 2-(2,4-dichlorothiophen-3-yl)-1-methylethylamine and 43% of the undesired trichloro-compound 2-(2,4,5-trichlorothiophen-3-yl)-1-methylethylamine.

b) Preparation of 2-(2-bromo-4,5-dichlorothiophen-3-yl)-1-methyl-ethylamine and 2-(5-bromo-2,4-dichlorothiophen-3-yl)-1-methylethylamine

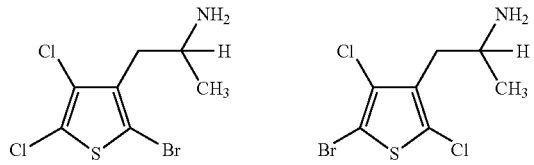

In a sulfonation flask 2.49 g (11.9 mmol) of the isomer mix obtained in example P5a) is dissolved in 25 ml of acetic acid. Then 1.99 g (12.4 mmol) of bromine is added dropwise during 5 minutes. Stirring continued for 16 hours at room temperature and then the acid is evaporated in a water jet vacuum. The solid residue was poured into 50 ml of saturated sodium-hydrocarbonate solution and then the water phase is extracted 3 times with ter.butylmethylether. After drying (sodium sulphate) and distilling off the solvent in a water jet vacuum the crude material is obtained. Purification is achieved by column chromatography over silicagel (eluent: tert.butylmethylether/ethanol 20:1-1:1). 2.1 g of a brown oil consisting of an isomer mixture of 27% 2-(2-bromo-4,5-dichlorothiophen-3-yl)-1-methyl-ethylamine, 27% 2-(5-bromo-2,4-dichlorothiophen-3-yl)-1-methylethylamine and 43% of the undesired 2-(2,4,5-trichlorothiophen-3-yl)-1-methylethylamine.

c) Preparation of 1-methyl-3-trifluoromethyl-1H-pyrazole-4-carboxylic acid [2-(2-bromo-4,5-dichlorothiophen-3-yl)-1-methylethyl]amide and 1-methyl-3-trifluoromethyl-1H-pyrazole-4-carboxylic acid [2-(5-bromo-2,4-dichlorothiophen-3-yl)-1-methylethyl]amide

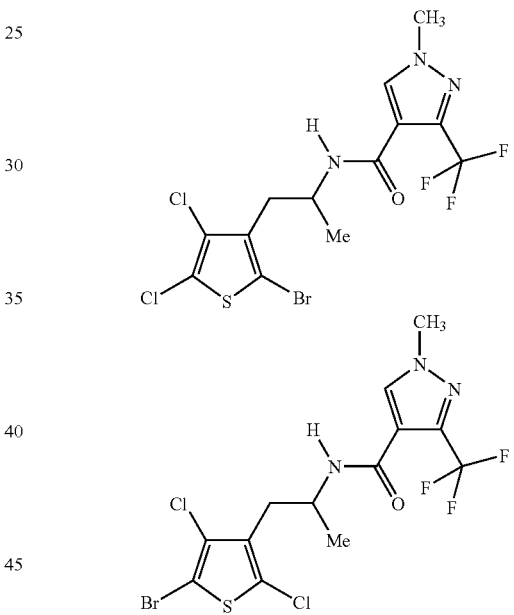

In a sulfonation flask 2.07 g (7.2 mmol) of the amine isomer mixture prepared in example P5b) and 1.45 g (14.4 mmol) triethylamine are dissolved in 50 ml of methylenechloride. Then a mixture of 1.65 g (7.2 mmol) 3-trifluoromethyl-1-methyl-1-H-pyrazole 4-carboxylic acid chloride and 50 ml methylenechloride is added at room temperature under stirring. After stirring for 16 hours the solvent is evaporated in a water jet vacuum and the residue purified by column chromatography over silicagel (eluent: ethylacetate/heptane 1:2-2:1). 1.52 g of an isomeric mixture of amides is obtained in the form of slightly brown crystals (m.p.: 134-138° C.). The mixture consists of 27% of 1-methyl-3-trifluoromethyl-1H-pyrazole-4-carboxylic acid [2-(2-bromo-4,5-dichlorothiophen-3-yl)-1-methylethyl]amide, 30% of 1-methyl-3-trifluoromethyl-1H-pyrazole-4-carboxylic acid [2-(5-bromo-2,4-dichlorothiophen-3-yl)-1-methylethyl]amide and 43% of the undesired 1-methyl-3-trifluoromethyl-1H-pyrazole-4-carboxylic acid [2-(2,4,5-trichlorothiophen-3-yl)-1-methylethyl]amide.

Tables 1 to 14: Compounds of Formula I

The invention is further illustrated by the preferred individual compounds of formula (I) listed below in Tables 1 to 14. Characterising data is given in Table 21.

TABLE 1

Compounds of formula Ia

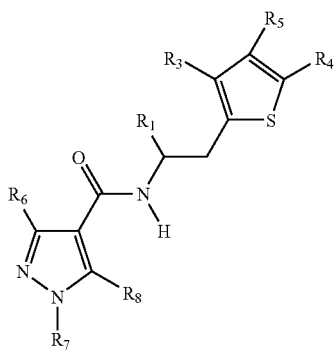

(Ia)

| Compound Number | $R_1$ | $R_3$ | $R_4$ | $R_5$ | $R_6$ | $R_7$ | $R_8$ |
|---|---|---|---|---|---|---|---|
| 1.1 | H | Cl | ethynyl-cyclopropyl | H | Me | Me | F |
| 1.2 | Me | Cl | ethynyl-cyclopropyl | H | Me | Me | F |
| 1.3 | H | Br | ethynyl-cyclopropyl | H | Me | Me | F |
| 1.4 | Me | Br | ethynyl-cyclopropyl | H | Me | Me | F |
| 1.5 | H | Cl | ethynyl-cyclopentyl | H | Me | Me | F |
| 1.6 | Me | Cl | ethynyl-cyclopentyl | H | Me | Me | F |
| 1.7 | H | Br | ethynyl-cyclopentyl | H | Me | Me | F |
| 1.8 | Me | Br | ethynyl-cyclopentyl | H | Me | Me | F |
| 1.9 | H | Cl | ethynyl-cyclohexyl | H | Me | Me | F |
| 1.10 | Me | Cl | ethynyl-cyclohexyl | H | Me | Me | F |
| 1.11 | H | Br | ethynyl-cyclohexyl | H | Me | Me | F |
| 1.12 | Me | Br | ethynyl-cyclohexyl | H | Me | Me | F |
| 1.13 | H | Cl | ethynyl-phenyl | H | Me | Me | F |
| 1.14 | Me | Cl | ethynyl-phenyl | H | Me | Me | F |
| 1.15 | H | Br | ethynyl-phenyl | H | Me | Me | F |
| 1.16 | Me | Br | ethynyl-phenyl | H | Me | Me | F |
| 1.17 | H | Cl | 4-Cl-phenyl | H | Me | Me | F |
| 1.18 | Me | Cl | 4-Cl-phenyl | H | Me | Me | F |
| 1.19 | H | Br | 4-Cl-phenyl | H | Me | Me | F |
| 1.20 | Me | Br | 4-Cl-phenyl | H | Me | Me | F |
| 1.21 | H | Cl | 4-F-phenyl | H | Me | Me | F |
| 1.22 | Me | Cl | 4-F-phenyl | H | Me | Me | F |

TABLE 1-continued

Compounds of formula Ia

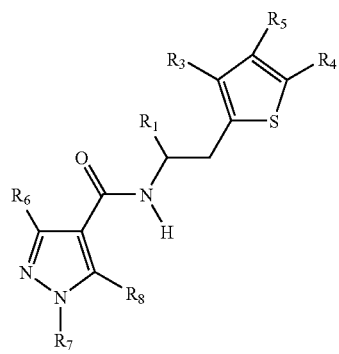

(Ia)

| Compound Number | R₁ | R₃ | R₄ | R₅ | R₆ | R₇ | R₈ |
|---|---|---|---|---|---|---|---|
| 1.23 | H | Br | ![4-F-phenyl] | H | Me | Me | F |
| 1.24 | Me | Br | ![4-F-phenyl] | H | Me | Me | F |
| 1.25 | H | Cl | ![ethynyl-cyclopropyl] | H | $CF_2H$ | Me | H |
| 1.26 | Me | Cl | ![ethynyl-cyclopropyl] | H | $CF_2H$ | Me | H |
| 1.27 | H | Br | ![ethynyl-cyclopropyl] | H | $CF_2H$ | Me | H |
| 1.28 | Me | Br | ![ethynyl-cyclopropyl] | H | $CF_2H$ | Me | H |
| 1.29 | H | Cl | ![ethynyl-cyclopentyl] | H | $CF_2H$ | Me | H |
| 1.30 | Me | Cl | ![ethynyl-cyclopentyl] | H | $CF_2H$ | Me | H |
| 1.31 | H | Br | ![ethynyl-cyclopentyl] | H | $CF_2H$ | Me | H |
| 1.32 | Me | Br | ![ethynyl-cyclopentyl] | H | $CF_2H$ | Me | H |
| 1.33 | H | Cl | ![ethynyl-cyclohexyl] | H | $CF_2H$ | Me | H |
| 1.34 | Me | Cl | ![ethynyl-cyclohexyl] | H | $CF_2H$ | Me | H |

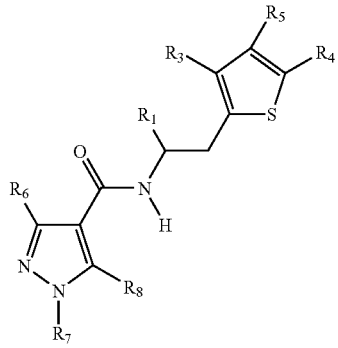

(Ia)

| Compound Number | R₁ | R₃ | R₄ | R₅ | R₆ | R₇ | R₈ |
|---|---|---|---|---|---|---|---|
| 1.35 | H | Br | ![ethynyl-cyclohexyl] | H | $CF_2H$ | Me | H |
| 1.36 | Me | Br | ![ethynyl-cyclohexyl] | H | $CF_2H$ | Me | H |
| 1.37 | H | Cl | ![ethynyl-phenyl] | H | $CF_2H$ | Me | H |
| 1.38 | Me | Cl | ![ethynyl-phenyl] | H | $CF_2H$ | Me | H |
| 1.39 | H | Br | ![ethynyl-phenyl] | H | $CF_2H$ | Me | H |
| 1.40 | Me | Br | ![ethynyl-phenyl] | H | $CF_2H$ | Me | H |
| 1.41 | H | Cl | ![4-Cl-phenyl] | H | $CF_2H$ | Me | H |
| 1.42 | Me | Cl | ![4-Cl-phenyl] | H | $CF_2H$ | Me | H |
| 1.43 | H | Br | ![4-Cl-phenyl] | H | $CF_2H$ | Me | H |
| 1.44 | Me | Br | ![4-Cl-phenyl] | H | $CF_2H$ | Me | H |
| 1.45 | H | Cl | ![4-F-phenyl] | H | $CF_2H$ | Me | H |

TABLE 1-continued

Compounds of formula Ia

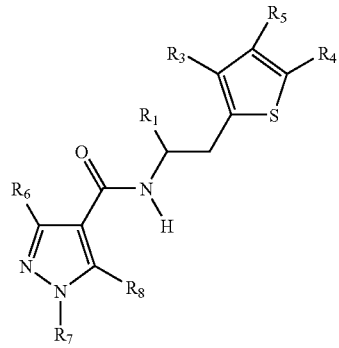
(Ia)

| Compound Number | $R_1$ | $R_3$ | $R_4$ | $R_5$ | $R_6$ | $R_7$ | $R_8$ |
|---|---|---|---|---|---|---|---|
| 1.46 | Me | Cl | 4-F-phenyl | H | $CF_2H$ | Me | H |
| 1.47 | H | Br | 4-F-phenyl | H | $CF_2H$ | Me | H |
| 1.48 | Me | Br | 4-F-phenyl | H | $CF_2H$ | Me | H |
| 1.49 | H | Cl | cyclopropylethynyl | H | $CF_3$ | Me | H |
| 1.50 | Me | Cl | cyclopropylethynyl | H | $CF_3$ | Me | H |
| 1.51 | H | Br | cyclopropylethynyl | H | $CF_3$ | Me | H |
| 1.52 | Me | Br | cyclopropylethynyl | H | $CF_3$ | Me | H |
| 1.53 | H | Cl | cyclopentylethynyl | H | $CF_3$ | Me | H |
| 1.54 | Me | Cl | cyclopentylethynyl | H | $CF_3$ | Me | H |
| 1.55 | H | Br | cyclopentylethynyl | H | $CF_3$ | Me | H |
| 1.56 | Me | Br | cyclopentylethynyl | H | $CF_3$ | Me | H |
| 1.57 | H | Cl | cyclohexylethynyl | H | $CF_3$ | Me | H |

TABLE 1-continued

Compounds of formula Ia

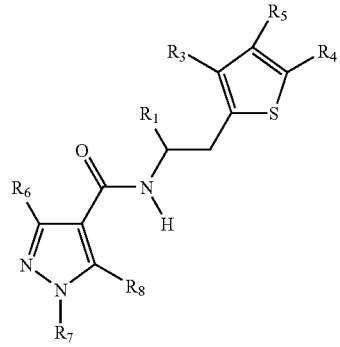
(Ia)

| Compound Number | $R_1$ | $R_3$ | $R_4$ | $R_5$ | $R_6$ | $R_7$ | $R_8$ |
|---|---|---|---|---|---|---|---|
| 1.58 | Me | Cl | cyclohexylethynyl | H | $CF_3$ | Me | H |
| 1.59 | H | Br | cyclohexylethynyl | H | $CF_3$ | Me | H |
| 1.60 | Me | Br | cyclohexylethynyl | H | $CF_3$ | Me | H |
| 1.61 | H | Cl | phenylethynyl | H | $CF_3$ | Me | H |
| 1.62 | Me | Cl | phenylethynyl | H | $CF_3$ | Me | H |
| 1.63 | H | Br | phenylethynyl | H | $CF_3$ | Me | H |
| 1.64 | Me | Br | phenylethynyl | H | $CF_3$ | Me | H |
| 1.65 | H | Cl | 4-Cl-phenyl | H | $CF_3$ | Me | H |
| 1.66 | Me | Cl | 4-Cl-phenyl | H | $CF_3$ | Me | H |
| 1.67 | H | Br | 4-Cl-phenyl | H | $CF_3$ | Me | H |
| 1.68 | Me | Br | 4-Cl-phenyl | H | $CF_3$ | Me | H |

TABLE 1-continued

Compounds of formula Ia

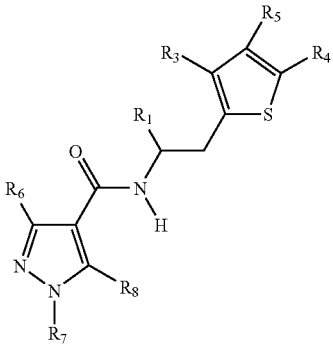

(Ia)

| Compound Number | R₁ | R₃ | R₄ | R₅ | R₆ | R₇ | R₈ |
|---|---|---|---|---|---|---|---|
| 1.69 | H | Cl | 4-F-phenyl | H | CF₃ | Me | H |
| 1.70 | Me | Cl | 4-F-phenyl | H | CF₃ | Me | H |
| 1.71 | H | Br | 4-F-phenyl | H | CF₃ | Me | H |
| 1.72 | Me | Br | 4-F-phenyl | H | CF₃ | Me | H |

TABLE 2

Compound of formula Ib

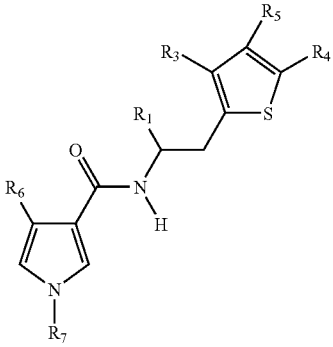

(Ib)

TABLE 2-continued

Compound of formula Ib

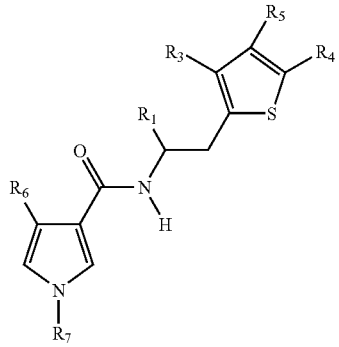

(Ib)

| Compound Number | R₁ | R₃ | R₄ | R₅ | R₆ | R₇ |
|---|---|---|---|---|---|---|
| 2.1 | H | Cl | ethynyl-cyclopropyl | H | CF₂H | Me |
| 2.2 | Me | Cl | ethynyl-cyclopropyl | H | CF₂H | Me |
| 2.3 | H | Br | ethynyl-cyclopropyl | H | CF₂H | Me |
| 2.4 | Me | Br | ethynyl-cyclopropyl | H | CF₂H | Me |
| 2.5 | H | Cl | ethynyl-cyclopentyl | H | CF₂H | Me |
| 2.6 | Me | Cl | ethynyl-cyclopentyl | H | CF₂H | Me |
| 2.7 | H | Br | ethynyl-cyclopentyl | H | CF₂H | Me |
| 2.8 | Me | Cl | ethynyl-cyclopentyl | H | CF₂H | Me |
| 2.9 | H | Cl | ethynyl-cyclohexyl | H | CF₂H | Me |
| 2.10 | Me | Cl | ethynyl-cyclohexyl | H | CF₂H | Me |
| 2.11 | H | Br | ethynyl-cyclohexyl | H | CF₂H | Me |
| 2.12 | Me | Br | ethynyl-cyclohexyl | H | CF₂H | Me |
| 2.13 | H | Cl | ethynyl-phenyl | H | CF₂H | Me |
| 2.14 | Me | Cl | ethynyl-phenyl | H | CF₂H | Me |

TABLE 2-continued

Compound of formula Ib $$\text{(Ib)}$$

Structure: R6-substituted pyrrole (N-R7) with C(=O)NH linker to CHR1-CH2-thiophene (with R3, R4, R5 substituents)

| Compound Number | R1 | R3 | R4 | R5 | R6 | R7 |
|---|---|---|---|---|---|---|
| 2.15 | H | Br | phenylethynyl | H | CF2H | Me |
| 2.16 | Me | Br | phenylethynyl | H | CF2H | Me |
| 2.17 | H | Cl | 4-chlorophenyl | H | CF2H | Me |
| 2.18 | Me | Cl | 4-chlorophenyl | H | CF2H | Me |
| 2.19 | H | Br | 4-chlorophenyl | H | CF2H | Me |
| 2.20 | Me | Br | 4-chlorophenyl | H | CF2H | Me |
| 2.21 | H | Cl | 4-fluorophenyl | H | CF2H | Me |
| 2.22 | Me | Cl | 4-fluorophenyl | H | CF2H | Me |
| 2.23 | H | Br | 4-fluorophenyl | H | CF2H | Me |
| 2.24 | Me | Br | 4-fluorophenyl | H | CF2H | Me |
| 2.25 | H | Cl | cyclopropylethynyl | H | CF3 | Me |
| 2.26 | Me | Cl | cyclopropylethynyl | H | CF3 | Me |
| 2.27 | H | Br | cyclopropylethynyl | H | CF3 | Me |
| 2.28 | Me | Br | cyclopropylethynyl | H | CF3 | Me |
| 2.29 | H | Cl | cyclopentylethynyl | H | CF3 | Me |
| 2.30 | Me | Cl | cyclopentylethynyl | H | CF3 | Me |
| 2.31 | H | Br | cyclopentylethynyl | H | CF3 | Me |
| 2.32 | Me | Cl | cyclopentylethynyl | H | CF3 | Me |
| 2.33 | H | Cl | cyclohexylethynyl | H | CF3 | Me |
| 2.34 | Me | Cl | cyclohexylethynyl | H | CF3 | Me |
| 2.35 | H | Br | cyclohexylethynyl | H | CF3 | Me |
| 2.36 | Me | Br | cyclohexylethynyl | H | CF3 | Me |
| 2.37 | H | Cl | phenylethynyl | H | CF3 | Me |
| 2.38 | Me | Cl | phenylethynyl | H | CF3 | Me |

TABLE 2-continued

Compound of formula Ib (Ib)

| Compound Number | $R_1$ | $R_3$ | $R_4$ | $R_5$ | $R_6$ | $R_7$ |
|---|---|---|---|---|---|---|
| 2.39 | H | Br | phenylethynyl | H | $CF_3$ | Me |
| 2.40 | Me | Br | phenylethynyl | H | $CF_3$ | Me |
| 2.41 | H | Cl | 4-chlorophenyl | H | $CF_3$ | Me |
| 2.42 | Me | Cl | 4-chlorophenyl | H | $CF_3$ | Me |
| 2.43 | H | Br | 4-chlorophenyl | H | $CF_3$ | Me |
| 2.44 | Me | Br | 4-chlorophenyl | H | $CF_3$ | Me |
| 2.45 | H | Cl | 4-fluorophenyl | H | $CF_3$ | Me |
| 2.46 | Me | Cl | 4-fluorophenyl | H | $CF_3$ | Me |
| 2.47 | H | Br | 4-fluorophenyl | H | $CF_3$ | Me |
| 2.48 | Me | Br | 4-fluorophenyl | H | $CF_3$ | Me |

TABLE 3

Compounds of Formula Ic (Ic)

| Compound Number | $R_1$ | $R_3$ | $R_4$ | $R_5$ | $R_6$ | $R_7$ |
|---|---|---|---|---|---|---|
| 3.1 | H | Cl | cyclopropylethynyl | H | $CF_2H$ | Me |
| 3.2 | Me | Cl | cyclopropylethynyl | H | $CF_2H$ | Me |
| 3.3 | H | Br | cyclopropylethynyl | H | $CF_2H$ | Me |
| 3.4 | Me | Br | cyclopropylethynyl | H | $CF_2H$ | Me |
| 3.5 | H | Cl | cyclopentylethynyl | H | $CF_2H$ | Me |
| 3.6 | Me | Cl | cyclopentylethynyl | H | $CF_2H$ | Me |
| 3.7 | H | Br | cyclopentylethynyl | H | $CF_2H$ | Me |
| 3.8 | Me | Cl | cyclopentylethynyl | H | $CF_2H$ | Me |
| 3.9 | H | Cl | cyclohexylethynyl | H | $CF_2H$ | Me |
| 3.10 | Me | Cl | cyclohexylethynyl | H | $CF_2H$ | Me |
| 3.11 | H | Br | cyclohexylethynyl | H | $CF_2H$ | Me |
| 3.12 | Me | Br | cyclohexylethynyl | H | $CF_2H$ | Me |
| 3.13 | H | Cl | phenylethynyl | H | $CF_2H$ | Me |

TABLE 3-continued

Compounds of Formula Ic

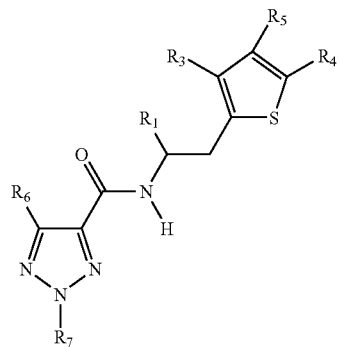
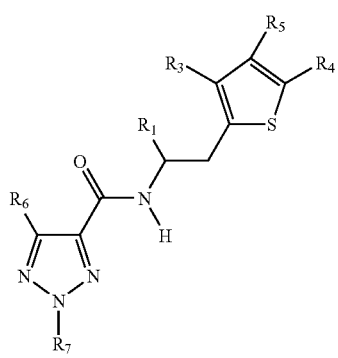

(Ic)

| Compound Number | R₁ | R₃ | R₄ | R₅ | R₆ | R₇ |
|---|---|---|---|---|---|---|
| 3.14 | Me | Cl | ethynyl-phenyl | H | CF₂H | Me |
| 3.15 | H | Br | ethynyl-phenyl | H | CF₂H | Me |
| 3.16 | Me | Br | ethynyl-phenyl | H | CF₂H | Me |
| 3.17 | H | Cl | ethynyl-(4-Cl-phenyl) | H | CF₂H | Me |
| 3.18 | Me | Cl | ethynyl-(4-Cl-phenyl) | H | CF₂H | Me |
| 3.19 | H | Br | ethynyl-(4-Cl-phenyl) | H | CF₂H | Me |
| 3.20 | Me | Br | ethynyl-(4-Cl-phenyl) | H | CF₂H | Me |
| 3.21 | H | Cl | ethynyl-(4-F-phenyl) | H | CF₂H | Me |
| 3.22 | Me | Cl | ethynyl-(4-F-phenyl) | H | CF₂H | Me |
| 3.23 | H | Br | ethynyl-(4-F-phenyl) | H | CF₂H | Me |
| 3.24 | Me | Br | ethynyl-(4-F-phenyl) | H | CF₂H | Me |
| 3.25 | H | Cl | ethynyl-cyclopropyl | H | CF₃ | Me |
| 3.26 | Me | Cl | ethynyl-cyclopropyl | H | CF₃ | Me |
| 3.27 | H | Br | ethynyl-cyclopropyl | H | CF₃ | Me |
| 3.28 | Me | Br | ethynyl-cyclopropyl | H | CF₃ | Me |
| 3.29 | H | Cl | ethynyl-cyclopentyl | H | CF₃ | Me |
| 3.30 | Me | Cl | ethynyl-cyclopentyl | H | CF₃ | Me |
| 3.31 | H | Br | ethynyl-cyclopentyl | H | CF₃ | Me |
| 3.32 | Me | Cl | ethynyl-cyclopentyl | H | CF₃ | Me |
| 3.33 | H | Cl | ethynyl-cyclohexyl | H | CF₃ | Me |
| 3.34 | Me | Cl | ethynyl-cyclohexyl | H | CF₃ | Me |
| 3.35 | H | Br | ethynyl-cyclohexyl | H | CF₃ | Me |
| 3.36 | Me | Br | ethynyl-cyclohexyl | H | CF₃ | Me |

TABLE 3-continued

Compounds of Formula Ic

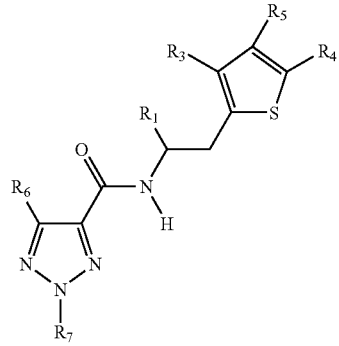

(Ic)

| Compound Number | $R_1$ | $R_3$ | $R_4$ | $R_5$ | $R_6$ | $R_7$ |
|---|---|---|---|---|---|---|
| 3.37 | H | Cl | –C≡C–Ph | H | $CF_3$ | Me |
| 3.38 | Me | Cl | –C≡C–Ph | H | $CF_3$ | Me |
| 3.39 | H | Br | –C≡C–Ph | H | $CF_3$ | Me |
| 3.40 | Me | Br | –C≡C–Ph | H | $CF_3$ | Me |
| 3.41 | H | Cl | –C$_6$H$_4$–4-Cl | H | $CF_3$ | Me |
| 3.42 | Me | Cl | –C$_6$H$_4$–4-Cl | H | $CF_3$ | Me |
| 3.43 | H | Br | –C$_6$H$_4$–4-Cl | H | $CF_3$ | Me |
| 3.44 | Me | Br | –C$_6$H$_4$–4-Cl | H | $CF_3$ | Me |
| 3.45 | H | Cl | –C$_6$H$_4$–4-F | H | $CF_3$ | Me |
| 3.46 | Me | Cl | –C$_6$H$_4$–4-F | H | $CF_3$ | Me |
| 3.47 | H | Br | –C$_6$H$_4$–4-F | H | $CF_3$ | Me |
| 3.48 | Me | Br | –C$_6$H$_4$–4-F | H | $CF_3$ | Me |

TABLE 4

Compounds of formula Id

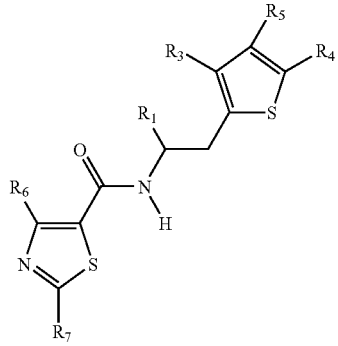

(Id)

| Compound Number | $R_1$ | $R_3$ | $R_4$ | $R_5$ | $R_6$ | $R_7$ |
|---|---|---|---|---|---|---|
| 4.1 | H | Cl | –C≡C–cyclopropyl | H | $CF_2H$ | Me |
| 4.2 | Me | Cl | –C≡C–cyclopropyl | H | $CF_2H$ | Me |
| 4.3 | H | Br | –C≡C–cyclopropyl | H | $CF_2H$ | Me |
| 4.4 | Me | Br | –C≡C–cyclopropyl | H | $CF_2H$ | Me |
| 4.5 | H | Cl | –C≡C–cyclopentyl | H | $CF_2H$ | Me |
| 4.6 | Me | Cl | –C≡C–cyclopentyl | H | $CF_2H$ | Me |

TABLE 4-continued

Compounds of formula Id

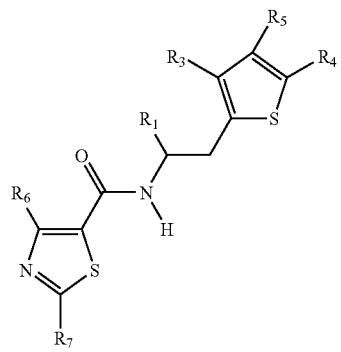

(Id)

| Compound Number | R₁ | R₃ | R₄ | R₅ | R₆ | R₇ |
|---|---|---|---|---|---|---|
| 4.7 | H | Br | ethynyl-cyclopentyl | H | CF₂H | Me |
| 4.8 | Me | Cl | ethynyl-cyclopentyl | H | CF₂H | Me |
| 4.9 | H | Cl | ethynyl-cyclohexyl | H | CF₂H | Me |
| 4.10 | Me | Cl | ethynyl-cyclohexyl | H | CF₂H | Me |
| 4.11 | H | Br | ethynyl-cyclohexyl | H | CF₂H | Me |
| 4.12 | Me | Br | ethynyl-cyclohexyl | H | CF₂H | Me |
| 4.13 | H | Cl | ethynyl-phenyl | H | CF₂H | Me |
| 4.14 | Me | Cl | ethynyl-phenyl | H | CF₂H | Me |
| 4.15 | H | Br | ethynyl-phenyl | H | CF₂H | Me |
| 4.16 | Me | Br | ethynyl-phenyl | H | CF₂H | Me |
| 4.17 | H | Cl | 4-Cl-phenyl | H | CF₂H | Me |

TABLE 4-continued

Compounds of formula Id

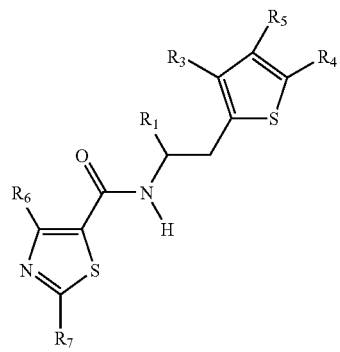

(Id)

| Compound Number | R₁ | R₃ | R₄ | R₅ | R₆ | R₇ |
|---|---|---|---|---|---|---|
| 4.18 | Me | Cl | 4-Cl-phenyl | H | CF₂H | Me |
| 4.19 | H | Br | 4-Cl-phenyl | H | CF₂H | Me |
| 4.20 | Me | Br | 4-Cl-phenyl | H | CF₂H | Me |
| 4.21 | Me | Cl | 4-F-phenyl | H | CF₂H | Me |
| 4.22 | Me | Cl | 4-F-phenyl | H | CF₂H | Me |
| 4.23 | H | Br | 4-F-phenyl | H | CF₂H | Me |
| 4.24 | Me | Br | 4-F-phenyl | H | CF₂H | Me |
| 4.25 | H | Cl | ethynyl-cyclopropyl | H | CF₃ | Me |
| 4.26 | Me | Cl | ethynyl-cyclopropyl | H | CF₃ | Me |
| 4.27 | H | Br | ethynyl-cyclopropyl | H | CF₃ | Me |
| 4.28 | Me | Br | ethynyl-cyclopropyl | H | CF₃ | Me |
| 4.29 | H | Cl | ethynyl-cyclopentyl | H | CF₃ | Me |

TABLE 4-continued

Compounds of formula Id (Id)

| Compound Number | R₁ | R₃ | R₄ | R₅ | R₆ | R₇ |
|---|---|---|---|---|---|---|
| 4.30 | Me | Cl | ─≡─cyclopentyl | H | CF₃ | Me |
| 4.31 | H | Br | ─≡─cyclopentyl | H | CF₃ | Me |
| 4.32 | Me | Cl | ─≡─cyclopentyl | H | CF₃ | Me |
| 4.33 | H | Cl | ─≡─cyclohexyl | H | CF₃ | Me |
| 4.34 | Me | Cl | ─≡─cyclohexyl | H | CF₃ | Me |
| 4.35 | H | Br | ─≡─cyclohexyl | H | CF₃ | Me |
| 4.36 | Me | Br | ─≡─cyclohexyl | H | CF₃ | Me |
| 4.37 | H | Cl | ─≡─phenyl | H | CF₃ | Me |
| 4.38 | Me | Cl | ─≡─phenyl | H | CF₃ | Me |
| 4.39 | H | Br | ─≡─phenyl | H | CF₃ | Me |
| 4.40 | Me | Br | ─≡─phenyl | H | CF₃ | Me |
| 4.41 | H | Cl | ─(4-Cl-phenyl) | H | CF₃ | Me |
| 4.42 | Me | Cl | ─(4-Cl-phenyl) | H | CF₃ | Me |
| 4.43 | H | Br | ─(4-Cl-phenyl) | H | CF₃ | Me |
| 4.44 | Me | Br | ─(4-Cl-phenyl) | H | CF₃ | Me |
| 4.45 | H | Cl | ─(4-F-phenyl) | H | CF₃ | Me |
| 4.46 | Me | Cl | ─(4-F-phenyl) | H | CF₃ | Me |
| 4.47 | H | Br | ─(4-F-phenyl) | H | CF₃ | Me |
| 4.48 | Me | Br | ─(4-F-phenyl) | H | CF₃ | Me |

Compounds of formula Ie
(Ie)
| Compound Number | R₁ | R₃ | R₄ | R₅ | R₆ |
|---|---|---|---|---|---|
| 5.1 | H | Cl | 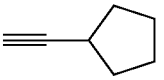 | H | Cl |
| 5.2 | Me | Cl |  | H | Cl |
| 5.3 | H | Cl | 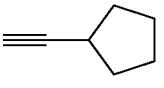 | H | Br |
| 5.4 | Me | Cl |  | H | Br |
| 5.5 | H | Cl | 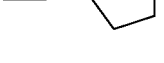 | H | CF₃ |
| 5.6 | Me | Cl |  | H | CF₃ |
| 5.7 | H | Br |  | H | Cl |
| 5.8 | Me | Br |  | H | Cl |
| 5.9 | H | Br | 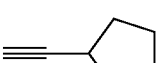 | H | Br |
| 5.10 | Me | Br |  | H | Br |
| 5.11 | H | Br | 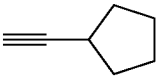 | H | CF₃ |
| 5.12 | Me | Br |  | H | CF₃ |
| 5.13 | H | Cl | 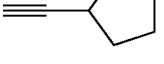 | H | Cl |
| 5.14 | Me | Cl |  | H | Cl |
| 5.15 | H | Cl | 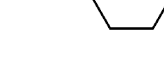 | H | Br |
| 5.16 | Me | Cl |  | H | Br |
| 5.17 | H | Cl | 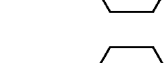 | H | CF₃ |
| 5.18 | Me | Cl |  | H | CF₃ |
| 5.19 | H | Br |  | H | Cl |
| 5.20 | Me | Br |  | H | Cl |
| 5.21 | H | Br |  | H | Br |
| 5.22 | Me | Br |  | H | Br |
| 5.23 | H | Br |  | H | CF₃ |
| 5.24 | Me | Br |  | H | CF₃ |
| 5.25 | H | Cl |  | H | Cl |
| 5.26 | Me | Cl |  | H | Cl |
| 5.27 | H | Cl |  | H | Br |
| 5.28 | Me | Cl |  | H | Br |

-continued

Compounds of formula Ie (Ie)

| Compound Number | R₁ | R₃ | R₄ | R₅ | R₆ |
|---|---|---|---|---|---|
| 5.29 | H | Cl | ethynyl-cyclohexyl | H | CF₃ |
| 5.30 | Me | Cl | ethynyl-cyclohexyl | H | CF₃ |
| 5.31 | H | Br | ethynyl-cyclohexyl | H | Cl |
| 5.32 | Me | Br | ethynyl-cyclohexyl | H | Cl |
| 5.33 | H | Br | ethynyl-cyclohexyl | H | Br |
| 5.34 | Me | Br | ethynyl-cyclohexyl | H | Br |
| 5.35 | H | Br | ethynyl-cyclohexyl | H | CF₃ |
| 5.36 | Me | Br | ethynyl-cyclohexyl | H | CF₃ |
| 5.37 | H | Cl | ethynyl-phenyl | H | Cl |
| 5.38 | Me | Cl | ethynyl-phenyl | H | Cl |
| 5.39 | H | Cl | ethynyl-phenyl | H | Br |
| 5.40 | Me | Cl | ethynyl-phenyl | H | Br |
| 5.41 | H | Cl | ethynyl-phenyl | H | CF₃ |
| 5.42 | Me | Cl | ethynyl-phenyl | H | CF₃ |
| 5.43 | H | Br | ethynyl-phenyl | H | Cl |
| 5.44 | Me | Br | ethynyl-phenyl | H | Cl |
| 5.45 | H | Br | ethynyl-phenyl | H | Br |
| 5.46 | Me | Br | ethynyl-phenyl | H | Br |
| 5.47 | H | Br | ethynyl-phenyl | H | CF₃ |
| 5.48 | Me | Br | ethynyl-phenyl | H | CF₃ |
| 5.49 | H | Cl | 4-chlorobenzyl | H | Cl |
| 5.50 | Me | Cl | 4-chlorobenzyl | H | Cl |
| 5.51 | H | Cl | 4-chlorobenzyl | H | Br |
| 5.52 | Me | Cl | 4-chlorobenzyl | H | Br |

Compounds of formula Ie

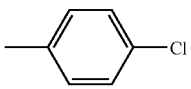

(Ie)

| Compound Number | R₁ | R₃ | R₄ | R₅ | R₆ |
|---|---|---|---|---|---|
| 5.53 | H | Cl | 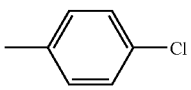 4-Cl-C₆H₄ | H | CF₃ |
| 5.54 | Me | Cl | 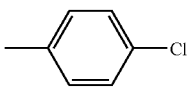 4-Cl-C₆H₄ | H | CF₃ |
| 5.55 | H | Br | 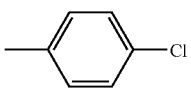 4-Cl-C₆H₄ | H | Cl |
| 5.56 | Me | Br | 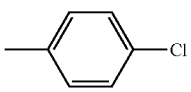 4-Cl-C₆H₄ | H | Cl |
| 5.57 | H | Br | 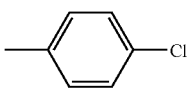 4-Cl-C₆H₄ | H | Br |
| 5.58 | Me | Br |  4-Cl-C₆H₄ | H | Br |
| 5.59 | H | Br | 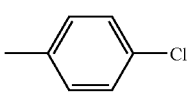 4-Cl-C₆H₄ | H | CF₃ |
| 5.60 | Me | Br | 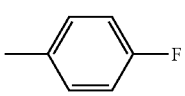 4-Cl-C₆H₄ | H | CF₃ |
| 5.61 | H | Cl | 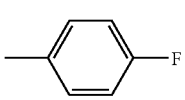 4-F-C₆H₄ | H | Cl |
| 5.62 | Me | Cl | 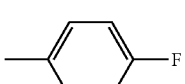 4-F-C₆H₄ | H | Cl |
| 5.63 | H | Cl | 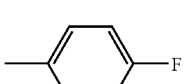 4-F-C₆H₄ | H | Br |
| 5.64 | Me | Cl | 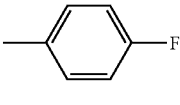 4-F-C₆H₄ | H | Br |

Compounds of formula Ie

(Ie)

| Compound Number | R₁ | R₃ | R₄ | R₅ | R₆ |
|---|---|---|---|---|---|
| 5.65 | H | Cl |  4-F-C₆H₄ | H | CF₃ |
| 5.66 | Me | Cl |  4-F-C₆H₄ | H | CF₃ |
| 5.67 | H | Br |  4-F-C₆H₄ | H | Cl |
| 5.68 | Me | Br | 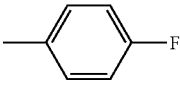 4-F-C₆H₄ | H | Cl |
| 5.69 | H | Br |  4-F-C₆H₄ | H | Br |
| 5.70 | Me | Br | 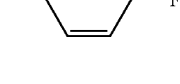 4-F-C₆H₄ | H | Br |
| 5.71 | H | Br | 4-F-C₆H₄ | H | CF₃ |
| 5.72 | Me | Br | 4-F-C₆H₄ | H | CF₃ |

TABLE 6

Compounds of formula If (If) — structure: R6-phenyl-C(=O)-NH-CH(R1)-CH2-thiophene(R3,R4,R5)

| Compound Number | R1 | R3 | R4 | R5 | R6 |
|---|---|---|---|---|---|
| 6.1 | H | Cl | ethynyl-cyclopropyl | H | CF2H |
| 6.2 | Me | Cl | ethynyl-cyclopropyl | H | CF3 |
| 6.3 | H | Br | ethynyl-cyclopropyl | H | CF2H |
| 6.4 | Me | Br | ethynyl-cyclopropyl | H | CF3 |
| 6.5 | H | Cl | ethynyl-cyclopentyl | H | CF2H |
| 6.6 | Me | Cl | ethynyl-cyclopentyl | H | CF3 |
| 6.7 | H | Br | ethynyl-cyclopentyl | H | CF2H |
| 6.8 | Me | Br | ethynyl-cyclopentyl | H | CF3 |
| 6.9 | H | Cl | ethynyl-cyclohexyl | H | CF2H |
| 6.10 | Me | Cl | ethynyl-cyclohexyl | H | CF3 |
| 6.11 | H | Br | ethynyl-cyclohexyl | H | CF2H |
| 6.12 | Me | Br | ethynyl-cyclohexyl | H | CF3 |
| 6.13 | H | Cl | ethynyl-phenyl | H | CF2H |
| 6.14 | Me | Cl | ethynyl-phenyl | H | CF3 |
| 6.15 | H | Br | ethynyl-phenyl | H | CF2H |
| 6.16 | Me | Br | ethynyl-phenyl | H | CF3 |
| 6.17 | H | Cl | 4-Cl-phenyl | H | CF2H |
| 6.18 | Me | Cl | 4-Cl-phenyl | H | CF3 |
| 6.19 | H | Br | 4-Cl-phenyl | H | CF2H |
| 6.20 | Me | Br | 4-Cl-phenyl | H | CF3 |
| 6.21 | H | Cl | 4-F-phenyl | H | CF2H |
| 6.22 | Me | Cl | 4-F-phenyl | H | CF3 |
| 6.23 | H | Br | 4-F-phenyl | H | CF2H |
| 6.24 | Me | Br | 4-F-phenyl | H | CF3 |

TABLE 7

Compounds of formula Ig

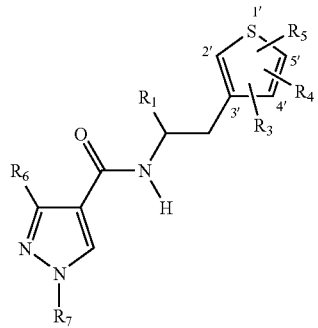

(Ig)

| Compound Number | R₁ | R₃ | R₄ | R₅ | R₆ | R₇ | R₈ |
|---|---|---|---|---|---|---|---|
| 7.1 | H | 4'-Cl | 5'-ethynyl-cyclopropyl | 2'-Cl | Me | Me | F |
| 7.2 | Me | 4'-Cl | 5'-ethynyl-cyclopropyl | 2'-Cl | Me | Me | F |
| 7.3 | H | 4'-Cl | 2'-ethynyl-cyclopropyl | 5'-Cl | Me | Me | F |
| 7.4 | Me | 4'-Cl | 2'-ethynyl-cyclopropyl | 5'-Cl | Me | Me | F |
| 7.5 | H | 4'-Cl | 5'-ethynyl-cyclopentyl | 2'-Cl | Me | Me | F |
| 7.6 | Me | 4'-Cl | 5'-ethynyl-cyclopentyl | 2'-Cl | Me | Me | F |
| 7.7 | H | 4'-Cl | 2'-ethynyl-cyclopentyl | 4'-Cl | Me | Me | F |
| 7.8 | Me | 4'-Cl | 2'-ethynyl-cyclopentyl | 5'-Cl | Me | Me | F |
| 7.9 | H | 4'-Cl | 5'-ethynyl-cyclohexyl | 2'-Cl | Me | Me | F |
| 7.10 | Me | 4'-Cl | 5'-ethynyl-cyclohexyl | 2'-Cl | Me | Me | F |
| 7.11 | H | 4'-Cl | 2'-ethynyl-cyclohexyl | 5'-Cl | Me | Me | F |
| 7.12 | Me | 4'-Cl | 2'-ethynyl-cyclohexyl | 5'-Cl | Me | Me | F |
| 7.13 | H | 4'-Cl | 5'-ethynyl-phenyl | 2'-Cl | Me | Me | F |
| 7.14 | Me | 4'-Cl | 5'-ethynyl-phenyl | 2'-Cl | Me | Me | F |
| 7.15 | H | 4'-Cl | 2'-ethynyl-phenyl | 5'-Cl | Me | Me | F |
| 7.16 | Me | 4'-Cl | 2'-ethynyl-phenyl | 5'-Cl | Me | Me | F |
| 7.17 | H | 4'-Cl | 5'-(4-chlorophenyl) | 2'-Cl | Me | Me | F |
| 7.18 | Me | 4'-Cl | 2'-(4-chlorophenyl) | 5'-Cl | Me | Me | F |
| 7.19 | H | 4'-Cl | 2'-(4-chlorophenyl) | 5'-Cl | Me | Me | F |
| 7.20 | Me | 4'-Cl | 2'-(4-chlorophenyl) | 5'-Cl | Me | Me | F |
| 7.21 | H | 4'-Cl | 5'-(4-fluorophenyl) | 2'-Cl | Me | Me | F |
| 7.22 | Me | 4'-Cl | 5'-(4-fluorophenyl) | 2'-Cl | Me | Me | F |
| 7.23 | H | 4'-Cl | 2'-(4-fluorophenyl) | 5'-Cl | Me | Me | F |
| 7.24 | Me | 4'-Cl | 2'-(4-fluorophenyl) | 5'-Cl | Me | Me | F |

TABLE 7-continued

Compounds of formula Ig (Ig)

| Compound Number | R1 | R3 | R4 | R5 | R6 | R7 | R8 |
|---|---|---|---|---|---|---|---|
| 7.25 | H | 4'-Cl | 5'-ethynyl-cyclopropyl | 2'-Cl | CF2H | Me | H |
| 7.26 | Me | 4'-Cl | 5'-ethynyl-cyclopropyl | 2'-Cl | CF2H | Me | H |
| 7.27 | H | 4'-Cl | 2'-ethynyl-cyclopropyl | 5'-Cl | CF2H | Me | H |
| 7.28 | Me | 4'-Cl | 2'-ethynyl-cyclopropyl | 5'-Cl | CF2H | Me | H |
| 7.29 | H | 4'-Cl | 5'-ethynyl-cyclopentyl | 2'-Cl | CF2H | Me | H |
| 7.30 | Me | 4'-Cl | 5'-ethynyl-cyclopentyl | 2'-Cl | CF2H | Me | H |
| 7.31 | H | 4'-Cl | 2'-ethynyl-cyclopentyl | 5'-Cl | CF2H | Me | H |
| 7.32 | Me | 4'-Cl | 2'-ethynyl-cyclopentyl | 5'-Cl | CF2H | Me | H |
| 7.33 | H | 4'-Cl | 5'-ethynyl-cyclohexyl | 2'-Cl | CF2H | Me | H |
| 7.34 | Me | 4'-Cl | 5'-ethynyl-cyclohexyl | 2'-Cl | CF2H | Me | H |
| 7.35 | H | 4'-Cl | 2'-ethynyl-cyclohexyl | 5'-Cl | CF2H | Me | H |
| 7.36 | Me | 4'-Cl | 2'-ethynyl-cyclohexyl | 5'-Cl | CF2H | Me | H |
| 7.37 | H | 4'-Cl | 5'-ethynyl-phenyl | 2'-Cl | CF2H | Me | H |
| 7.38 | Me | 4'-Cl | 5'-ethynyl-phenyl | 2'-Cl | CF2H | Me | H |
| 7.39 | H | 4'-Cl | 2'-ethynyl-phenyl | 5'-Cl | CF2H | Me | H |
| 7.40 | Me | 4'-Cl | 2'-ethynyl-phenyl | 5'-Cl | CF2H | Me | H |
| 7.41 | H | 4'-Cl | 5'-(4-chlorophenyl) | 2'-Cl | CF2H | Me | H |
| 7.42 | Me | 4'-Cl | 5'-(4-chlorophenyl) | 2'-Cl | CF2H | Me | H |
| 7.43 | H | 4'-Cl | 2'-(4-chlorophenyl) | 5'-Cl | CF2H | Me | H |
| 7.44 | Me | 4'-Cl | 2'-(4-chlorophenyl) | 5'-Cl | CF2H | Me | H |
| 7.45 | H | 4'-Cl | 5'-(4-fluorophenyl) | 2'-Cl | CF2H | Me | H |
| 7.46 | Me | 4'-Cl | 5'-(4-fluorophenyl) | 2'-Cl | CF2H | Me | H |
| 7.47 | H | 4'-Cl | 2'-(4-fluorophenyl) | 5'-Cl | CF2H | Me | H |
| 7.48 | Me | 4'-Cl | 2'-(4-fluorophenyl) | 5'-Cl | CF2H | Me | H |
| 7.49 | H | 4'-Cl | 5'-ethynyl-cyclopropyl | 2'-Cl | CF3 | Me | H |

TABLE 7-continued

Compounds of formula Ig

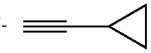

(Ig)

| Compound Number | R₁ | R₃ | R₄ | R₅ | R₆ | R₇ | R₈ |
|---|---|---|---|---|---|---|---|
| 7.50 | Me | 4'-Cl | 5'- 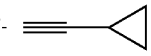 | 2'-Cl | CF₃ | Me | H |
| 7.51 | H | 4'-Cl | 2'-  | 5'-Cl | CF₃ | Me | H |
| 7.52 | Me | 4'-Cl | 2'- 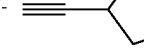 | 5'-Cl | CF₃ | Me | H |
| 7.53 | H | 4'-Cl | 5'- 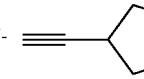 | 2'-Cl | CF₃ | Me | H |
| 7.54 | Me | 4'-Cl | 5'-  | 2'-Cl | CF₃ | Me | H |
| 7.55 | H | 4'-Cl | 2'-  | 5'-Cl | CF₃ | Me | H |
| 7.56 | Me | 4'-Cl | 2'-  | 5'-Cl | CF₃ | Me | H |
| 7.57 | H | 4'-Cl | 5'- 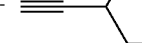 | 2'-Cl | CF₃ | Me | H |
| 7.58 | Me | 4'-Cl | 5'- 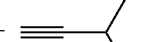 | 2'-Cl | CF₃ | Me | H |
| 7.59 | H | 4'-Cl | 2'-  | 5'-Cl | CF₃ | Me | H |
| 7.60 | Me | 4'-Cl | 2'-  | 5'-Cl | CF₃ | Me | H |
| 7.61 | H | 4'-Cl | 5'- 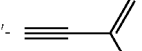 | 2'-Cl | CF₃ | Me | H |
| 7.62 | Me | 4'-Cl | 5'-  | 2'-Cl | CF₃ | Me | H |
| 7.63 | H | 4'-Cl | 2'-  | 5'-Cl | CF₃ | Me | H |
| 7.64 | Me | 4'-Cl | 2'-  | 5'-Cl | CF₃ | Me | H |
| 7.65 | H | 4'-Cl | 5'- 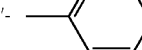 | 2'-Cl | CF₃ | Me | H |
| 7.66 | Me | 4'-Cl | 5'- 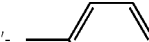 | 2'-Cl | CF₃ | Me | H |
| 7.67 | H | 4'-Cl | 2'- 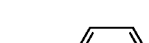 | 5'-Cl | CF₃ | Me | H |
| 7.68 | Me | 4'-Cl | 2'- 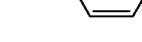 | 5'-Cl | CF₃ | Me | H |
| 7.69 | H | 4'-Cl | 5'- 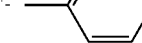 | 2'-Cl | CF₃ | Me | H |
| 7.70 | Me | 4'-Cl | 5'- 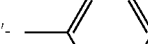 | 2'-Cl | CF₃ | Me | H |
| 7.71 | H | 4'-Cl | 2'- 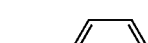 | 5'-Cl | CF₃ | Me | H |
| 7.72 | Me | 4'-Cl | 2'- | 5'-Cl | CF₃ | Me | H |

TABLE 8

Compound of formula Ih

(Ih)

| Compound Number | R₁ | R₃ | R₄ | R₅ | R₆ | R₇ |
|---|---|---|---|---|---|---|
| 8.1 | H | 4'-Cl | 5'-  | 2'-Cl | CF₂H | Me |
| 8.2 | Me | 4'-Cl | 5'-  | 2'-Cl | CF₂H | Me |
| 8.3 | H | 4'-Cl | 2'-  | 5'-Cl | CF₂H | Me |
| 8.4 | Me | 4'-Cl | 2'-  | 5'-Cl | CF₂H | Me |
| 8.5 | H | 4'-Cl | 5'-  | 2'-Cl | CF₂H | Me |
| 8.6 | Me | 4'-Cl | 5'-  | 2'-Cl | CF₂H | Me |
| 8.7 | H | 4'-Cl | 2'-  | 5'-Cl | CF₂H | Me |
| 8.8 | Me | 4'-Cl | 2'-  | 5'-Cl | CF₂H | Me |
| 8.9 | H | 4'-Cl | 5'-  | 2'-Cl | CF₂H | Me |
| 8.10 | Me | 4'-Cl | 5'-  | 2'-Cl | CF₂H | Me |
| 8.11 | H | 4'-Cl | 2'-  | 5'-Cl | CF₂H | Me |
| 8.12 | Me | 4'-Cl | 2'-  | 5'-Cl | CF₂H | Me |
| 8.13 | H | 4'-Cl | 5'-  | 2'-Cl | CF₂H | Me |
| 8.14 | Me | 4'-Cl | 5'-  | 2'-Cl | CF₂H | Me |
| 8.15 | H | 4'-Cl | 2'-  | 5'-Cl | CF₂H | Me |
| 8.16 | Me | 4'-Cl | 2'-  | 5'-Cl | CF₂H | Me |
| 8.17 | H | 4'-Cl | 5'-  | 2'-Cl | CF₂H | Me |
| 8.18 | Me | 4'-Cl | 5'-  | 2'-Cl | CF₂H | Me |
| 8.19 | H | 4'-Cl | 2'-  | 5'-Cl | CF₂H | Me |
| 8.20 | Me | 4'-Cl | 2'-  | 5'-Cl | CF₂H | Me |
| 8.21 | H | 4'-Cl | 5'-  | 2'-Cl | CF₂H | Me |
| 8.22 | Me | 4'-Cl | 5'-  | 2'-Cl | CF₂H | Me |
| 8.23 | H | 4'-Cl | 2'-  | 5'-Cl | CF₂H | Me |
| 8.24 | Me | 4'-Cl | 2'-  | 5'-Cl | CF₂H | Me |
| 8.25 | H | 4'-Cl | 5'- | 2'-Cl | CF₂H | Me |

TABLE 8-continued

Compound of formula Ih

(Ih)

| Compound Number | R₁ | R₃ | R₄ | | R₅ | R₆ | R₇ |
|---|---|---|---|---|---|---|---|
| 8.26 | Me | 4'-Cl | 5'-  | | 2'-Cl | CF₃ | Me |
| 8.27 | H | 4'-Cl | 2'-  | | 5'-Cl | CF₃ | Me |
| 8.28 | Me | 4'-Cl | 2'-  | | 5'-Cl | CF₃ | Me |
| 8.29 | H | 4'-Cl | 5'-  | | 2'-Cl | CF₃ | Me |
| 8.30 | Me | 4'-Cl | 5'-  | | 2'-Cl | CF₃ | Me |
| 8.31 | H | 4'-Cl | 2'-  | | 5'-Cl | CF₃ | Me |
| 8.32 | Me | 4'-Cl | 2'-  | | 5'-Cl | CF₃ | Me |
| 8.33 | H | 4'-Cl | 5'-  | | 2'-Cl | CF₃ | Me |
| 8.34 | Me | 4'-Cl | 5'-  | | 2'-Cl | CF₃ | Me |
| 8.35 | H | 4'-Cl | 2'-  | | 5'-Cl | CF₃ | Me |
| 8.36 | Me | 4'-Cl | 2'-  | | 5'-Cl | CF₃ | Me |
| 8.37 | H | 4'-Cl | 5'-  | | 2'-Cl | CF₃ | Me |
| 8.38 | Me | 4'-Cl | 5'-  | | 2'-Cl | CF₃ | Me |

TABLE 8-continued

Compound of formula Ih

(Ih)

| Compound Number | R₁ | R₃ | R₄ | | R₅ | R₆ | R₇ |
|---|---|---|---|---|---|---|---|
| 8.39 | H | 4'-Cl | 2'-  | | 5'-Cl | CF₃ | Me |
| 8.40 | Me | 4'-Cl | 2'-  | | 5'-Cl | CF₃ | Me |
| 8.41 | H | 4'-Cl | 5'-  | | 2'-Cl | CF₃ | Me |
| 8.42 | Me | 4'-Cl | 5'-  | | 2'-Cl | CF₃ | Me |
| 8.43 | H | 4'-Cl | 2'-  | | 5'-Cl | CF₃ | Me |
| 8.44 | Me | 4'-Cl | 2'-  | | 5'-Cl | CF₃ | Me |
| 8.45 | H | 4'-Cl | 5'-  | | 2'-Cl | CF₃ | Me |
| 8.46 | Me | 4'-Cl | 5'-  | | 2'-Cl | CF₃ | Me |
| 8.47 | H | 4'-Cl | 2'- | | 5'-Cl | CF₃ | Me |
| 8.48 | Me | 4'-Cl | 2'- | | 5'-Cl | CF₃ | Me |

TABLE 9

Compounds of Formula Ii

(Ii)

| Compound Number | R₁ | R₃ | R₄ | | R₅ | R₆ | R₇ |
|---|---|---|---|---|---|---|---|
| 9.1 | H | 4'-Cl | 5'-  | | 2'-Cl | CF₂H | Me |
| 9.2 | Me | 4'-Cl | 5'-  | | 2'-Cl | CF₂H | Me |
| 9.3 | H | 4'-Cl | 2'-  | | 5'-Cl | CF₂H | Me |
| 9.4 | Me | 4'-Cl | 2'-  | | 5'-Cl | CF₂H | Me |
| 9.5 | H | 4'-Cl | 5'-  | | 2'-Cl | CF₂H | Me |
| 9.6 | Me | 4'-Cl | 5'-  | | 2'-Cl | CF₂H | Me |
| 9.7 | H | 4'-Cl | 2'-  | | 5'-Cl | CF₂H | Me |
| 9.8 | Me | 4'-Cl | 2'-  | | 5'-Cl | CF₂H | Me |
| 9.9 | H | 4'-Cl | 5'-  | | 2'-Cl | CF₂H | Me |
| 9.10 | Me | 4'-Cl | 5'-  | | 2'-Cl | CF₂H | Me |
| 9.11 | H | 4'-Cl | 2'-  | | 5'-Cl | CF₂H | Me |
| 9.12 | Me | 4'-Cl | 2'-  | | 5'-Cl | CF₂H | Me |
| 9.13 | H | 4'-Cl | 5'- 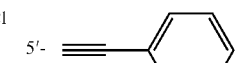 | | 2'-Cl | CF₂H | Me |
| 9.14 | Me | 4'-Cl | 5'-  | | 2'-Cl | CF₂H | Me |
| 9.15 | H | 4'-Cl | 2'-  | | 5'-Cl | CF₂H | Me |
| 9.16 | Me | 4'-Cl | 2'-  | | 5'-Cl | CF₂H | Me |
| 9.17 | H | 4'-Cl | 5'- 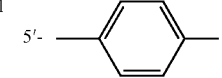 | | 2'-Cl | CF₂H | Me |
| 9.18 | Me | 4'-Cl | 5'- 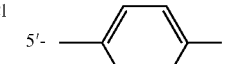 | | 2'-Cl | CF₂H | Me |
| 9.19 | H | 4'-Cl | 2'- 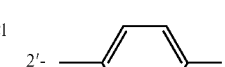 | | 5'-Cl | CF₂H | Me |
| 9.20 | Me | 4'-Cl | 2'- 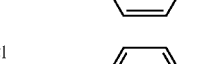 | | 5'-Cl | CF₂H | Me |
| 9.21 | H | 4'-Cl | 5'- 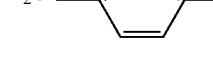 | | 2'-Cl | CF₂H | Me |
| 9.22 | Me | 4'-Cl | 5'- 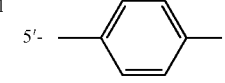 | | 2'-Cl | CF₂H | Me |
| 9.23 | H | 4'-Cl | 2'- 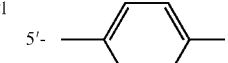 | | 5'-Cl | CF₂H | Me |
| 9.24 | Me | 4'-Cl | 2'- 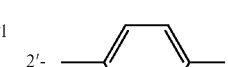 | | 5'-Cl | CF₂H | Me |
| 9.25 | H | 4'-Cl | 5'-  | | 2'-Cl | CF₃ | Me |

TABLE 9-continued

Compounds of Formula Ii

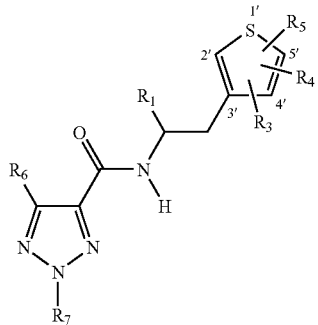

(Ii)

| Compound Number | R₁ | R₃ | R₄ | R₅ | R₆ | R₇ |
|---|---|---|---|---|---|---|
| 9.26 | Me | 4'-Cl | 5'- ≡─◁ | 2'-Cl | CF₃ | Me |
| 9.27 | H | 4'-Cl | 2'- ≡─◁ | 5'-Cl | CF₃ | Me |
| 9.28 | Me | 4'-Cl | 2'- ≡─◁ | 5'-Cl | CF₃ | Me |
| 9.29 | H | 4'-Cl | 5'- ≡─(cyclopentyl) | 2'-Cl | CF₃ | Me |
| 9.30 | Me | 4'-Cl | 5'- ≡─(cyclopentyl) | 2'-Cl | CF₃ | Me |
| 9.31 | H | 4'-Cl | 2'- ≡─(cyclopentyl) | 5'-Cl | CF₃ | Me |
| 9.32 | Me | 4'-Cl | 2'- ≡─(cyclopentyl) | 5'-Cl | CF₃ | Me |
| 9.33 | H | 4'-Cl | 5'- ≡─(cyclohexyl) | 2'-Cl | CF₃ | Me |
| 9.34 | Me | 4'-Cl | 5'- ≡─(cyclohexyl) | 2'-Cl | CF₃ | Me |
| 9.35 | H | 4'-Cl | 2'- ≡─(cyclohexyl) | 5'-Cl | CF₃ | Me |
| 9.36 | Me | 4'-Cl | 2'- ≡─(cyclohexyl) | 5'-Cl | CF₃ | Me |
| 9.37 | H | 4'-Cl | 5'- ≡─Ph | 2'-Cl | CF₃ | Me |

TABLE 9-continued

Compounds of Formula Ii

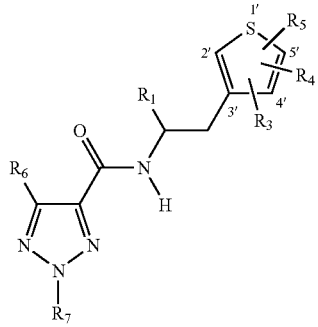

(Ii)

| Compound Number | R₁ | R₃ | R₄ | R₅ | R₆ | R₇ |
|---|---|---|---|---|---|---|
| 9.38 | Me | 4'-Cl | 5'- ≡─Ph | 2'-Cl | CF₃ | Me |
| 9.39 | H | 4'-Cl | 2'- ≡─Ph | 5'-Cl | CF₃ | Me |
| 9.40 | Me | 4'-Cl | 2'- ≡─Ph | 5'-Cl | CF₃ | Me |
| 9.41 | H | 4'-Cl | 5'- ─C₆H₄─Cl | 2'-Cl | CF₃ | Me |
| 9.42 | Me | 4'-Cl | 5'- ─C₆H₄─Cl | 2'-Cl | CF₃ | Me |
| 9.43 | H | 4'-Cl | 2'- ─C₆H₄─Cl | 5'-Cl | CF₃ | Me |
| 9.44 | Me | 4'-Cl | 2'- ─C₆H₄─Cl | 5'-Cl | CF₃ | Me |
| 9.45 | H | 4'-Cl | 5'- ─C₆H₄─F | 2'-Cl | CF₃ | Me |
| 9.46 | Me | 4'-Cl | 5'- ─C₆H₄─F | 2'-Cl | CF₃ | Me |
| 9.47 | H | 4'-Cl | 2'- ─C₆H₄─F | 5'-Cl | CF₃ | Me |
| 9.48 | Me | 4'-Cl | 2'- ─C₆H₄─F | 5'-Cl | CF₃ | Me |

TABLE 10

Compounds of formula Ij

*Structure Ij: thiophene ring (positions 1'-S, 2', 3', 4', 5') with substituents R3, R4, R5, connected via -CH(R1)-CH2- to -NH-C(=O)- of a thiazole ring bearing R6 (position 4) and R7 (position 2).*

| Compound Number | R₁ | R₃ | R₄ | R₅ | R₆ | R₇ |
|---|---|---|---|---|---|---|
| 10.1 | H | 4'-Cl | 5'-C≡C-cyclopropyl | 2'-Cl | CF₂H | Me |
| 10.2 | Me | 4'-Cl | 5'-C≡C-cyclopropyl | 2'-Cl | CF₂H | Me |
| 10.3 | H | 4'-Cl | 2'-C≡C-cyclopropyl | 5'-Cl | CF₂H | Me |
| 10.4 | Me | 4'-Cl | 2'-C≡C-cyclopropyl | 5'-Cl | CF₂H | Me |
| 10.5 | H | 4'-Cl | 5'-C≡C-cyclopentyl | 2'-Cl | CF₂H | Me |
| 10.6 | Me | 4'-Cl | 5'-C≡C-cyclopentyl | 2'-Cl | CF₂H | Me |
| 10.7 | H | 4'-Cl | 2'-C≡C-cyclopentyl | 5'-Cl | CF₂H | Me |
| 10.8 | Me | 4'-Cl | 2'-C≡C-cyclopentyl | 5'-Cl | CF₂H | Me |
| 10.9 | H | 4'-Cl | 5'-C≡C-cyclohexyl | 2'-Cl | CF₂H | Me |
| 10.10 | Me | 4'-Cl | 5'-C≡C-cyclohexyl | 2'-Cl | CF₂H | Me |
| 10.11 | H | 4'-Cl | 2'-C≡C-cyclohexyl | 5'-Cl | CF₂H | Me |
| 10.12 | Me | 4'-Cl | 2'-C≡C-cyclohexyl | 5'-Cl | CF₂H | Me |
| 10.13 | H | 4'-Cl | 5'-C≡C-phenyl | 2'-Cl | CF₂H | Me |
| 10.14 | Me | 4'-Cl | 5'-C≡C-phenyl | 2'-Cl | CF₂H | Me |
| 10.15 | H | 4'-Cl | 2'-C≡C-phenyl | 5'-Cl | CF₂H | Me |
| 10.16 | Me | 4'-Cl | 2'-C≡C-phenyl | 5'-Cl | CF₂H | Me |
| 10.17 | H | 4'-Cl | 5'-(4-Cl-phenyl) | 2'-Cl | CF₂H | Me |
| 10.18 | Me | 4'-Cl | 5'-(4-Cl-phenyl) | 2'-Cl | CF₂H | Me |
| 10.19 | H | 4'-Cl | 2'-(4-Cl-phenyl) | 5'-Cl | CF₂H | Me |
| 10.20 | Me | 4'-Cl | 2'-(4-Cl-phenyl) | 5'-Cl | CF₂H | Me |
| 10.21 | H | 4'-Cl | 5'-(4-F-phenyl) | 2'-Cl | CF₂H | Me |
| 10.22 | Me | 4'-Cl | 5'-(4-F-phenyl) | 2'-Cl | CF₂H | Me |
| 10.23 | H | 4'-Cl | 2'-(4-F-phenyl) | 5'-Cl | CF₂H | Me |
| 10.24 | Me | 4'-Cl | 2'-(4-F-phenyl) | 5'-Cl | CF₂H | Me |
| 10.25 | H | 4'-Cl | 5'-C≡C-cyclopropyl | 2'-Cl | CF₃ | Me |

TABLE 10-continued

Compounds of formula Ij

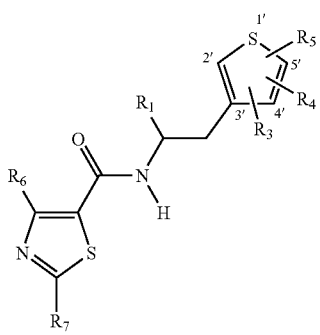

Ij

| Compound Number | R₁ | R₃ | R₄ | R₅ | R₆ | R₇ |
|---|---|---|---|---|---|---|
| 10.26 | Me | 4'-Cl | 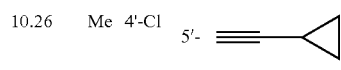 | 2'-Cl | CF₃ | Me |
| 10.27 | H | 4'-Cl | 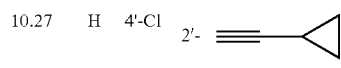 | 5'-Cl | CF₃ | Me |
| 10.28 | Me | 4'-Cl | 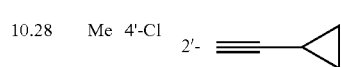 | 5'-Cl | CF₃ | Me |
| 10.29 | H | 4'-Cl | 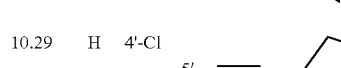 | 2'-Cl | CF₃ | Me |
| 10.30 | Me | 4'-Cl | 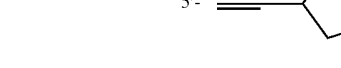 | 2'-Cl | CF₃ | Me |
| 10.31 | H | 4'-Cl | 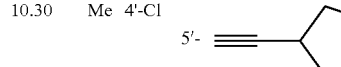 | 5'-Cl | CF₃ | Me |
| 10.32 | Me | 4'-Cl | 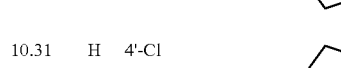 | 5'-Cl | CF₃ | Me |
| 10.33 | H | 4'-Cl | 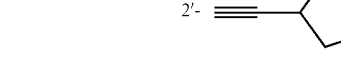 | 2'Cl | CF₃ | Me |
| 10.34 | Me | 4'-Cl | 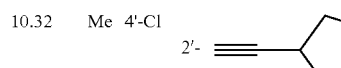 | 2'-Cl | CF₃ | Me |
| 10.35 | H | 4'-Cl | 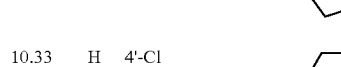 | 5'-Cl | CF₃ | Me |
| 10.36 | Me | 4'-Cl | 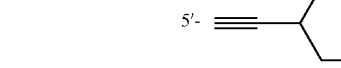 | 5'-Cl | CF₃ | Me |
| 10.37 | H | 4'-Cl | 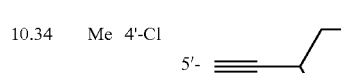 | 2'-Cl | CF₃ | Me |

TABLE 10-continued

Compounds of formula Ij

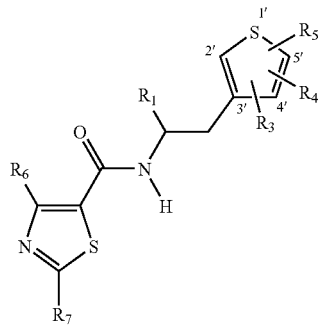

Ij

| Compound Number | R₁ | R₃ | R₄ | R₅ | R₆ | R₇ |
|---|---|---|---|---|---|---|
| 10.38 | Me | 4'-Cl | (5'- ethynylphenyl) | 2'-Cl | CF₃ | Me |
| 10.39 | H | 4'-Cl | (2'- ethynylphenyl) | 5'-Cl | CF₃ | Me |
| 10.40 | Me | 4'-Cl | (2'- ethynylphenyl) | 5'-Cl | CF₃ | Me |
| 10.41 | H | 4'-Cl | (5'- 4-Cl-phenyl) | 2'-Cl | CF₃ | Me |
| 10.42 | Me | 4'-Cl | (5'- 4-Cl-phenyl) | 2'-Cl | CF₃ | Me |
| 10.43 | H | 4'-Cl | (2'- 4-Cl-phenyl) | 5'-Cl | CF₃ | Me |
| 10.44 | Me | 4'-Cl | (2'- 4-Cl-phenyl) | 5'-Cl | CF₃ | Me |
| 10.45 | H | 4'-Cl | (5'- 4-F-phenyl) | 2'-Cl | CF₃ | Me |
| 10.46 | Me | 4'-Cl | (5'- 4-F-phenyl) | 2'-Cl | CF₃ | Me |
| 10.47 | H | 4'-Cl | (2'- 4-F-phenyl) | 5'-Cl | CF₃ | Me |
| 10.48 | Me | 4'-Cl | (2'- 4-F-phenyl) | 5'-Cl | CF₃ | Me |

TABLE 11

Compounds of formula Ik

(Ik)

| Compound Number | R₁ | R₃ | R₄ | R₅ | R₆ |
|---|---|---|---|---|---|
| 11.1 | H | 4'-Cl | 5'-  | 2'-Cl | Cl |
| 11.2 | Me | 4'-Cl | 5'-  | 2'-Cl | Cl |
| 11.3 | H | 4'-Cl | 2'-  | 5'-Cl | Cl |
| 11.4 | Me | 4'-Cl | 2'-  | 5'-Cl | Cl |
| 11.5 | H | 4'-Cl | 5'-  | 2'-Cl | Br |
| 11.6 | Me | 4'-Cl | 5'-  | 2'-Cl | Br |
| 11.7 | H | 4'-Cl | 2'-  | 5'-Cl | Br |
| 11.8 | Me | 4'-Cl | 2'-  | 5'-Cl | Br |
| 11.9 | H | 4'-Cl | 5'-  | 2'-Cl | CF₃ |
| 11.10 | Me | 4'-Cl | 5'-  | 2'-Cl | CF₃ |
| 1.11 | H | 4'-Cl | 2'-  | 5'-Cl | CF₃ |
| 11.12 | Me | 4'-Cl | 2'-  | 5'-Cl | CF₃ |
| 11.13 | H | 4'-Cl | 5'-  | 2'-Cl | Cl |
| 11.14 | Me | 4'-Cl | 5'-  | 2'-Cl | Cl |
| 11.15 | H | 4'-Cl | 2'-  | 5'-Cl | Cl |
| 11.16 | Me | 4'-Cl | 2'-  | 5'-Cl | Cl |
| 11.17 | H | 4'-Cl | 5'-  | 2'-Cl | Br |
| 11.18 | Me | 4'-Cl | 5'-  | 2'-Cl | Br |
| 11.19 | H | 4'-Cl | 2'-  | 5'-Cl | Br |
| 11.20 | Me | 4'-Cl | 2'-  | 5'-Cl | Br |
| 11.21 | H | 4'-Cl | 5'-  | 2'-Cl | CF₃ |
| 11.22 | Me | 4'-Cl | 5'-  | 2'-Cl | CF₃ |
| 11.23 | H | 4'-Cl | 2'-  | 5'-Cl | CF₃ |
| 11.24 | Me | 4'-Cl | 2'-  | 5'-Cl | CF₃ |
| 11.25 | H | 4'-Cl | 5'-  | 2'-Cl | Cl |
| 11.26 | Me | 4'-Cl | 5'-  | 2'-Cl | Cl |
| 11.27 | H | 4'-Cl | 2'-  | 5'-Cl | Cl |
| 11.28 | Me | 4'-Cl | 2'-  | 5'-Cl | Cl |

TABLE 11-continued

Compounds of formula Ik

| Compound Number | R₁ | R₃ | R₄ | R₅ | R₆ |
|---|---|---|---|---|---|
| 11.29 | H | 4'-Cl | 5'- ≡—cyclohexyl | 2'-Cl | Br |
| 11.30 | Me | 4'-Cl | 5'- ≡—cyclohexyl | 2'-Cl | Br |
| 11.31 | H | 4'-Cl | 2'- ≡—cyclohexyl | 5'-Cl | Br |
| 11.32 | Me | 4'-Cl | 2'- ≡—cyclohexyl | 5'-Cl | Br |
| 11.33 | H | 4'-Cl | 5'- ≡—cyclohexyl | 2'-Cl | CF₃ |
| 11.34 | Me | 4'-Cl | 5'- ≡—cyclohexyl | 2'-Cl | CF₃ |
| 11.35 | H | 4'-Cl | 2'- ≡—cyclohexyl | 5'-Cl | CF₃ |
| 11.36 | Me | 4'-Cl | 2'- ≡—cyclohexyl | 5'-Cl | CF₃ |
| 11.37 | H | 4'-Cl | 5'- ≡—phenyl | 2'-Cl | Cl |
| 11.38 | Me | 4'-Cl | 5'- ≡—phenyl | 2'-Cl | Cl |
| 11.39 | H | 4'-Cl | 2'- ≡—phenyl | 5'-Cl | Cl |
| 11.40 | Me | 4'-Cl | 2'- ≡—phenyl | 5'-Cl | Cl |
| 11.41 | H | 4'-Cl | 5'- ≡—phenyl | 2'-Cl | Br |
| 11.42 | Me | 4'-Cl | 5'- ≡—phenyl | 2'-Cl | Br |
| 11.43 | H | 4'-Cl | 2'- ≡—phenyl | 5'-Cl | Br |
| 11.44 | Me | 4'-Cl | 2'- ≡—phenyl | 5'-Cl | Br |
| 11.45 | H | 4'-Cl | 5'- ≡—phenyl | 2'-Cl | CF₃ |
| 11.46 | Me | 4'-Cl | 5'- ≡—phenyl | 2'-Cl | CF₃ |
| 11.47 | H | 4'-Cl | 2'- ≡—phenyl | 5'-Cl | CF₃ |
| 11.48 | Me | 4'-Cl | 2'- ≡—phenyl | 5'-Cl | CF₃ |
| 11.49 | H | 4'-Cl | 5'-—(4-Cl-phenyl) | 2'-Cl | Cl |
| 11.50 | Me | 4'-Cl | 5'-—(4-Cl-phenyl) | 2'-Cl | Cl |
| 11.51 | H | 4'-Cl | 2'-—(4-Cl-phenyl) | 5'-Cl | Cl |
| 11.52 | Me | 4'-Cl | 2'-—(4-Cl-phenyl) | 5'-Cl | Cl |

TABLE 11-continued

Compounds of formula Ik (Ik)

| Compound Number | R₁ | R₃ | R₄ | R₅ | R₆ |
|---|---|---|---|---|---|
| 11.53 | H | 4'-Cl | 5'- —⟨C₆H₄⟩—Cl | 2'-Cl | Br |
| 11.54 | Me | 4'-Cl | 5'- —⟨C₆H₄⟩—Cl | 2'-Cl | Br |
| 11.55 | H | 4'-Cl | 2'- —⟨C₆H₄⟩—Cl | 5'-Cl | Br |
| 11.56 | Me | 4'-Cl | 2'- —⟨C₆H₄⟩—Cl | 5'-Cl | Br |
| 11.57 | H | 4'-Cl | 5'- —⟨C₆H₄⟩—Cl | 2'-Cl | CF₃ |
| 11.58 | Me | 4'-Cl | 5'- —⟨C₆H₄⟩—Cl | 2'-Cl | CF₃ |
| 11.59 | H | 4'-Cl | 2'- —⟨C₆H₄⟩—Cl | 5'-Cl | CF₃ |
| 11.60 | Me | 4'-Cl | 2'- —⟨C₆H₄⟩—Cl | 5'-Cl | CF₃ |
| 11.61 | H | 4'-Cl | 5'- —⟨C₆H₄⟩—F | 2'-Cl | Cl |
| 11.62 | Me | 4'-Cl | 5'- —⟨C₆H₄⟩—F | 2'-Cl | Cl |
| 11.63 | H | 4'-Cl | 2'- —⟨C₆H₄⟩—F | 5'-Cl | Cl |
| 11.64 | Me | 4'-Cl | 2'- —⟨C₆H₄⟩—F | 5'-Cl | Cl |
| 11.65 | H | 4'-Cl | 5'- —⟨C₆H₄⟩—F | 2'-Cl | Br |
| 11.66 | Me | 4'-Cl | 5'- —⟨C₆H₄⟩—F | 2'-Cl | Br |
| 11.67 | H | 4'-Cl | 2'- —⟨C₆H₄⟩—F | 5'-Cl | Br |
| 11.68 | Me | 4'-Cl | 2'- —⟨C₆H₄⟩—F | 5'-Cl | Br |
| 11.69 | H | 4'-Cl | 5'- —⟨C₆H₄⟩—F | 2'-Cl | CF₃ |
| 11.70 | Me | 4'-Cl | 5'- —⟨C₆H₄⟩—F | 2'-Cl | CF₃ |
| 11.71 | H | 4'-Cl | 2'- —⟨C₆H₄⟩—F | 5'-Cl | CF₃ |
| 11.72 | Me | 4'-Cl | 2'- —⟨C₆H₄⟩—F | 5'-Cl | CF₃ |

TABLE 12

Compounds of formula II

(II)

| Compound Number | R₁ | R₃ | R₄ | | R₅ | R₆ |
|---|---|---|---|---|---|---|
| 12.1 | H | 4'-Cl | 5'- |  | 2'-Cl | CF₂H |
| 12.2 | Me | 4'-Cl | 5'- |  | 2'-Cl | CF₂H |
| 12.3 | H | 4'-Cl | 2'- |  | 5'-Cl | CF₂H |
| 12.4 | Me | 4'-Cl | 2'- |  | 5'-Cl | CF₂H |
| 12.5 | H | 4'-Cl | 5'- |  | 2'-Cl | CF₃ |
| 12.6 | Me | 4'-Cl | 5'- |  | 2'-Cl | CF₃ |
| 12.7 | H | 4'-Cl | 2'- |  | 5'-Cl | CF₃ |
| 12.8 | Me | 4'-Cl | 2'- |  | 5'-Cl | CF₃ |
| 12.9 | H | 4'-Cl | 5'- |  | 2'-Cl | CF₂H |
| 12.10 | Me | 4'-Cl | 5'- |  | 2'-Cl | CF₂H |
| 12.11 | H | 4'-Cl | 2'- |  | 5'-Cl | CF₂H |
| 12.12 | Me | 4'-Cl | 2'- |  | 5'-Cl | CF₂H |
| 12.13 | H | 4'-Cl | 5'- |  | 2'-Cl | CF₃ |
| 12.14 | Me | 4'-Cl | 5'- |  | 2'-Cl | CF₃ |
| 12.15 | H | 4'-Cl | 2'- |  | 5'-Cl | CF₃ |
| 12.16 | Me | 4'-Cl | 2'- |  | 5'-Cl | CF₃ |
| 12.17 | H | 4'-Cl | 5'- |  | 2'-Cl | CF₂H |
| 12.18 | Me | 4'-Cl | 5'- |  | 2'-Cl | CF₂H |
| 12.19 | H | 4'-Cl | 2'- |  | 5'-Cl | CF₂H |
| 12.20 | Me | 4'-Cl | 2'- |  | 5'-Cl | CF₂H |
| 12.21 | H | 4'-Cl | 5'- |  | 2'-Cl | CF₃ |
| 12.22 | Me | 4'-Cl | 5'- |  | 2'-Cl | CF₃ |
| 12.23 | H | 4'-Cl | 2'- |  | 5'-Cl | CF₃ |
| 12.24 | Me | 4'-Cl | 2'- |  | 5'-Cl | CF₃ |
| 12.25 | H | 4'-Cl | 5'- |  | 2'-Cl | CF₂H |
| 12.26 | Me | 4'-Cl | 5'- |  | 2'-Cl | CF₂H |
| 12.27 | H | 4'-Cl | 2'- | | 5'-Cl | CF₂H |

TABLE 12-continued

Compounds of formula II (II)

| Compound Number | R₁ | R₃ | R₄ | R₅ | R₆ |
|---|---|---|---|---|---|
| 12.28 | Me | 4'-Cl | 2'- ≡—(phenyl) | 5'-Cl | CF₂H |
| 12.29 | H | 4'-Cl | 5'- ≡—(phenyl) | 2'-Cl | CF₃ |
| 12.30 | Me | 4'-Cl | 5'- ≡—(phenyl) | 2'-Cl | CF₃ |
| 12.31 | H | 4'-Cl | 2'- ≡—(phenyl) | 5'-Cl | CF₃ |
| 12.32 | Me | 4'-Cl | 2'- ≡—(phenyl) | 5'-Cl | CF₃ |
| 12.33 | H | 4'-Cl | 2'- —(4-Cl-phenyl) | 5'-Cl | CF₂H |
| 12.34 | Me | 4'-Cl | 2'- —(4-Cl-phenyl) | 5'-Cl | CF₂H |
| 12.35 | H | 4'-Cl | 5'- —(4-Cl-phenyl) | 2'-Cl | CF₂H |
| 12.36 | Me | 4'-Cl | 5'- —(4-Cl-phenyl) | 2'-Cl | CF₂H |
| 12.37 | H | 4'-Cl | 2'- —(4-Cl-phenyl) | 5'-Cl | CF₃ |
| 12.38 | Me | 4'-Cl | 2'- —(4-Cl-phenyl) | 5'-Cl | CF₃ |
| 12.39 | H | 4'-Cl | 5'- —(4-Cl-phenyl) | 2'-Cl | CF₃ |
| 12.40 | Me | 4'-Cl | 5'- —(4-Cl-phenyl) | 2'-Cl | CF₃ |
| 12.41 | H | 4'-Cl | 2'- —(4-F-phenyl) | 5'-Cl | CF₂H |
| 12.42 | Me | 4'-Cl | 2'- —(4-F-phenyl) | 5'-Cl | CF₂H |
| 12.43 | H | 4'-Cl | 5'- —(4-F-phenyl) | 2'-Cl | CF₂H |
| 12.44 | Me | 4'-Cl | 5'- —(4-F-phenyl) | 2'-Cl | CF₂H |
| 12.45 | H | 4'-Cl | 2'- —(4-F-phenyl) | 5'-Cl | CF₃ |
| 12.46 | Me | 4'-Cl | 2'- —(4-F-phenyl) | 5'-Cl | CF₃ |
| 12.47 | H | 4'-Cl | 5'- —(4-F-phenyl) | 2'-Cl | CF₃ |
| 12.48 | Me | 4'-Cl | 5'- —(4-F-phenyl) | 2'-Cl | CF₃ |

TABLE 13 compounds of formula Im:

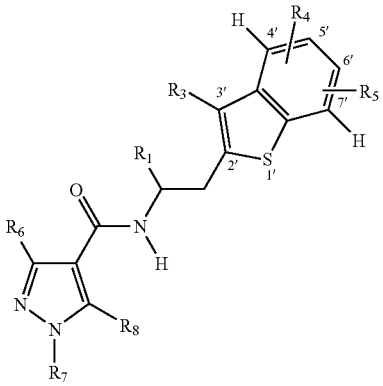

(Im)

| Compound Number | R₁ | R₃ | R₄ | R₅ | R₆ | R₇ | R₈ |
|---|---|---|---|---|---|---|---|
| 13.1 | H | Cl | 5'-≡-cyclopropyl | 6'-H | Me | Me | F |
| 13.2 | Me | Cl | 5'-≡-cyclopropyl | 6'-H | Me | Me | F |
| 13.3 | H | Cl | 6'-≡-cyclopropyl | 5'-H | Me | Me | F |
| 13.4 | Me | Cl | 6'-≡-cyclopropyl | 5'-H | Me | Me | F |
| 13.5 | H | Cl | 5'-≡-cyclopentyl | 6'-H | Me | Me | F |
| 13.6 | Me | Cl | 5'-≡-cyclopentyl | 6'-H | Me | Me | F |
| 13.7 | H | Cl | 6'-≡-cyclopentyl | 5'-H | Me | Me | F |
| 13.8 | Me | Cl | 6'-≡-cyclopentyl | 5'-H | Me | Me | F |
| 13.9 | H | Cl | 5'-≡-cyclohexyl | 6'-H | Me | Me | F |
| 13.10 | Me | Cl | 5'-≡-cyclohexyl | 6'-H | Me | Me | F |
| 13.11 | H | Cl | 6'-≡-cyclohexyl | 5'-H | Me | Me | F |
| 13.12 | Me | Cl | 6'-≡-cyclohexyl | 5'-H | Me | Me | F |

TABLE 13-continued compounds of formula Im:

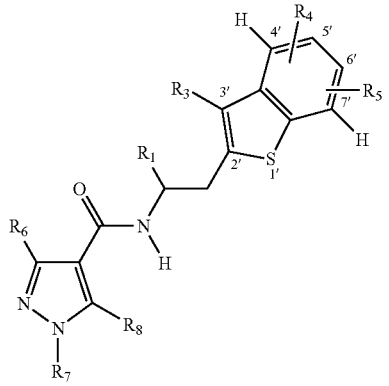

(Im)

| Compound Number | R₁ | R₃ | R₄ | R₅ | R₆ | R₇ | R₈ |
|---|---|---|---|---|---|---|---|
| 13.13 | H | Cl | 5'-≡-phenyl | 6'-H | Me | Me | F |
| 13.14 | Me | Cl | 5'-≡-phenyl | 6'-H | Me | Me | F |
| 13.15 | H | Cl | 6'-≡-phenyl | 5'-H | Me | Me | F |
| 13.16 | Me | Cl | 6'-≡-phenyl | 5'-H | Me | Me | F |
| 13.17 | H | Cl | 5'-(4-Cl-phenyl) | 6'-H | Me | Me | F |
| 13.18 | Me | Cl | 5'-(4-Cl-phenyl) | 6'-H | Me | Me | F |
| 13.19 | H | Cl | 6'-(4-Cl-phenyl) | 5'-H | Me | Me | F |
| 13.20 | Me | Cl | 6'-(4-Cl-phenyl) | 5'-H | Me | Me | F |
| 13.21 | H | Cl | 5'-(4-F-phenyl) | 6'-H | Me | Me | F |
| 13.22 | Me | Cl | 5'-(4-F-phenyl) | 6'-H | Me | Me | F |
| 13.23 | H | Cl | 6'-(4-F-phenyl) | 5'-H | Me | Me | F |

TABLE 13-continued compounds of formula Im:

(Im)

| Compound Number | R₁ | R₃ | R₄ | R₅ | R₆ | R₇ | R₈ |
|---|---|---|---|---|---|---|---|
| 13.24 | Me | Cl | 6'-(4-F-phenyl) | 5'-H | Me | Me | F |
| 13.25 | H | Cl | 5'-C≡C-cyclopropyl | 6'-H | CF₂H | Me | H |
| 13.26 | Me | Cl | 6'-C≡C-cyclopropyl | 6'-H | CF₂H | Me | H |
| 13.27 | H | Cl | 6'-C≡C-cyclopropyl | 5'-H | CF₂H | Me | H |
| 13.28 | Me | Cl | 6'-C≡C-cyclopropyl | 5'-H | CF₂H | Me | H |
| 13.29 | H | Cl | 5'-C≡C-cyclopentyl | 6'-H | CF₂H | Me | H |
| 13.30 | Me | Cl | 5'-C≡C-cyclopentyl | 6'-H | CF₂H | Me | H |
| 13.31 | H | Cl | 6'-C≡C-cyclopentyl | 5'-H | CF₂H | Me | H |
| 13.32 | Me | Cl | 6'-C≡C-cyclopentyl | 5'-H | CF₂H | Me | H |
| 13.33 | H | Cl | 5'-C≡C-cyclohexyl | 6'-H | CF₂H | Me | H |
| 13.34 | Me | Cl | 5'-C≡C-cyclohexyl | 6'-H | CF₂H | Me | H |
| 13.35 | H | Cl | 6'-C≡C-cyclohexyl | 5'-H | CF₂H | Me | H |
| 13.36 | Me | Cl | 6'-C≡C-cyclohexyl | 5'-H | CF₂H | Me | H |
| 13.37 | H | Cl | 5'-C≡C-phenyl | 6'-H | CF₂H | Me | H |
| 13.38 | Me | Cl | 5'-C≡C-phenyl | 6'-H | CF₂H | Me | H |
| 13.39 | H | Cl | 6'-C≡C-phenyl | 5'-H | CF₂H | Me | H |
| 13.40 | Me | Cl | 6'-C≡C-phenyl | 5'-H | CF₂H | Me | H |
| 13.41 | H | Cl | 5'-(4-Cl-phenyl) | 6'-H | CF₂H | Me | H |
| 13.42 | Me | Cl | 5'-(4-Cl-phenyl) | 6'-H | CF₂H | Me | H |
| 13.43 | H | Cl | 6'-(4-Cl-phenyl) | 5'-H | CF₂H | Me | H |
| 13.44 | Me | Cl | 6'-(4-Cl-phenyl) | 5'-H | CF₂H | Me | H |
| 13.45 | H | Cl | 5'-(4-F-phenyl) | 6'-H | CF₂H | Me | H |
| 13.46 | Me | Cl | 5'-(4-F-phenyl) | 6'-H | CF₂H | Me | H |

TABLE 13-continued compounds of formula Im:

(Im)

| Compound Number | R₁ | R₃ | R₄ | R₅ | R₆ | R₇ | R₈ |
|---|---|---|---|---|---|---|---|
| 13.47 | H | Cl | 6'- (4-fluorophenyl) | 5'-H | CF₂H | Me | H |
| 13.48 | Me | Cl | 6'- (4-fluorophenyl) | 5'-H | CF₂H | Me | H |
| 13.49 | H | Cl | 5'- ethynyl-cyclopropyl | 6'-H | CF₃ | Me | H |
| 13.50 | Me | Cl | 5'- ethynyl-cyclopropyl | 6'-H | CF₃ | Me | H |
| 13.51 | H | Cl | 6'- ethynyl-cyclopropyl | 5'-H | CF₃ | Me | H |
| 13.52 | Me | Cl | 6'- ethynyl-cyclopropyl | 5'-H | CF₃ | Me | H |
| 13.53 | H | Cl | 5'- ethynyl-cyclopentyl | 6'-H | CF₃ | Me | H |
| 13.54 | Me | Cl | 5'- ethynyl-cyclopentyl | 6'-H | CF₃ | Me | H |
| 13.55 | H | Cl | 6'- ethynyl-cyclopentyl | 5'-H | CF₃ | Me | H |
| 13.56 | Me | Cl | 6'- ethynyl-cyclopentyl | 5'-H | CF₃ | Me | H |
| 13.57 | H | Cl | 5'- ethynyl-cyclohexyl | 6'-H | CF₃ | Me | H |
| 13.58 | Me | Cl | 5'- ethynyl-cyclohexyl | 6'-H | CF₃ | Me | H |
| 13.59 | H | Cl | 6'- ethynyl-cyclohexyl | 5'-H | CF₃ | Me | H |
| 13.60 | Me | Cl | 6'- ethynyl-cyclohexyl | 5'-H | CF₃ | Me | H |
| 13.61 | H | Cl | 5'- ethynyl-phenyl | 6'-H | CF₃ | Me | H |
| 13.62 | Me | Cl | 5'- ethynyl-phenyl | 6'-H | CF₃ | Me | H |
| 13.63 | H | Cl | 6'- ethynyl-phenyl | 5'-H | CF₃ | Me | H |
| 13.64 | Me | Cl | 6'- ethynyl-phenyl | 5'-H | CF₃ | Me | H |
| 13.65 | H | Cl | 5'- (4-chlorophenyl) | 6'-H | CF₃ | Me | H |
| 13.66 | Me | Cl | 5'- (4-chlorophenyl) | 6'-H | CF₃ | Me | H |
| 13.67 | H | Cl | 6'- (4-chlorophenyl) | 5'-H | CF₃ | Me | H |
| 13.68 | Me | Cl | 6'- (4-chlorophenyl) | 5'-H | CF₃ | Me | H |
| 13.69 | H | Cl | 5'- (4-fluorophenyl) | 6'-H | CF₃ | Me | H |

TABLE 13-continued compounds of formula Im:

(Im)

| Compound Number | $R_1$ | $R_3$ | $R_4$ | $R_5$ | $R_6$ | $R_7$ | $R_8$ |
|---|---|---|---|---|---|---|---|
| 13.70 | Me | Cl | 5'- —⟨C₆H₄⟩—F | 6'-H | $CF_3$ | Me | H |
| 13.71 | H | Cl | 6'- —⟨C₆H₄⟩—F | 5'-H | $CF_3$ | Me | H |
| 13.72 | Me | Cl | 6'- —⟨C₆H₄⟩—F | 5'-H | $CF_3$ | Me | H |

TABLE 14 compound of formula In (In)

| Compound Number | $R_1$ | $R_3$ | $R_4$ | $R_5$ | $R_6$ |
|---|---|---|---|---|---|
| 14.1 | H | Cl | 5'- —≡—cyclopropyl | 6'-H | $CF_3$ |
| 14.2 | Me | Cl | 6'- —≡—cyclopropyl | 5'-H | $CF_3$ |
| 14.3 | H | Cl | 5'- —≡—cyclopentyl | 6'-H | $CF_3$ |

TABLE 14-continued compound of formula In (In)

| Compound Number | $R_1$ | $R_3$ | $R_4$ | $R_5$ | $R_6$ |
|---|---|---|---|---|---|
| 14.4 | Me | Cl | 6'- —≡—cyclopentyl | 5'-H | $CF_3$ |
| 14.5 | H | Cl | 5'- —≡—cyclohexyl | 6'-H | $CF_3$ |
| 14.6 | Me | Cl | 6'- —≡—cyclohexyl | 5'-H | $CF_3$ |
| 14.7 | H | Cl | 5'- —≡—C₆H₅ | 6'-H | $CF_3$ |
| 14.8 | Me | Cl | 6'- —≡—C₆H₅ | 5'-H | $CF_3$ |
| 14.9 | H | Cl | 5'- —⟨C₆H₄⟩—Cl | 6'-H | $CF_3$ |
| 14.10 | Me | Cl | 6'- —⟨C₆H₄⟩—Cl | 5'-H | $CF_3$ |
| 14.11 | H | Cl | 5'- —⟨C₆H₄⟩—F | 6'-H | $CF_3$ |
| 14.12 | Me | Cl | 6'- —⟨C₆H₄⟩—F | 5'-H | $CF_3$ |

Tables 15-17: Compounds of Formula II

The invention is further illustrated by the preferred individual compounds of formula (II) listed below in Tables 15-17. Characterising data is given in Table 21.

TABLE 15

Compounds of formula (IIa)

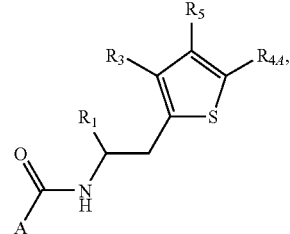

(IIa)

| Cpd No. | R₁ | R₃ | R₄ₐ | R₅ | A |
|---|---|---|---|---|---|
| Z1.1 | H | Cl | Br | H | 3-difluoromethyl-1-methyl-1H-pyrazol-4-yl |
| Z1.2 | Me | Cl | Br | H | 3-difluoromethyl-1-methyl-1H-pyrazol-4-yl |
| Z1.3 | H | Br | Br | H | 3-difluoromethyl-1-methyl-1H-pyrazol-4-yl |
| Z1.4 | Me | Br | Br | H | 3-difluoromethyl-1-methyl-1H-pyrazol-4-yl |
| Z1.5 | H | Cl | Br | H | 3-trifluoromethyl-1-methyl-1H-pyrazol-4-yl |
| Z1.6 | Me | Cl | Br | H | 3-trifluoromethyl-1-methyl-1H-pyrazol-4-yl |
| Z1.7 | H | Br | Br | H | 3-trifluoromethyl-1-methyl-1H-pyrazol-4-yl |
| Z1.8 | Me | Br | Br | H | 3-trifluoromethyl-1-methyl-1H-pyrazol-4-yl |
| Z1.9 | H | Cl | Br | H | 3-difluoromethyl-1-methyl-pyrrol-4-yl |
| Z1.10 | Me | Cl | Br | H | 3-difluoromethyl-1-methyl-pyrrol-4-yl |
| Z1.11 | H | Cl | Br | H | 3-difluoromethyl-1-methyl-1H-triazol-4-yl |
| Z1.12 | Me | Cl | Br | H | 3-difluoromethyl-1-methyl-1H-triazol-4-yl |
| Z1.13 | H | Cl | Br | H | 4-difluoromethyl-2-methyl-thiazol-5-yl |
| Z1.14 | Me | Cl | Br | H | 4-difluoromethyl-2-methyl-thiazol-5-yl |
| Z1.15 | H | Cl | Br | H | 2-chloro-pyridyl-3-yl |
| Z1.16 | Me | Cl | Br | H | 2-chloro-pyridyl-3-yl |
| Z1.17 | H | Cl | Br | H | 2-difluoromethyl-phenyl |
| Z1.18 | Me | Cl | Br | H | 2-difluoromethyl-phenyl |
| Z1.19 | H | Cl | Br | H | 2-trifluoromethyl-phenyl |
| Z1.20 | Me | Cl | Br | H | 2-trifluoromethyl-phenyl |

TABLE 16

Compounds of formula IIb

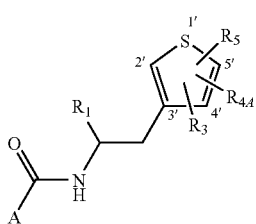

(IIb)

| Cpd No. | R₁ | R₃ | R₄ₐ | R₅ | A |
|---|---|---|---|---|---|
| Z1.21 | H | 4'-Cl | 5'-Br | 2'-Cl | 3-difluoromethyl-1-methyl-1H-pyrazol-4-yl |
| Z1.22 | Me | 4'-Cl | 5'-Br | 2'-Cl | 3-difluoromethyl-1-methyl-1H-pyrazol-4-yl |
| Z1.23 | H | 4'-Cl | 2'-Br | 5'-Cl | 3-difluoromethyl-1-methyl-1H-pyrazol-4-yl |
| Z1.24 | Me | 4'-Cl | 2'-Br | 5'-Cl | 3-difluoromethyl-1-methyl-1H-pyrazol-4-yl |

TABLE 17

Compounds of formula IIc:

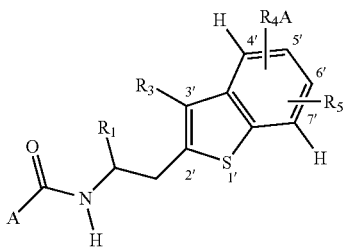

(IIc)

| Cpd No. | R₁ | R₃ | R₄ₐ | R₅ | A |
|---|---|---|---|---|---|
| Z1.25 | H | Cl | 5'-Br | 6'-H | 3-difluoromethyl-1-methyl-1H-pyrazol-4-yl |
| Z1.26 | Me | Cl | 5-Br | 6'-H | 3-difluoromethyl-1-methyl-1H-pyrazol-4-yl |
| Z1.27 | H | Cl | 6'-Br | 5'-H | 3-difluoromethyl-1-methyl-1H-pyrazol-4-yl |
| Z1.28 | Me | Cl | 6'-Br | 6'-H | 3-difluoromethyl-1-methyl-1H-pyrazol-4-yl |

Tables 18-20: Compounds of Formula III

The invention is further illustrated by the preferred individual compounds of formula (III) listed below in Tables 18-20. Characterising data is given in Table 21.

TABLE 18

Compounds of formula (IIIa)

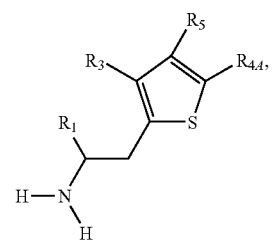

(IIIa)

| Cpd No. | R₁ | R₃ | R₄ₐ | R₅ |
|---|---|---|---|---|
| Z2.1 | H | Cl | Br | H |
| Z2.2 | Me | Cl | Br | H |
| Z2.3 | H | Br | Br | H |
| Z2.4 | Me | Br | Br | H |

TABLE 19

Compounds of formula IIIb

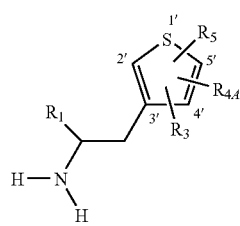

(IIIb)

| Cpd No. | R₁ | R₃ | R₄ₐ | R₅ |
|---|---|---|---|---|
| Z2.5 | H | 4'-Cl | 5'-Br | 2'-Cl |
| Z2.6 | Me | 4'-Cl | 5'-Br | 2'-Cl |

TABLE 19-continued

Compounds of formula IIIb (IIIb)

| Cpd No. | R₁ | R₃ | R₄ₐ | R₅ |
|---|---|---|---|---|
| Z2.7 | H | 4'-Cl | 2'-Br | 5'-Cl |
| Z2.8 | Me | 4'-Cl | 2'-Br | 5'-Cl |

TABLE 20

Compounds of formula IIIc:

(IIIc)

| Cpd No. | R₁ | R₃ | R₄ₐ | R₅ |
|---|---|---|---|---|
| Z2.9 | H | Cl | 5'-Br | 6'-H |
| Z2.10 | Me | Cl | 5-Br | 6'-H |
| Z2.11 | H | Cl | 6'-Br | 5'-H |
| Z2.12 | Me | Cl | 6'-Br | 5'-H |

Table 21: Characterising Data

Table 21 shows selected melting point and selected NMR data for compounds of Tables 1 to 20. CDCl₃ was used as the solvent for NMR measurements, unless otherwise stated. If a mixture of solvents was present, this is indicated as, for example: CDCl₃/d₆-DMSO). No attempt is made to list all characterising data for compounds of Tables 1 to 20. In Table 21 and throughout the description that follows, temperatures are given in degrees Celsius; "NMR" means nuclear magnetic resonance spectrum; MS stands for mass spectrum; "%" is percent by weight, unless corresponding concentrations are indicated in other units. The following abbreviations are used throughout this description:

| | |
|---|---|
| m.p. = melting point | b.p. = boiling point. |
| S = singlet | br = broad |
| d = doublet | dd = doublet of doublets |
| t = triplet | q = quartet |
| m = multiplet | ppm = parts per million |

TABLE 21

| Compound Number | ¹H-NMR data: (ppm/multiplicity/number of Hs). | m.p./ (° C.) |
|---|---|---|
| 1.26 | 0.79/m/2H; 0.88/m/2H; 1.25/d/3H; 1.42/m/1H; 3.0/d/2H; 3.9/s/3H; 4.38/m/1H; 6.25/m/1H; 6.87/s/1H; 6.89/t/1H; 7.85/s/1H | resin |

TABLE 21-continued

| Compound Number | ¹H-NMR data: (ppm/multiplicity/number of Hs). | m.p./ (° C.) |
|---|---|---|
| 1.38 | 1.27/d/3H; 3.09/d/2H; 3.91/s/3H; 4.42/m/1H; 6.22/s/1H; 6.87/t/1H; 7.05/s/1H; 7.35/m/2H; 7.48/m/2H; 7.9/s/1H | resin |
| 1.42 | — | 87-89 |
| 1.46 | 1.28/d/3H; 3.08/d/2H; 3.88/s/3H; 4.45/m/1H; 6.38/s/1H; 6.9/t/1H; 7.05/m/2H; 7.45/m/2H; 7.88/s/1H | wax |
| 6.2 | — | 100-102 |
| 6.14 | — | 130-132 |
| 6.18 | — | 138-140 |
| 6.22 | — | 139-141 |
| 7.28 | — | 135-137 |
| 7.30 | — | 73-77 |
| 7.32 | — | resin |
| 7.46 | — | oil |
| 7.70 | 1.31/d/3H; 2.9/m/2H (diastereotopic protons); 3.97/s/3H; 4.55/m/1H; 5.98/d (broad)/1H; 7.12/t/2H; 7.53/m/2H; 7.87/s/1H) | oil |
| 7.72 | — | 126-130 |
| 12.6 | — | 166-168 |
| 12.30 | — | 172-174 |

Tables 1 to 14: Compounds of Formula IAa

The invention is further illustrated by the preferred individual compounds of formula (IAa) listed below in Tables 1a to 14a.

TABLE 1a

Compounds of formula IAa (IAa)

| Compound Number | R₁ | R₃ | R₄ | R₅ | R₆ | R₇ | R₈ |
|---|---|---|---|---|---|---|---|
| 1a.1 | H | Cl | —≡—◁ | H | Me | Me | F |
| 1a.2 | Me | Cl | —≡—◁ | H | Me | Me | F |
| 1a.3 | H | Br | —≡—◁ | H | Me | Me | F |
| 1a.4 | Me | Br | —≡—◁ | H | Me | Me | F |
| 1a.5 | H | Cl | —≡—⬠ | H | Me | Me | F |

TABLE 1a-continued

Compounds of formula IAa

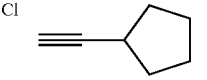

(IAa)

| Compound Number | R$_1$ | R$_3$ | R$_4$ | R$_5$ | R$_6$ | R$_7$ | R$_8$ |
|---|---|---|---|---|---|---|---|
| 1a.6 | Me | Cl | 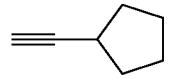 | H | Me | Me | F |
| 1a.7 | H | Br | 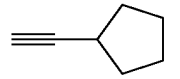 | H | Me | Me | F |
| 1a.8 | Me | Br | 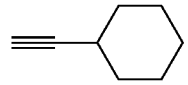 | H | Me | Me | F |
| 1a.9 | H | Cl | 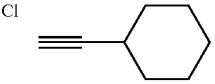 | H | Me | Me | F |
| 1a.10 | Me | Cl | 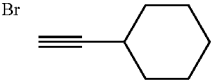 | H | Me | Me | F |
| 1a.11 | H | Br | 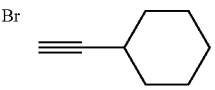 | H | Me | Me | F |
| 1a.12 | Me | Br | 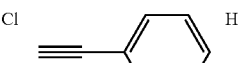 | H | Me | Me | F |
| 1a.13 | H | Cl | 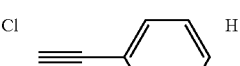 | H | Me | Me | F |
| 1a.14 | Me | Cl | 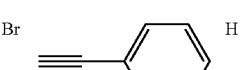 | H | Me | Me | F |
| 1a.15 | H | Br |  | H | Me | Me | F |
| 1a.16 | Me | Br | 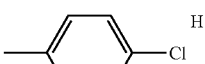 | H | Me | Me | F |
| 1a.17 | H | Cl | 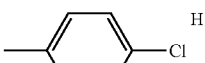 | H | Me | Me | F |
| 1a.18 | Me | Cl | 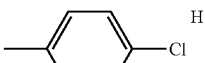 | H | Me | Me | F |
| 1a.19 | H | Br | 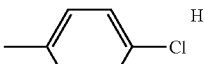 | H | Me | Me | F |
| 1a.20 | Me | Br | 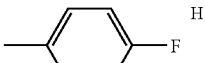 | H | Me | Me | F |
| 1a.21 | H | Cl | 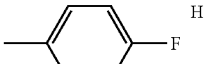 | H | Me | Me | F |
| 1a.22 | Me | Cl | 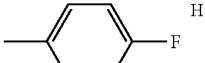 | H | Me | Me | F |
| 1a.23 | H | Br | 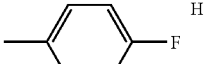 | H | Me | Me | F |
| 1a.24 | Me | Br | 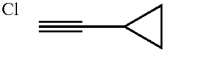 | H | Me | Me | F |
| 1a.25 | H | Cl |  | H | CF$_2$H | Me | H |
| 1a.26 | Me | Cl | 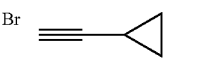 | H | CF$_2$H | Me | H |
| 1a.27 | H | Br | 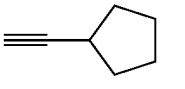 | H | CF$_2$H | Me | H |
| 1a.28 | Me | Br |  | H | CF$_2$H | Me | H |
| 1a.29 | H | Cl |  | H | CF$_2$H | Me | H |

TABLE 1a-continued

Compounds of formula IAa

| Compound Number | R₁ | R₃ | R₄ | R₅ | R₆ | R₇ | R₈ |
|---|---|---|---|---|---|---|---|
| 1a.30 | Me | Cl | ethynyl-cyclopentyl | H | $CF_2H$ | Me | H |
| 1a.31 | H | Br | ethynyl-cyclopentyl | H | $CF_2H$ | Me | H |
| 1a.32 | Me | Br | ethynyl-cyclopentyl | H | $CF_2H$ | Me | H |
| 1a.33 | H | Cl | ethynyl-cyclohexyl | H | $CF_2H$ | Mr | H |
| 1a.34 | Me | Cl | ethynyl-cyclohexyl | H | $CF_2H$ | Me | H |
| 1a.35 | H | Br | ethynyl-cyclohexyl | H | $CF_2H$ | Me | H |
| 1a.36 | Me | Br | ethynyl-cyclohexyl | H | $CF_2H$ | Me | H |
| 1a.37 | H | Cl | ethynyl-phenyl | H | $CF_2H$ | Me | H |
| 1a.38 | Me | Cl | ethynyl-phenyl | H | $CF_2H$ | Me | H |
| 1a.39 | H | Br | ethynyl-phenyl | H | $CF_2H$ | Me | H |
| 1a.40 | Me | Br | ethynyl-phenyl | H | $CF_2H$ | Me | H |
| 1a.41 | H | Cl | 4-chlorophenyl | H | $CF_2H$ | Me | H |
| 1a.42 | Me | Cl | 4-chlorophenyl | H | $CF_2H$ | Me | H |
| 1a.43 | H | Br | 4-chlorophenyl | H | $CF_2H$ | Me | H |
| 1a.44 | Me | Br | 4-chlorophenyl | H | $CF_2H$ | Me | H |
| 1a.45 | H | Cl | 4-fluorophenyl | H | $CF_2H$ | Me | H |
| 1a.46 | Me | Cl | 4-fluorophenyl | H | $CF_2H$ | Me | H |
| 1a.47 | H | Br | 4-fluorophenyl | H | $CF_2H$ | Me | H |
| 1a.48 | Me | Br | 4-fluorophenyl | H | $CF_2H$ | Me | H |
| 1a.49 | H | Cl | ethynyl-cyclopropyl | H | $CF_3$ | Me | H |
| 1a.50 | Me | Cl | ethynyl-cyclopropyl | H | $CF_3$ | Me | H |
| 1a.51 | H | Br | ethynyl-cyclopropyl | H | $CF_3$ | Me | H |
| 1a.52 | Me | Br | ethynyl-cyclopropyl | H | $CF_3$ | Me | H |
| 1a.53 | H | Cl | ethynyl-cyclopentyl | H | $CF_3$ | Me | H |

TABLE 1a-continued

Compounds of formula IAa

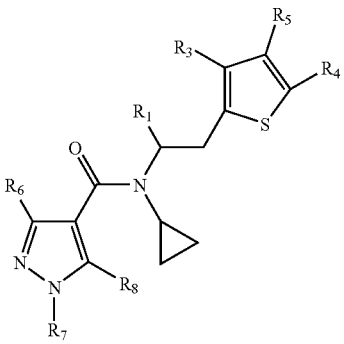

(IAa)

| Compound Number | R₁ | R₃ | R₄ | R₅ | R₆ | R₇ | R₈ |
|---|---|---|---|---|---|---|---|
| 1a.54 | Me | Cl | ethynyl-cyclopentyl | H | CF₃ | Me | H |
| 1a.55 | H | Br | ethynyl-cyclopentyl | H | CF₃ | Me | H |
| 1a.56 | Me | Br | ethynyl-cyclopentyl | H | CF₃ | Me | H |
| 1a.57 | H | Cl | ethynyl-cyclohexyl | H | CF₃ | Me | H |
| 1a.58 | Me | Cl | ethynyl-cyclohexyl | H | CF₃ | Me | H |
| 1a.59 | H | Br | ethynyl-cyclohexyl | H | CF₃ | Me | H |
| 1a.60 | Me | Br | ethynyl-cyclohexyl | H | CF₃ | Me | H |
| 1a.61 | H | Cl | ethynyl-phenyl | H | CF₃ | Me | H |
| 1a.62 | Me | Cl | ethynyl-phenyl | H | CF₃ | Me | H |
| 1a.63 | H | Br | ethynyl-phenyl | H | CF₃ | Me | H |
| 1a.64 | Me | Br | ethynyl-phenyl | H | CF₃ | Me | H |

TABLE 1a-continued

Compounds of formula IAa

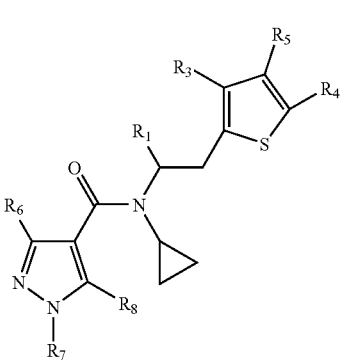

(IAa)

| Compound Number | R₁ | R₃ | R₄ | R₅ | R₆ | R₇ | R₈ |
|---|---|---|---|---|---|---|---|
| 1a.65 | H | Cl | 4-Cl-phenyl | H | CF₃ | Me | H |
| 1a.66 | Me | Cl | 4-Cl-phenyl | H | CF₃ | Me | H |
| 1a.67 | H | Br | 4-Cl-phenyl | H | CF₃ | Me | H |
| 1a.68 | Me | Br | 4-Cl-phenyl | H | CF₃ | Me | H |
| 1a.69 | H | Cl | 4-F-phenyl | H | CF₃ | Me | H |
| 1a.70 | Me | Cl | 4-F-phenyl | H | CF₃ | Me | H |
| 1a.71 | H | Br | 4-F-phenyl | H | CF₃ | Me | H |
| 1a.72 | Me | Br | 4-F-phenyl | H | CF₃ | Me | H |

TABLE 2a

Compound of formula IAb (IAb structure with R1, R3, R4, R5, R6, R7 substituents on pyrrole-carboxamide linked via N-cyclopropyl to a CH(R1)CH2-thiophene)

| Compound Number | R1 | R3 | R4 | R5 | R6 | R7 |
|---|---|---|---|---|---|---|
| 2a.1 | H | Cl | ethynyl-cyclopropyl | H | CF$_2$H | Me |
| 2a.2 | Me | Cl | ethynyl-cyclopropyl | H | CF$_2$H | Me |
| 2a.3 | H | Br | ethynyl-cyclopropyl | H | CF$_2$H | Me |
| 2a.4 | Me | Br | ethynyl-cyclopropyl | H | CF$_2$H | Me |
| 2a.5 | H | Cl | ethynyl-cyclopentyl | H | CF$_2$H | Me |
| 2a.6 | Me | Cl | ethynyl-cyclopentyl | H | CF$_2$H | Me |
| 2a.7 | H | Br | ethynyl-cyclopentyl | H | CF$_2$H | Me |
| 2a.8 | Me | Cl | ethynyl-cyclopentyl | H | CF$_2$H | Me |
| 2a.9 | H | Cl | ethynyl-cyclohexyl | H | CF$_2$H | Me |
| 2a.10 | Me | Cl | ethynyl-cyclohexyl | H | CF$_2$H | Me |
| 2a.11 | H | Br | ethynyl-cyclohexyl | H | CF$_2$H | Me |
| 2a.12 | Me | Br | ethynyl-cyclohexyl | H | CF$_2$H | Me |
| 2a.13 | H | Cl | ethynyl-phenyl | H | CF$_2$H | Me |
| 2a.14 | Me | Cl | ethynyl-phenyl | H | CF$_2$H | Me |
| 2a.15 | H | Br | ethynyl-phenyl | H | CF$_2$H | Me |
| 2a.16 | Me | Br | ethynyl-phenyl | H | CF$_2$H | Me |
| 2a.17 | H | Cl | 4-Cl-phenyl | H | CF$_2$H | Me |
| 2a.18 | Me | Cl | 4-Cl-phenyl | H | CF$_2$H | Me |
| 2a.19 | H | Br | 4-Cl-phenyl | H | CF$_2$H | Me |
| 2a.20 | Me | Br | 4-Cl-phenyl | H | CF$_2$H | Me |
| 2a.21 | H | Cl | 4-F-phenyl | H | CF$_2$H | Me |
| 2a.22 | Me | Cl | 4-F-phenyl | H | CF$_2$H | Me |
| 2a.23 | H | Br | 4-F-phenyl | H | CF$_2$H | Me |
| 2a.24 | Me | Br | 4-F-phenyl | H | CF$_2$H | Me |
| 2a.25 | H | Cl | ethynyl-cyclopropyl | H | CF$_3$ | Me |

TABLE 2a-continued

Compound of formula IAb (IAb)

[Structure: R6-substituted pyrrole (with R7 on N) connected via C(=O)-N(cyclopropyl)-CH(R1)-CH2- to a thiophene bearing R3, R5, R4]

| Compound Number | R₁ | R₃ | R₄ | R₅ | R₆ | R₇ |
|---|---|---|---|---|---|---|
| 2a.26 | Me | Cl | —≡—cyclopropyl | H | CF₃ | Me |
| 2a.27 | H | Br | —≡—cyclopropyl | H | CF₃ | Me |
| 2a.28 | Me | Br | —≡—cyclopropyl | H | CF₃ | Me |
| 2a.29 | H | Cl | —≡—cyclopentyl | H | CF₃ | Me |
| 2a.30 | Me | Cl | —≡—cyclopentyl | H | CF₃ | Me |
| 2a.31 | H | Br | —≡—cyclopentyl | H | CF₃ | Me |
| 2a.32 | Me | Cl | —≡—cyclopentyl | H | CF₃ | Me |
| 2a.33 | H | Cl | —≡—cyclohexyl | H | CF₃ | Me |
| 2a.34 | Me | Cl | —≡—cyclohexyl | H | CF₃ | Me |
| 2a.35 | H | Br | —≡—cyclohexyl | H | CF₃ | Me |
| 2a.36 | Me | Br | —≡—cyclohexyl | H | CF₃ | Me |
| 2a.37 | H | Cl | —≡—phenyl | H | CF₃ | Me |
| 2a.38 | Me | Cl | —≡—phenyl | H | CF₃ | Me |
| 2a.39 | H | Br | —≡—phenyl | H | CF₃ | Me |
| 2a.40 | Me | Br | —≡—phenyl | H | CF₃ | Me |
| 2a.41 | H | Cl | —C₆H₄-4-Cl | H | CF₃ | Me |
| 2a.42 | Me | Cl | —C₆H₄-4-Cl | H | CF₃ | Me |
| 2a.43 | H | Br | —C₆H₄-4-Cl | H | CF₃ | Me |
| 2a.44 | Me | Br | —C₆H₄-4-Cl | H | CF₃ | Me |
| 2a.45 | H | Cl | —C₆H₄-4-F | H | CF₃ | Me |
| 2a.46 | Me | Cl | —C₆H₄-4-F | H | CF₃ | Me |
| 2a.47 | H | Br | —C₆H₄-4-F | H | CF₃ | Me |
| 2a.48 | Me | Br | —C₆H₄-4-F | H | CF₃ | Me |

TABLE 3a

Compounds of Formula IAc

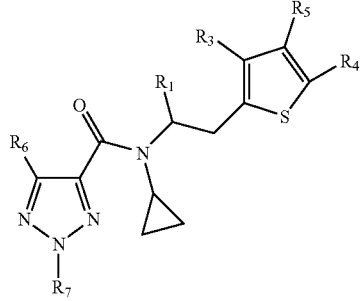

(IAc)

| Compound Number | R₁ | R₃ | R₄ | R₅ | R₆ | R₇ |
|---|---|---|---|---|---|---|
| 3a.1 | H | Cl | ≡–cyclopropyl | H | $CF_2H$ | Me |
| 3a.2 | Me | Cl | ≡–cyclopropyl | H | $CF_2H$ | Me |
| 3a.3 | H | Br | ≡–cyclopropyl | H | $CF_2H$ | Me |
| 3a.4 | Me | Br | ≡–cyclopropyl | H | $CF_2H$ | Me |
| 3a.5 | H | Cl | ≡–cyclopentyl | H | $CF_2H$ | Me |
| 3a.6 | Me | Cl | ≡–cyclopentyl | H | $CF_2H$ | Me |
| 3a.7 | H | Br | ≡–cyclopentyl | H | $CF_2H$ | Me |
| 3a.8 | Me | Cl | ≡–cyclopentyl | H | $CF_2H$ | Me |
| 3a.9 | H | Cl | ≡–cyclohexyl | H | $CF_2H$ | Me |
| 3a.10 | Me | Cl | ≡–cyclohexyl | H | $CF_2H$ | Me |
| 3a.11 | H | Br | ≡–cyclohexyl | H | $CF_2H$ | Me |
| 3a.12 | Me | Br | ≡–cyclohexyl | H | $CF_2H$ | Me |
| 3a.13 | H | Cl | ≡–phenyl | H | $CF_2H$ | Me |

TABLE 3a-continued

Compounds of Formula IAc

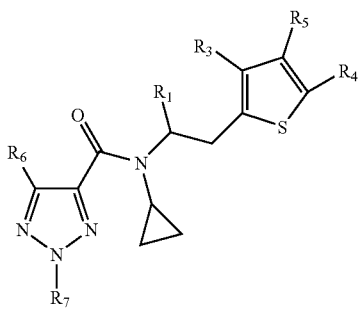

(IAc)

| Compound Number | R₁ | R₃ | R₄ | R₅ | R₆ | R₇ |
|---|---|---|---|---|---|---|
| 3a.14 | Me | Cl | ≡–phenyl | H | $CF_2H$ | Me |
| 3a.15 | H | Br | ≡–phenyl | H | $CF_2H$ | Me |
| 3a.16 | Me | Br | ≡–phenyl | H | $CF_2H$ | Me |
| 3a.17 | H | Cl | 4-Cl-phenyl | H | $CF_2H$ | Me |
| 3a.18 | Me | Cl | 4-Cl-phenyl | H | $CF_2H$ | Me |
| 3a.19 | H | Br | 4-Cl-phenyl | H | $CF_2H$ | Me |
| 3a.20 | Me | Br | 4-Cl-phenyl | H | $CF_2H$ | Me |
| 3a.21 | H | Cl | 4-F-phenyl | H | $CF_2H$ | Me |
| 3a.22 | Me | Cl | 4-F-phenyl | H | $CF_2H$ | Me |
| 3a.23 | H | Br | 4-F-phenyl | H | $CF_2H$ | Me |
| 3a.24 | Me | Br | 4-F-phenyl | H | $CF_2H$ | Me |
| 3a.25 | H | Cl | ≡–cyclopropyl | H | $CF_3$ | Me |

TABLE 3a-continued

Compounds of Formula IAc (IAc)

| Compound Number | R₁ | R₃ | R₄ | R₅ | R₆ | R₇ |
|---|---|---|---|---|---|---|
| 3a.26 | Me | Cl | ≡–cyclopropyl | H | CF₃ | Me |
| 3a.27 | H | Br | ≡–cyclopropyl | H | CF₃ | Me |
| 3a.28 | Me | Br | ≡–cyclopropyl | H | CF₃ | Me |
| 3a.29 | H | Cl | ≡–cyclopentyl | H | CF₃ | Me |
| 3a.30 | Me | Cl | ≡–cyclopentyl | H | CF₃ | Me |
| 3a.31 | H | Br | ≡–cyclopentyl | H | CF₃ | Me |
| 3a.32 | Me | Cl | ≡–cyclopentyl | H | CF₃ | Me |
| 3a.33 | H | Cl | ≡–cyclohexyl | H | CF₃ | Me |
| 3a.34 | Me | Cl | ≡–cyclohexyl | H | CF₃ | Me |
| 3a.35 | H | Br | ≡–cyclohexyl | H | CF₃ | Me |
| 3a.36 | Me | Br | ≡–cyclohexyl | H | CF₃ | Me |
| 3a.37 | H | Cl | ≡–phenyl | H | CF₃ | Me |
| 3a.38 | Me | Cl | ≡–phenyl | H | CF₃ | Me |
| 3a.39 | H | Br | ≡–phenyl | H | CF₃ | Me |
| 3a.40 | Me | Br | ≡–phenyl | H | CF₃ | Me |
| 3a.41 | H | Cl | –C₆H₄–Cl (4-Cl) | H | CF₃ | Me |
| 3a.42 | Me | Cl | –C₆H₄–Cl (4-Cl) | H | CF₃ | Me |
| 3a.43 | H | Br | –C₆H₄–Cl (4-Cl) | H | CF₃ | Me |
| 3a.44 | Me | Br | –C₆H₄–Cl (4-Cl) | H | CF₃ | Me |
| 3a.45 | H | Cl | –C₆H₄–F (4-F) | H | CF₃ | Me |
| 3a.46 | Me | Cl | –C₆H₄–F (4-F) | H | CF₃ | Me |
| 3a.47 | H | Br | –C₆H₄–F (4-F) | H | CF₃ | Me |
| 3a.48 | Me | Br | –C₆H₄–F (4-F) | H | CF₃ | Me |

TABLE 4a

Compounds of formula IAd

| Compound Number | R₁ | R₃ | R₄ | R₅ | R₆ | R₇ |
|---|---|---|---|---|---|---|
| 4a.1 | H | Cl | ethynyl-cyclopropyl | H | CF₂H | Me |
| 4a.2 | Me | Cl | ethynyl-cyclopropyl | H | CF₂H | Me |
| 4a.3 | H | Br | ethynyl-cyclopropyl | H | CF₂H | Me |
| 4a.4 | Me | Br | ethynyl-cyclopropyl | H | CF₂H | Me |
| 4a.5 | H | Cl | ethynyl-cyclopentyl | H | CF₂H | Me |
| 4a.6 | Me | Cl | ethynyl-cyclopentyl | H | CF₂H | Me |
| 4a.7 | H | Br | ethynyl-cyclopentyl | H | CF₂H | Me |
| 4a.8 | Me | Cl | ethynyl-cyclopentyl | H | CF₂H | Me |
| 4a.9 | H | Cl | ethynyl-cyclohexyl | H | CF₂H | Me |
| 4a.10 | Me | Cl | ethynyl-cyclohexyl | H | CF₂H | Me |
| 4a.11 | H | Br | ethynyl-cyclohexyl | H | CF₂H | Me |
| 4a.12 | Me | Br | ethynyl-cyclohexyl | H | CF₂H | Me |
| 4a.13 | H | Cl | ethynyl-phenyl | H | CF₂H | Me |
| 4a.14 | Me | Cl | ethynyl-phenyl | H | CF₂H | Me |
| 4a.15 | H | Br | ethynyl-phenyl | H | CF₂H | Me |
| 4a.16 | Me | Br | ethynyl-phenyl | H | CF₂H | Me |
| 4a.17 | H | Cl | 4-chlorophenyl-methyl | H | CF₂H | Me |
| 4a.18 | Me | Cl | 4-chlorophenyl-methyl | H | CF₂H | Me |
| 4a.19 | H | Br | 4-chlorophenyl-methyl | H | CF₂H | Me |
| 4a.20 | Me | Br | 4-chlorophenyl-methyl | H | CF₂H | Me |
| 4a.21 | Me | Cl | 4-fluorophenyl-methyl | H | CF₂H | Me |
| 4a.22 | Me | Cl | 4-fluorophenyl-methyl | H | CF₂H | Me |
| 4a.23 | H | Br | 4-fluorophenyl-methyl | H | CF₂H | Me |
| 4a.24 | Me | Br | 4-fluorophenyl-methyl | H | CF₂H | Me |
| 4a.25 | H | Cl | ethynyl-cyclopropyl | H | CF₃ | Me |

TABLE 4a-continued

Compounds of formula IAd

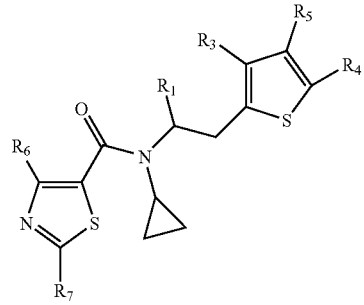

(IAd)

| Compound Number | R₁ | R₃ | R₄ | R₅ | R₆ | R₇ |
|---|---|---|---|---|---|---|
| 4a.26 | Me | Cl | ≡–cyclopropyl | H | CF₃ | Me |
| 4a.27 | H | Br | ≡–cyclopropyl | H | CF₃ | Me |
| 4a.28 | Me | Br | ≡–cyclopropyl | H | CF₃ | Me |
| 4a.29 | H | Cl | ≡–cyclopentyl | H | CF₃ | Me |
| 4a.30 | Me | Cl | ≡–cyclopentyl | H | CF₃ | Me |
| 4a.31 | H | Br | ≡–cyclopentyl | H | CF₃ | Me |
| 4a.32 | Me | Cl | ≡–cyclopentyl | H | CF₃ | Me |
| 4a.33 | H | Cl | ≡–cyclohexyl | H | CF₃ | Me |
| 4a.34 | Me | Cl | ≡–cyclohexyl | H | CF₃ | Me |
| 4a.35 | H | Br | ≡–cyclohexyl | H | CF₃ | Me |
| 4a.36 | Me | Br | ≡–cyclohexyl | H | CF₃ | Me |
| 4a.37 | H | Cl | ≡–phenyl | H | CF₃ | Me |
| 4a.38 | Me | Cl | ≡–phenyl | H | CF₃ | Me |

TABLE 4a-continued

Compounds of formula IAd

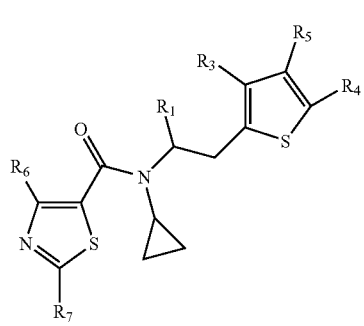

(IAd)

| Compound Number | R₁ | R₃ | R₄ | R₅ | R₆ | R₇ |
|---|---|---|---|---|---|---|
| 4a.39 | H | Br | ≡–phenyl | H | CF₃ | Me |
| 4a.40 | Me | Br | ≡–phenyl | H | CF₃ | Me |
| 4a.41 | H | Cl | 4-Cl-phenyl | H | CF₃ | Me |
| 4a.42 | Me | Cl | 4-Cl-phenyl | H | CF₃ | Me |
| 4a.43 | H | Br | 4-Cl-phenyl | H | CF₃ | Me |
| 4a.44 | Me | Br | 4-Cl-phenyl | H | CF₃ | Me |
| 4a.45 | H | Cl | 4-F-phenyl | H | CF₃ | Me |
| 4a.46 | Me | Cl | 4-F-phenyl | H | CF₃ | Me |
| 4a.47 | H | Br | 4-F-phenyl | H | CF₃ | me |
| 4a.48 | Me | Br | 4-F-phenyl | H | CF₃ | Me |

TABLE 5a
Compounds of formula IAe
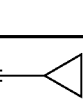
(IAe)
| Compound Number | R₁ | R₃ | R₄ | R₅ | R₆ |
|---|---|---|---|---|---|
| 5a.1 | H | Cl |  | H | Cl |
| 5a.2 | Me | Cl |  | H | Cl |
| 5a.3 | H | Cl |  | H | Br |
| 5a.4 | Me | Cl |  | H | Br |
| 5a.5 | H | Cl |  | H | CF₃ |
| 5a.6 | Me | Cl |  | H | CF₃ |
| 5a.7 | H | Br |  | H | Cl |
| 5a.8 | Me | Br |  | H | Cl |
| 5a.9 | H | Br |  | H | Br |
| 5a.10 | Me | Br |  | H | Br |
| 5a.11 | H | Br |  | H | CF₃ |
| 5a.12 | Me | Br |  | H | CF₃ |
| 5a.13 | H | Cl |  | H | Cl |
| 5a.14 | Me | Cl |  | H | Cl |
| 5a.15 | H | Cl |  | H | Br |
| 5a.16 | Me | Cl | 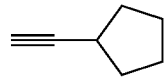 | H | Br |
| 5a.17 | H | Cl | 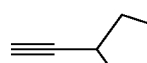 | H | CF₃ |
| 5a.18 | Me | Cl | 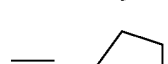 | H | CF₃ |
| 5a.19 | H | Br |  | H | Cl |
| 5a.20 | Me | Br | 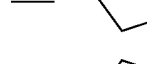 | H | Cl |
| 5a.21 | H | Br | 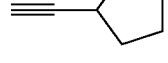 | H | Br |
| 5a.22 | Me | Br | 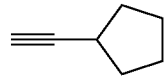 | H | Br |
| 5a.23 | H | Br | 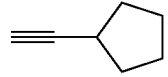 | H | CF₃ |
| 5a.24 | Me | Br | 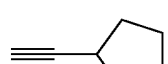 | H | CF₃ |
| 5a.25 | H | Cl |  | H | Cl |
| 5a.26 | Me | Cl |  | H | Cl |
| 5a.27 | H | Cl | 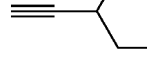 | H | Br |
| 5a.28 | Me | Cl | 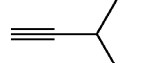 | H | Br |
| 5a.29 | H | Cl | 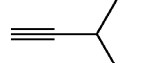 | H | CF₃ |

TABLE 5a-continued

Compounds of formula IAe (IAe)

| Compound Number | R₁ | R₃ | R₄ | R₅ | R₆ |
|---|---|---|---|---|---|
| 5a.30 | Me | Cl | ethynyl-cyclohexyl | H | CF₃ |
| 5a.31 | H | Br | ethynyl-cyclohexyl | H | Cl |
| 5a.32 | Me | Br | ethynyl-cyclohexyl | H | Cl |
| 5a.33 | H | Br | ethynyl-cyclohexyl | H | Br |
| 5a.34 | Me | Br | ethynyl-cyclohexyl | H | Br |
| 5a.35 | H | Br | ethynyl-cyclohexyl | H | CF₃ |
| 5a.36 | Me | Br | ethynyl-cyclohexyl | H | CF₃ |
| 5a.37 | H | Cl | ethynyl-phenyl | H | Cl |
| 5a.38 | Me | Cl | ethynyl-phenyl | H | Cl |
| 5a.39 | H | Cl | ethynyl-phenyl | H | Br |
| 5a.40 | Me | Cl | ethynyl-phenyl | H | Br |
| 5a.41 | H | Cl | ethynyl-phenyl | H | CF₃ |
| 5a.42 | Me | Cl | ethynyl-phenyl | H | CF₃ |
| 5a.43 | H | Br | ethynyl-phenyl | H | Cl |
| 5a.44 | Me | Br | ethynyl-phenyl | H | Cl |
| 5a.45 | H | Br | ethynyl-phenyl | H | Br |
| 5a.46 | Me | Br | ethynyl-phenyl | H | Br |
| 5a.47 | H | Br | ethynyl-phenyl | H | CF₃ |
| 5a.48 | Me | Br | ethynyl-phenyl | H | CF₃ |
| 5a.49 | H | Cl | 4-chlorophenyl | H | Cl |
| 5a.50 | Me | Cl | 4-chlorophenyl | H | Cl |
| 5a.51 | H | Cl | 4-chlorophenyl | H | Br |
| 5a.52 | Me | Cl | 4-chlorophenyl | H | Br |
| 5a.53 | H | Cl | 4-chlorophenyl | H | CF₃ |

TABLE 5a-continued

Compounds of formula IAe (IAe)

| Compound Number | $R_1$ | $R_3$ | $R_4$ | $R_5$ | $R_6$ |
|---|---|---|---|---|---|
| 5a.54 | Me | Cl | 4-Cl-phenyl | H | $CF_3$ |
| 5a.55 | H | Br | 4-Cl-phenyl | H | Cl |
| 5a.56 | Me | Br | 4-Cl-phenyl | H | Cl |
| 5a.57 | H | Br | 4-Cl-phenyl | H | Br |
| 5a.58 | Me | Br | 4-Cl-phenyl | H | Br |
| 5a.59 | H | Br | 4-Cl-phenyl | H | $CF_3$ |
| 5a.60 | Me | Br | 4-Cl-phenyl | H | $CF_3$ |
| 5a.61 | H | Cl | 4-F-phenyl | H | Cl |
| 5a.62 | Me | Cl | 4-F-phenyl | H | Cl |
| 5a.63 | H | Cl | 4-F-phenyl | H | Br |
| 5a.64 | Me | Cl | 4-F-phenyl | H | Br |
| 5a.65 | H | Cl | 4-F-phenyl | H | $CF_3$ |
| 5a.66 | Me | Cl | 4-F-phenyl | H | $CF_3$ |
| 5a.67 | H | Br | 4-F-phenyl | H | Cl |
| 5a.68 | Me | Br | 4-F-phenyl | H | Cl |
| 5a.69 | H | Br | 4-F-phenyl | H | Br |
| 5a.70 | Me | Br | 4-F-phenyl | H | Br |
| 5a.71 | H | Br | 4-F-phenyl | H | $CF_3$ |
| 5a.72 | Me | Br | 4-F-phenyl | H | $CF_3$ |

TABLE 6a

Compounds of formula IAf (IAf)

| Compound Number | $R_1$ | $R_3$ | $R_4$ | $R_5$ | $R_6$ |
|---|---|---|---|---|---|
| 6a.1 | H | Cl | cyclopropylethynyl | H | $CF_2H$ |

TABLE 6a-continued

Compounds of formula IAf

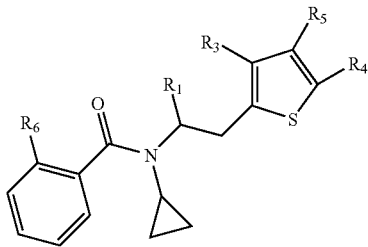

(IAf)

| Compound Number | R₁ | R₃ | R₄ | R₅ | R₆ |
|---|---|---|---|---|---|
| 6a.2 | Me | Cl | ≡─△ | H | $CF_3$ |
| 6a.3 | H | Br | ≡─△ | H | $CF_2H$ |
| 6a.4 | Me | Br | ≡─△ | H | $CF_3$ |
| 6a.5 | H | Cl | ≡─cyclopentyl | H | $CF_2H$ |
| 6a.6 | Me | Cl | ≡─cyclopentyl | H | $CF_3$ |
| 6a.7 | H | Br | ≡─cyclopentyl | H | $CF_2H$ |
| 6a.8 | Me | Br | ≡─cyclopentyl | H | $CF_3$ |
| 6a.9 | H | Cl | ≡─cyclohexyl | H | $CF_2H$ |
| 6a.10 | Me | Cl | ≡─cyclohexyl | H | $CF_3$ |
| 6a.11 | H | Br | ≡─tetrahydropyranyl | H | $CF_2H$ |
| 6a.12 | Me | Br | ≡─cyclohexyl | H | $CF_3$ |
| 6a.13 | H | Cl | ≡─Ph | H | $CF_2H$ |
| 6a.14 | Me | Cl | ≡─Ph | H | $CF_3$ |

TABLE 6a-continued

Compounds of formula IAf

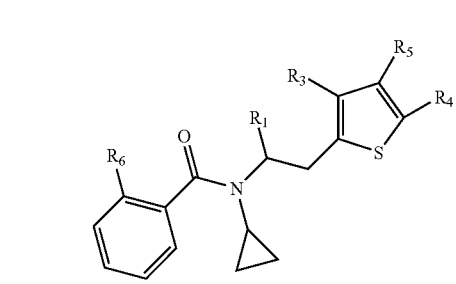

(IAf)

| Compound Number | R₁ | R₃ | R₄ | R₅ | R₆ |
|---|---|---|---|---|---|
| 6a.15 | H | Br | ≡─Ph | H | $CF_2H$ |
| 6a.16 | Me | Br | ≡─Ph | H | $CF_3$ |
| 6a.17 | H | Cl | ─C₆H₄─Cl (4-) | H | $CF_2H$ |
| 6a.18 | Me | Cl | ─C₆H₄─Cl (4-) | H | $CF_3$ |
| 6a.19 | H | Br | ─C₆H₄─Cl (4-) | H | $CF_2H$ |
| 6a.20 | Me | Br | ─C₆H₄─Cl (4-) | H | $CF_3$ |
| 6a.21 | H | Cl | ─C₆H₄─F (4-) | H | $CF_2H$ |
| 6a.22 | Me | Cl | ─C₆H₄─F (4-) | H | $CF_3$ |
| 6a.23 | H | Br | ─C₆H₄─F (4-) | H | $CF_2H$ |
| 6a.24 | Me | Br | ─C₆H₄─F (4-) | H | $CF_3$ |

TABLE 7a

Compounds of formula IAg

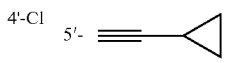
(IAg)

| Compound Number | R₁ | R₃ | R₄ | | R₅ | R₆ | R₇ | R₈ |
|---|---|---|---|---|---|---|---|---|
| 7a.1 | H | 4'-Cl | 5'- 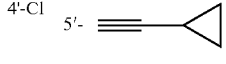 | | 2'-Cl | Me | Me | F |
| 7a.2 | Me | 4'-Cl | 5'- 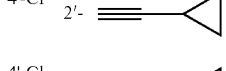 | | 2'-Cl | Me | Me | F |
| 7a.3 | H | 4'-Cl | 2'- 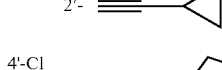 | | 5'-Cl | Me | Me | F |
| 7a.4 | Me | 4'-Cl | 2'- 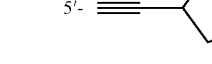 | | 5'-Cl | Me | Me | F |
| 7a.5 | H | 4'-Cl | 5'- 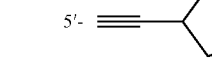 | | 2'-Cl | Me | Me | F |
| 7a.6 | Me | 4'-Cl | 5'- 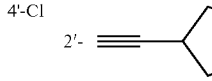 | | 2'-Cl | Me | Me | F |
| 7a.7 | H | 4'-Cl | 2'- 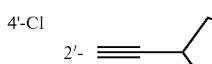 | | 5'-Cl | Me | Me | F |
| 7a.8 | Me | 4'-Cl | 2'-  | | 5'-Cl | Me | Me | F |
| 7a.9 | H | 4'-Cl | 5'-  | | 2'-Cl | Me | Me | F |
| 7a.10 | Me | 4'-Cl | 5'- 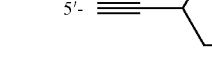 | | 2'-Cl | Me | Me | F |
| 7a.11 | H | 4'-Cl | 2'- 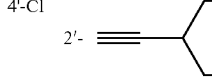 | | 5'-Cl | Me | Me | F |
| 7a.12 | Me | 4'-Cl | 2'- 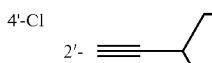 | | 5'-Cl | Me | Me | F |
| 7a.13 | H | 4'-Cl | 5'- 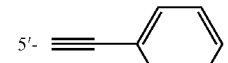 | | 2'-Cl | Me | Me | F |
| 7a.14 | Me | 4'-Cl | 5'-  | | 2'-Cl | Me | Me | F |
| 7a.15 | H | 4'-Cl | 2'-  | | 5'-Cl | Me | Me | F |
| 7a.16 | Me | 4'-Cl | 2'-  | | 5'-Cl | Me | Me | F |
| 7a.17 | H | 4'-Cl | 5'- 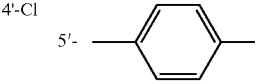 | | 2'-Cl | Me | Me | F |
| 7a.18 | Me | 4'-Cl | 5'- 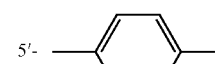 | | 2'-Cl | Me | Me | F |
| 7a.19 | H | 4'-Cl | 2'- 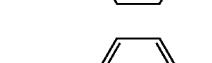 | | 5'-Cl | Me | Me | F |
| 7a.20 | Me | 4'-Cl | 2'- 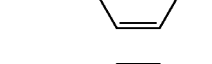 | | 5'-Cl | Me | Me | F |
| 7a.21 | H | 4'-Cl | 5'- 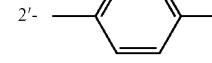 | | 2'-Cl | Me | Me | F |
| 7a.22 | Me | 4'-Cl | 5'- 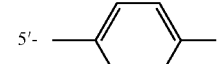 | | 2'-Cl | Me | Me | F |
| 7a.23 | H | 4'-Cl | 2'- 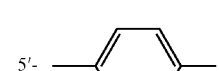 | | 5'-Cl | Me | Me | F |
| 7a.24 | Me | 4'-Cl | 2'- | | 5'-Cl | Me | Me | F |

TABLE 7a-continued

Compounds of formula IAg

(IAg)

| Compound Number | R₁ | R₃ | R₄ | | R₅ | R₆ | R₇ | R₈ |
|---|---|---|---|---|---|---|---|---|
| 7a.25 | H | 4'-Cl | 5'-  | | 2'-Cl | CF₂H | Me | H |
| 7a.26 | Me | 4'-Cl | 5'-  | | 2'-Cl | CF₂H | Me | H |
| 7a.27 | H | 4'-Cl | 2'-  | | 5'-Cl | CF₂H | Me | H |
| 7a.28 | Me | 4'-Cl | 2'-  | | 5'-Cl | CF₂H | Me | H |
| 7a.29 | H | 4'-Cl | 5'-  | | 2'-Cl | CF₂H | Me | H |
| 7a.30 | Me | 4'-Cl | 5'-  | | 2'-Cl | CF₂H | Me | H |
| 7a.31 | H | 4'-Cl | 2'-  | | 5'-Cl | CF₂H | Me | H |
| 7a.32 | Me | 4'-Cl | 2'-  | | 5'-Cl | CF₂H | Me | H |
| 7a.33 | H | 4'-Cl | 5'-  | | 2'-Cl | CF₂H | Me | H |
| 7a.34 | Me | 4'-Cl | 5'-  | | 2'-Cl | CF₂H | Me | H |
| 7a.35 | H | 4'-Cl | 2'-  | | 5'-Cl | CF₂H | Me | H |
| 7a.36 | Me | 4'-Cl | 2'- 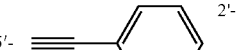 | | 5'-Cl | CF₂H | Me | H |
| 7a.37 | H | 4'-Cl | 5'-  | | 2'-Cl | CF₂H | Me | H |
| 7a.38 | Me | 4'-Cl | 5'-  | | 2'-Cl | CF₂H | Me | H |
| 7a.39 | H | 4'-Cl | 2'-  | | 5'-Cl | CF₂H | Me | H |
| 7a.40 | Me | 4'-Cl | 2'- 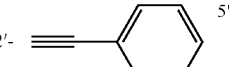 | | 5'-Cl | CF₂H | Me | H |
| 7a.41 | H | 4'-Cl | 5'- 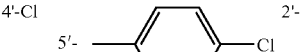 | | 2'-Cl | CF₂H | Me | H |
| 7a.42 | Me | 4'-Cl | 5'-  | | 2'-Cl | CF₂H | Me | H |
| 7a.43 | H | 4'-Cl | 2'- 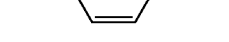 | | 5'-Cl | CF₂H | Me | H |
| 7a.44 | Me | 4'-Cl | 2'-  | | 5'-Cl | CF₂H | Me | H |
| 7a.45 | H | 4'-Cl | 5'-  | | 2'-Cl | CF₂H | Me | H |
| 7a.46 | Me | 4'-Cl | 5'- 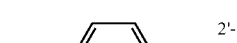 | | 2'-Cl | CF₂H | Me | H |
| 7a.47 | H | 4'-Cl | 2'- | | 5'-Cl | CF₂H | Me | H |

TABLE 7a-continued

Compounds of formula IAg (IAg)

| Compound Number | R₁ | R₃ | R₄ | R₅ | R₆ | R₇ | R₈ |
|---|---|---|---|---|---|---|---|
| 7a.48 | Me | 4'-Cl | 2'- —⟨C₆H₄⟩—F | 5'-Cl | CF₂H | Me | H |
| 7a.49 | H | 4'-Cl | 5'- —≡—cyclopropyl | 2'-Cl | CF₃ | Me | H |
| 7a.50 | Me | 4'-Cl | 5'- —≡—cyclopropyl | 2'-Cl | CF₃ | Me | H |
| 7a.51 | H | 4'-Cl | 2'- —≡—cyclopropyl | 5'-Cl | CF₃ | Me | H |
| 7a.52 | Me | 4'-Cl | 2'- —≡—cyclopropyl | 5'-Cl | CF₃ | Me | H |
| 7a.53 | H | 4'-Cl | 5'- —≡—cyclopentyl | 2'-Cl | CF₃ | Me | H |
| 7a.54 | Me | 4'-Cl | 5'- —≡—cyclopentyl | 2'-Cl | CF₃ | Me | H |
| 7a.55 | H | 4'-Cl | 2'- —≡—cyclopentyl | 5'-Cl | CF₃ | Me | H |
| 7a.56 | Me | 4'-Cl | 2'- —≡—cyclopentyl | 5'-Cl | CF₃ | Me | H |
| 7a.57 | H | 4'-Cl | 5'- —≡—cyclohexyl | 2'-Cl | CF₃ | Me | H |
| 7a.58 | Me | 4'-Cl | 5'- —≡—cyclohexyl | 2'-Cl | CF₃ | Me | H |
| 7a.59 | H | 4'-Cl | 2'- —≡—cyclohexyl | 5'-Cl | CF₃ | Me | H |
| 7a.60 | Me | 4'-Cl | 2'- —≡—cyclohexyl | 5'-Cl | CF₃ | Me | H |
| 7a.61 | H | 4'-Cl | 5'- —≡—phenyl | 2'-Cl | CF₃ | Me | H |
| 7a.62 | Me | 4'-Cl | 5'- —≡—phenyl | 2'-Cl | CF₃ | Me | H |
| 7a.63 | H | 4'-Cl | 2'- —≡—phenyl | 5'-Cl | CF₃ | Me | H |
| 7a.64 | Me | 4'-Cl | 2'- —≡—phenyl | 5'-Cl | CF₃ | Me | H |
| 7a.65 | H | 4'-Cl | 5'- —⟨C₆H₄⟩—Cl | 2'-Cl | CF₃ | Me | H |
| 7a.66 | Me | 4'-Cl | 5'- —⟨C₆H₄⟩—Cl | 2'-Cl | CF₃ | Me | H |
| 7a.67 | H | 4'-Cl | 2'- —⟨C₆H₄⟩—Cl | 5'-Cl | CF₃ | Me | H |
| 7a.68 | Me | 4'-Cl | 2'- —⟨C₆H₄⟩—Cl | 5'-Cl | CF₃ | Me | H |
| 7a.69 | H | 4'-Cl | 5'- —⟨C₆H₄⟩—F | 2'-Cl | CF₃ | Me | H |
| 7a.70 | Me | 4'-Cl | 5'- —⟨C₆H₄⟩—F | 2'-Cl | CF₃ | Me | H |

TABLE 7a-continued

Compounds of formula IAg

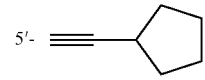

(IAg)

| Compound Number | R₁ | R₃ | R₄ | R₅ | R₆ | R₇ | R₈ |
|---|---|---|---|---|---|---|---|
| 7a.71 | H | 4'-Cl | 2'- —⟨ ⟩—F | 5'-Cl | CF₃ | Me | H |
| 7a.72 | Me | 4'-Cl | 2'- —⟨ ⟩—F | 5'-Cl | CF₃ | Me | H |

TABLE 8a

Compound of formula IAh

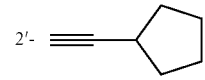

(IAh)

| Compound Number | R₁ | R₃ | R₄ | R₅ | R₆ | R₇ |
|---|---|---|---|---|---|---|
| 8a.1 | H | 4'-Cl | 5'- ≡—▷ | 2'-Cl | CF₂H | Me |
| 8a.2 | Me | 4'-Cl | 5'- ≡—▷ | 2'-Cl | CF₂H | Me |
| 8a.3 | H | 4'-Cl | 2'- ≡—▷ | 5'-Cl | CF₂H | Me |
| 8a.4 | Me | 4'-Cl | 2'- ≡—▷ | 5'-Cl | CF₂H | Me |
| 8a.5 | H | 4'-Cl | 5'- ≡—cyclopentyl | 2'-Cl | CF₂H | Me |
| 8a.6 | Me | 4'-Cl | 5'- ≡—cyclopentyl | 2'-Cl | CF₂H | Me |
| 8a.7 | H | 4'-Cl | 2'- ≡—cyclopentyl | 5'-Cl | CF₂H | Me |
| 8a.8 | Me | 4'-Cl | 2'- ≡—cyclopentyl | 5'-Cl | CF₂H | Me |
| 8a.9 | H | 4'-Cl | 5'- ≡—cyclohexyl | 2'-Cl | CF₂H | Me |
| 8a.10 | Me | 4'-Cl | 5'- ≡—cyclohexyl | 2'-Cl | CF₂H | Me |
| 8a.11 | H | 4'-Cl | 2'- ≡—cyclohexyl | 5'-Cl | CF₂H | Me |
| 8a.12 | Me | 4'-Cl | 2'- ≡—cyclohexyl | 5'-Cl | CF₂H | Me |
| 8a.13 | H | 4'-Cl | 5'- ≡—Ph | 2'-Cl | CF₂H | Me |
| 8a.14 | Me | 4'-Cl | 5'- ≡—Ph | 2'-Cl | CF₂H | Me |
| 8a.15 | H | 4'-Cl | 2'- ≡—Ph | 5'-Cl | CF₂H | Me |
| 8a.16 | Me | 4'-Cl | 2'- ≡—Ph | 5'-Cl | CF₂H | Me |
| 8a.17 | H | 4'-Cl | 5'- —⟨ ⟩—Cl | 2'-Cl | CF₂H | Me |

TABLE 8a-continued

Compound of formula IAh (IAh)

| Compound Number | R₁ | R₃ | R₄ | | R₅ | R₆ | R₇ |
|---|---|---|---|---|---|---|---|
| 8a.18 | Me | 4'-Cl | 5'- —⟨4-Cl-C₆H₄⟩ | | 2'-Cl | CF₂H | Me |
| 8a.19 | H | 4'-Cl | 2'- —⟨4-Cl-C₆H₄⟩ | | 5'-Cl | CF₂H | Me |
| 8a.20 | Me | 4'-Cl | 2'- —⟨4-Cl-C₆H₄⟩ | | 5'-Cl | CF₂H | Me |
| 8a.21 | H | 4'-Cl | 5'- —⟨4-F-C₆H₄⟩ | | 2'-Cl | CF₂H | Me |
| 8a.22 | Me | 4'-Cl | 5'- —⟨4-F-C₆H₄⟩ | | 2'-Cl | CF₂H | Me |
| 8a.23 | H | 4'-Cl | 2'- —⟨4-F-C₆H₄⟩ | | 5'-Cl | CF₂H | Me |
| 8a.24 | Me | 4'-Cl | 2'- —⟨4-F-C₆H₄⟩ | | 5'-Cl | CF₂H | Me |
| 8a.25 | H | 4'-Cl | 5'- —≡—cPr | | 2'-Cl | CF₃ | Me |
| 8a.26 | Me | 4'-Cl | 5'- —≡—cPr | | 2'-Cl | CF₃ | Me |
| 8a.27 | H | 4'-Cl | 2'- —≡—cPr | | 5'-Cl | CF₃ | Me |
| 8a.28 | Me | 4'-Cl | 2'- —≡—cPr | | 5'-Cl | CF₃ | Me |
| 8a.29 | H | 4'-Cl | 5'- —≡—cPent | | 2'-Cl | CF₃ | Me |
| 8a.30 | Me | 4'-Cl | 5'- —≡—cPent | | 2'-Cl | CF₃ | Me |
| 8a.31 | H | 4'-Cl | 2'- —≡—cPent | | 5'-Cl | CF₃ | Me |
| 8a.32 | Me | 4'-Cl | 2'- —≡—cPent | | 5'-Cl | CF₃ | Me |
| 8a.33 | H | 4'-Cl | 5'- —≡—cHex | | 2'-Cl | CF₃ | Me |
| 8a.34 | Me | 4'-Cl | 5'- —≡—cHex | | 2'-Cl | CF₃ | Me |
| 8a.35 | H | 4'-Cl | 2'- —≡—cHex | | 5'-Cl | CF₃ | Me |
| 8a.36 | Me | 4'-Cl | 2'- —≡—cHex | | 5'-Cl | CF₃ | Me |
| 8a.37 | H | 4'-Cl | 5'- —≡—Ph | | 2'-Cl | CF₃ | Me |
| 8a.38 | Me | 4'-Cl | 5'- —≡—Ph | | 2'-Cl | CF₃ | Me |
| 8a.39 | H | 4'-Cl | 2'- —≡—Ph | | 5'-Cl | CF₃ | Me |
| 8a.40 | Me | 4'-Cl | 2'- —≡—Ph | | 5'-Cl | CF₃ | Me |
| 8a.41 | H | 4'-Cl | 5'- —⟨4-Cl-C₆H₄⟩ | | 2'-Cl | CF₃ | Me |
| 8a.42 | Me | 4'-Cl | 5'- —⟨4-Cl-C₆H₄⟩ | | 2'-Cl | CF₃ | Me |

TABLE 8a-continued

Compound of formula IAh

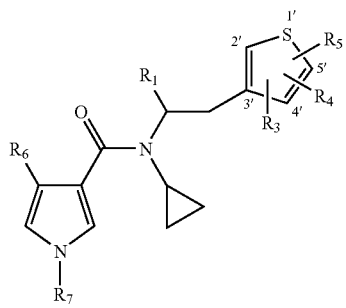
(IAh)

| Compound Number | R₁ | R₃ | R₄ | | R₅ | R₆ | R₇ |
|---|---|---|---|---|---|---|---|
| 8a.43 | H | 4'-Cl | 2'- ⟨C₆H₄⟩-Cl (para) 5'- | | 5'-Cl | CF₃ | Me |
| 8a.44 | Me | 4'-Cl | 2'- ⟨C₆H₄⟩-Cl (para) 5'- | | 5'-Cl | CF₃ | Me |
| 8a.45 | H | 4'-Cl | 5'- ⟨C₆H₄⟩-F (para) | | 2'-Cl | CF₃ | Me |
| 8a.46 | Me | 4'-Cl | 5'- ⟨C₆H₄⟩-F (para) | | 2'-Cl | CF₃ | Me |
| 8a.47 | H | 4'-Cl | 5'- ⟨C₆H₄⟩-F (para) | | 5'-Cl | CF₃ | Me |
| 8a.48 | Me | 4'-Cl | 2'- ⟨C₆H₄⟩-F (para) 5'- | | 5'-Cl | CF₃ | Me |

TABLE 9a

Compounds of Formula IAi

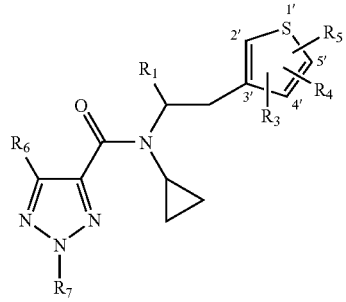
(IAi)

| Compound Number | R₁ | R₃ | R₄ | | R₅ | R₆ | R₇ |
|---|---|---|---|---|---|---|---|
| 9a.1 | H | 4'-Cl | 5'- ≡—⟨cyclopropyl⟩ | | 2'-Cl | CF₂H | Me |

TABLE 9a-continued

Compounds of Formula IAi

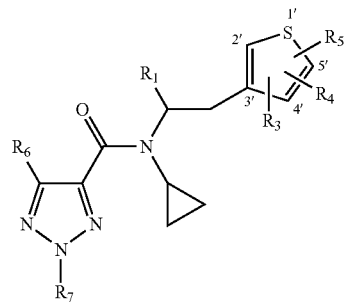
(IAi)

| Compound Number | R₁ | R₃ | R₄ | | R₅ | R₆ | R₇ |
|---|---|---|---|---|---|---|---|
| 9a.2 | Me | 4'-Cl | 5'- ≡—⟨cyclopropyl⟩ | | 2'-Cl | CF₂H | Me |
| 9a.3 | H | 4'-Cl | 2'- ≡—⟨cyclopropyl⟩ | | 5'-Cl | CF₂H | Me |
| 9a.4 | Me | 4'-Cl | 2'- ≡—⟨cyclopropyl⟩ | | 5'-Cl | CF₂H | Me |
| 9a.5 | H | 4'-Cl | 5'- ≡—⟨cyclopentyl⟩ | | 2'-Cl | CF₂H | Me |
| 9a.6 | Me | 4'-Cl | 5'- ≡—⟨cyclopentyl⟩ | | 2'-Cl | CF₂H | Me |
| 9a.7 | H | 4'-Cl | 2'- ≡—⟨cyclopentyl⟩ | | 5'-Cl | CF₂H | Me |
| 9a.8 | Me | 4'-Cl | 2'- ≡—⟨cyclopentyl⟩ | | 5'-Cl | CF₂H | Me |
| 9a.9 | H | 4'-Cl | 5'- ≡—⟨cyclohexyl⟩ | | 2'-Cl | CF₂H | Me |
| 9a.10 | Me | 4'-Cl | 5'- ≡—⟨cyclohexyl⟩ | | 2'-Cl | CF₂H | Me |
| 9a.11 | H | 4'-Cl | 2'- ≡—⟨cyclohexyl⟩ | | 5'-Cl | CF₂H | Me |
| 9a.12 | Me | 4'-Cl | 2'- ≡—⟨cyclohexyl⟩ | | 5'-Cl | CF₂H | Me |
| 9a.13 | H | 4'-Cl | 5'- ≡—⟨phenyl⟩ | | 2'-Cl | CF₂H | Me |
| 9a.14 | Me | 4'-Cl | 5'- ≡—⟨phenyl⟩ | | 2'-Cl | CF₂H | Me |

TABLE 9a-continued

Compounds of Formula IAi (IAi)

| Compound Number | R₁ | R₃ | R₄ | R₅ | R₆ | R₇ |
|---|---|---|---|---|---|---|
| 9a.15 | H | 4'-Cl | 2'- ethynylphenyl | 5'-Cl | CF₂H | Me |
| 9a.16 | Me | 4'-Cl | 2'- ethynylphenyl | 5'-Cl | CF₂H | Me |
| 9a.17 | H | 4'-Cl | 5'- (4-Cl-phenyl) | 2'-Cl | CF₂H | Me |
| 9a.18 | Me | 4'-Cl | 5'- (4-Cl-phenyl) | 2'-Cl | CF₂H | Me |
| 9a.19 | H | 4'-Cl | 2'- (4-Cl-phenyl) | 5'-Cl | CF₂H | Me |
| 9a.20 | Me | 4'-Cl | 2'- (4-Cl-phenyl) | 5'-Cl | CF₂H | Me |
| 9a.21 | H | 4'-Cl | 5'- (4-F-phenyl) | 2'-Cl | CF₂H | Me |
| 9a.22 | Me | 4'-Cl | 5'- (4-F-phenyl) | 2'-Cl | CF₂H | Me |
| 9a.23 | H | 4'-Cl | 2'- (4-F-phenyl) | 5'-Cl | CF₂H | Me |
| 9a.24 | Me | 4'-Cl | 2'- (4-F-phenyl) | 5'-Cl | CF₂H | Me |
| 9a.25 | H | 4'-Cl | 5'- ethynylcyclopropyl | 2'-Cl | CF₃ | Me |
| 9a.26 | Me | 4'-Cl | 5'- ethynylcyclopropyl | 2'-Cl | CF₃ | Me |
| 9a.27 | H | 4'-Cl | 2'- ethynylcyclopropyl | 5'-Cl | CF₃ | Me |
| 9a.28 | Me | 4'-Cl | 2'- ethynylcyclopropyl | 5'-Cl | CF₃ | Me |
| 9a.29 | H | 4'-Cl | 5'- ethynylcyclopentyl | 2'-Cl | CF₃ | Me |
| 9a.30 | Me | 4'-Cl | 5'- ethynylcyclopentyl | 2'-Cl | CF₃ | Me |
| 9a.31 | H | 4'-Cl | 2'- ethynylcyclopentyl | 5'-Cl | CF₃ | Me |
| 9a.32 | Me | 4'-Cl | 2'- ethynylcyclopentyl | 5'-Cl | CF₃ | Me |
| 9a.33 | H | 4'-Cl | 5'- ethynylcyclohexyl | 2'-Cl | CF₃ | Me |
| 9a.34 | Me | 4'-Cl | 5'- ethynylcyclohexyl | 2'-Cl | CF₃ | Me |
| 9a.35 | H | 4'-Cl | 2'- ethynylcyclohexyl | 5'-Cl | CF₃ | Me |
| 9a.36 | Me | 4'-Cl | 2'- ethynylcyclohexyl | 5'-Cl | CF₃ | Me |
| 9a.37 | H | 4'-Cl | 5'- ethynylphenyl | 2'-Cl | CF₃ | Me |
| 9a.38 | Me | 4'-Cl | 5'- ethynylphenyl | 2'-Cl | CF₃ | Me |

TABLE 9a-continued

Compounds of Formula IAi (IAi)

| Compound Number | $R_1$ | $R_3$ | $R_4$ | $R_5$ | $R_6$ | $R_7$ |
|---|---|---|---|---|---|---|
| 9a.39 | H | 4'-Cl | 2'-ethynylphenyl | 5'-Cl | $CF_3$ | Me |
| 9a.40 | Me | 4'-Cl | 2'-ethynylphenyl | 5'-Cl | $CF_3$ | Me |
| 9a.41 | H | 4'-Cl | 5'-(4-chlorophenyl) | 2'-Cl | $CF_3$ | Me |
| 9a.42 | Me | 4'-Cl | 5'-(4-chlorophenyl) | 2'-Cl | $CF_3$ | Me |
| 9a.43 | H | 4'-Cl | 2'-(4-chlorophenyl) | 5'-Cl | $CF_3$ | Me |
| 9a.44 | Me | 4'-Cl | 2'-(4-chlorophenyl) | 5'-Cl | $CF_3$ | Me |
| 9a.45 | H | 4'-Cl | 5'-(4-fluorophenyl) | 2'-Cl | $CF_3$ | Me |
| 9a.46 | Me | 4'-Cl | 5'-(4-fluorophenyl) | 2'-Cl | $CF_3$ | Me |
| 9a.47 | H | 4'-Cl | 2'-(4-fluorophenyl) | 5'-Cl | $CF_3$ | Me |
| 9a.48 | Me | 4'-Cl | 2'-(4-fluorophenyl) | 5'-Cl | $CF_3$ | Me |

TABLE 10a

Compounds of formula IAj (IAj)

| Compound Number | $R_1$ | $R_3$ | $R_4$ | $R_5$ | $R_6$ | $R_7$ |
|---|---|---|---|---|---|---|
| 10a.1 | H | 4'-Cl | 5'-(cyclopropylethynyl) | 2'-Cl | $CF_2H$ | Me |
| 10a.2 | Me | 4'-Cl | 5'-(cyclopropylethynyl) | 2'-Cl | $CF_2H$ | Me |
| 10a.3 | H | 4'-Cl | 2'-(cyclopropylethynyl) | 5'-Cl | $CF_2H$ | Me |
| 10a.4 | Me | 4'-Cl | 2'-(cyclopropylethynyl) | 5'-Cl | $CF_2H$ | Me |
| 10a.5 | H | 4'-Cl | 5'-(cyclopentylethynyl) | 2'-Cl | $CF_2H$ | Me |
| 10a.6 | Me | 4'-Cl | 5'-(cyclopentylethynyl) | 2'-Cl | $CF_2H$ | Me |
| 10a.7 | H | 4'-Cl | 2'-(cyclopentylethynyl) | 5'-Cl | $CF_2H$ | Me |
| 10a.8 | Me | 4'-Cl | 2'-(cyclopentylethynyl) | 5'-Cl | $CF_2H$ | Me |
| 10a.9 | H | 4'-Cl | 5'-(cyclohexylethynyl) | 2'-Cl | $CF_2H$ | Me |
| 10a.10 | Me | 4'-Cl | 5'-(cyclohexylethynyl) | 2'-Cl | $CF_2H$ | Me |
| 10a.11 | H | 4'-Cl | 2'-(cyclohexylethynyl) | 5'-Cl | $CF_2H$ | Me |
| 10a.12 | Me | 4'-Cl | 2'-(cyclohexylethynyl) | 5'-Cl | $CF_2H$ | Me |
| 10a.13 | H | 4'-Cl | 5'-(phenylethynyl) | 2'-Cl | $CF_2H$ | Me |

TABLE 10a-continued

Compounds of formula IAj (IAj)

| Compound Number | R$_1$ | R$_3$ | R$_4$ | R$_5$ | R$_6$ | R$_7$ |
|---|---|---|---|---|---|---|
| 10a.14 | Me | 4'-Cl | 5'- —≡—phenyl | 2'-Cl | CF$_2$H | Me |
| 10a.15 | H | 4'-Cl | 2'- —≡—phenyl | 5'-Cl | CF$_2$H | Me |
| 10a.16 | Me | 4'-Cl | 2'- —≡—phenyl | 5'-Cl | CF$_2$H | Me |
| 10a.17 | H | 4'-Cl | 5'- —(4-Cl-phenyl) | 2'-Cl | CF$_2$H | Me |
| 10a.18 | Me | 4'-Cl | 5'- —(4-Cl-phenyl) | 2'-Cl | CF$_2$H | Me |
| 10a.19 | H | 4'-Cl | 2'- —(4-Cl-phenyl) | 5'-Cl | CF$_2$H | Me |
| 10a.20 | Me | 4'-Cl | 2'- —(4-Cl-phenyl) | 5'-Cl | CF$_2$H | Me |
| 10a.21 | H | 4'-Cl | 5'- —(4-F-phenyl) | 2'-Cl | CF$_2$H | Me |
| 10a.22 | Me | 4'-Cl | 5'- —(4-F-phenyl) | 2'-Cl | CF$_2$H | Me |
| 10a.23 | H | 4'-Cl | 2'- —(4-F-phenyl) | 5'-Cl | CF$_2$H | Me |
| 10a.24 | Me | 4'-Cl | 2'- —(4-F-phenyl) | 5'-Cl | CF$_2$H | Me |
| 10a.25 | H | 4'-Cl | 5'- —≡—cyclopropyl | 2'-Cl | CF$_3$ | Me |
| 10a.26 | Me | 4'-Cl | 5'- —≡—cyclopropyl | 2'-Cl | CF$_3$ | Me |
| 10a.27 | H | 4'-Cl | 2'- —≡—cyclopropyl | 5'-Cl | CF$_3$ | Me |
| 10a.28 | Me | 4'-Cl | 2'- —≡—cyclopropyl | 5'-Cl | CF$_3$ | Me |
| 10a.29 | H | 4'-Cl | 5'- —≡—cyclopentyl | 2'-Cl | CF$_3$ | Me |
| 10a.30 | Me | 4'-Cl | 5'- —≡—cyclopentyl | 2'-Cl | CF$_3$ | Me |
| 10a.31 | H | 4'-Cl | 2'- —≡—cyclopentyl | 5'-Cl | CF$_3$ | Me |
| 10a.32 | Me | 4'-Cl | 2'- —≡—cyclopentyl | 5'-Cl | CF$_3$ | Me |
| 10a.33 | H | 4'-Cl | 5'- —≡—cyclohexyl | 2'-Cl | CF$_3$ | Me |
| 10a.34 | Me | 4'-Cl | 5'- —≡—cyclohexyl | 2'-Cl | CF$_3$ | Me |
| 10a.35 | H | 4'-Cl | 2'- —≡—cyclohexyl | 5'-Cl | CF$_3$ | Me |
| 10a.36 | Me | 4'-Cl | 2'- —≡—cyclohexyl | 5'-Cl | CF$_3$ | Me |
| 10a.37 | H | 4'-Cl | 5'- —≡—phenyl | 2'-Cl | CF$_3$ | Me |

TABLE 10a-continued

Compounds of formula IAj

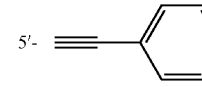

(IAj)

| Compound Number | R₁ | R₃ | R₄ | R₅ | R₆ | R₇ |
|---|---|---|---|---|---|---|
| 10a.38 | Me | 4'-Cl | 5'-ethynyl-phenyl | 2'-Cl | CF₃ | Me |
| 10a.39 | H | 4'-Cl | 2'-ethynyl-phenyl | 5'-Cl | CF₃ | Me |
| 10a.40 | Me | 4'-Cl | 2'-ethynyl-phenyl | 5'-Cl | CF₃ | Me |
| 10a.41 | H | 4'-Cl | 5'-(4-Cl-phenyl) | 2'-Cl | CF₃ | Me |
| 10a.42 | Me | 4'-Cl | 5'-(4-Cl-phenyl) | 2'-Cl | CF₃ | Me |
| 10a.43 | H | 4'-Cl | 2'-(4-Cl-phenyl) | 5'-Cl | CF₃ | Me |
| 10a.44 | Me | 4'-Cl | 2'-(4-Cl-phenyl) | 5'-Cl | CF₃ | Me |
| 10a.45 | H | 4'-Cl | 5'-(4-F-phenyl) | 2'-Cl | CF₃ | Me |
| 10a.46 | Me | 4'-Cl | 5'-(4-F-phenyl) | 2'-Cl | CF₃ | Me |
| 10a.47 | H | 4'-Cl | 2'-(4-F-phenyl) | 5'-Cl | CF₃ | Me |
| 10a.48 | Me | 4'-Cl | 2'-(4-F-phenyl) | 5'-Cl | CF₃ | Me |

TABLE 11a

Compounds of formula IAk

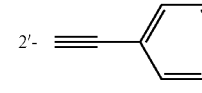

(IAk)

| Compound Number | R₁ | R₃ | R₄ | R₅ | R₆ |
|---|---|---|---|---|---|
| 11a.1 | H | 4'-Cl | 5'-ethynyl-cyclopropyl | 2'-Cl | Cl |
| 11a.2 | Me | 4'-Cl | 5'-ethynyl-cyclopropyl | 2'-Cl | Cl |
| 11a.3 | H | 4'-Cl | 2'-ethynyl-cyclopropyl | 5'-Cl | Cl |
| 11a.4 | Me | 4'-Cl | 2'-ethynyl-cyclopropyl | 5'-Cl | Cl |
| 11a.5 | H | 4'-Cl | 5'-ethynyl-cyclopropyl | 2'-Cl | Br |
| 11a.6 | Me | 4'-Cl | 5'-ethynyl-cyclopropyl | 2'-Cl | Br |
| 11a.7 | H | 4'-Cl | 2'-ethynyl-cyclopropyl | 5'-Cl | Br |
| 11a.8 | Me | 4'-Cl | 2'-ethynyl-cyclopropyl | 5'-Cl | Br |
| 11a.9 | H | 4'-Cl | 5'-ethynyl-cyclopropyl | 2'-Cl | CF₃ |
| 11a.10 | Me | 4'-Cl | 5'-ethynyl-cyclopropyl | 2'-Cl | CF₃ |
| 11a.11 | H | 4'-Cl | 2'-ethynyl-cyclopropyl | 5'-Cl | CF₃ |
| 11a.12 | Me | 4'-Cl | 2'-ethynyl-cyclopropyl | 5'-Cl | CF₃ |
| 11a.13 | H | 4'-Cl | 5'-ethynyl-cyclopentyl | 2'-Cl | Cl |
| 11a.14 | Me | 4'-Cl | 5'-ethynyl-cyclopentyl | 2'-Cl | Cl |
| 11a.15 | H | 4'-Cl | 2'-ethynyl-cyclopentyl | 5'-Cl | Cl |
| 11a.16 | Me | 4'-Cl | 2'-ethynyl-cyclopentyl | 5'-Cl | Cl |

TABLE 11a-continued

Compounds of formula IAk (IAk, structure with pyridine-carboxamide, N-cyclopropyl, R₁, thiophene bearing R₃, R₄, R₅, and R₆ on pyridine)

| Compound Number | R₁ | R₃ | R₄ | R₅ | R₆ |
|---|---|---|---|---|---|
| 11a.17 | H | 4'-Cl | 5'- ethynyl-cyclopentyl | 2'-Cl | Br |
| 11a.18 | Me | 4'-Cl | 5'- ethynyl-cyclopentyl | 2'-Cl | Br |
| 11a.19 | H | 4'-Cl | 2'- ethynyl-cyclopentyl | 5'-Cl | Br |
| 11a.20 | Me | 4'-Cl | 2'- ethynyl-cyclopentyl | 5'-Cl | Br |
| 11a.21 | H | 4'-Cl | 5'- ethynyl-cyclopentyl | 2'-Cl | CF₃ |
| 11a.22 | Me | 4'-Cl | 5'- ethynyl-cyclopentyl | 2'-Cl | CF₃ |
| 11a.23 | H | 4'-Cl | 2'- ethynyl-cyclopentyl | 5'-Cl | CF₃ |
| 11a.24 | Me | 4'-Cl | 2'- ethynyl-cyclopentyl | 5'-Cl | CF₃ |
| 11a.25 | H | 4'-Cl | 5'- ethynyl-cyclohexyl | 2'-Cl | Cl |
| 11a.26 | Me | 4'-Cl | 5'- ethynyl-cyclohexyl | 2'-Cl | Cl |
| 11a.27 | H | 4'-Cl | 2'- ethynyl-cyclohexyl | 5'-Cl | Cl |
| 11a.28 | Me | 4'-Cl | 2'- ethynyl-cyclohexyl | 5'-Cl | Cl |
| 11a.29 | H | 4'-Cl | 5'- ethynyl-cyclohexyl | 2'-Cl | Br |
| 11a.30 | Me | 4'-Cl | 5'- ethynyl-cyclohexyl | 2'-Cl | Br |
| 11a.31 | H | 4'-Cl | 2'- ethynyl-cyclohexyl | 5'-Cl | Br |
| 11a.32 | Me | 4'-Cl | 2'- ethynyl-cyclohexyl | 5'-Cl | Br |
| 11a.33 | H | 4'-Cl | 5'- ethynyl-cyclohexyl | 2'-Cl | CF₃ |
| 11a.34 | Me | 4'-Cl | 5'- ethynyl-cyclohexyl | 2'-Cl | CF₃ |
| 11a.35 | H | 4'-Cl | 2'- ethynyl-cyclohexyl | 5'-Cl | CF₃ |
| 11a.36 | Me | 4'-Cl | 2'- ethynyl-cyclohexyl | 5'-Cl | CF₃ |
| 11a.37 | H | 4'-Cl | 5'- ethynyl-phenyl | 2'-Cl | Cl |
| 11a.38 | Me | 4'-Cl | 5'- ethynyl-phenyl | 2'-Cl | Cl |
| 11a.39 | H | 4'-Cl | 2'- ethynyl-phenyl | 5'-Cl | Cl |
| 11a.40 | Me | 4'-Cl | 2'- ethynyl-phenyl | 5'-Cl | Cl |
| 11a.41 | H | 4'-Cl | 5'- ethynyl-phenyl | 2'-Cl | Br |

TABLE 11a-continued

Compounds of formula IAk (IAk)

| Compound Number | R₁ | R₃ | R₄ | R₅ | R₆ |
|---|---|---|---|---|---|
| 11a.42 | Me | 4'-Cl | 5'- —≡—phenyl | 2'-Cl | Br |
| 11a.43 | H | 4'-Cl | 2'- —≡—phenyl | 5'-Cl | Br |
| 11a.44 | Me | 4'-Cl | 2'- —≡—phenyl | 5'-Cl | Br |
| 11a.45 | H | 4'-Cl | 5'- —≡—phenyl | 2'-Cl | CF₃ |
| 11a.46 | Me | 4'-Cl | 5'- —≡—phenyl | 2'-Cl | CF₃ |
| 11a.47 | H | 4'-Cl | 2'- —≡—phenyl | 5'-Cl | CF₃ |
| 11a.48 | Me | 4'-Cl | 2'- —≡—phenyl | 5'-Cl | CF₃ |
| 11a.49 | H | 4'-Cl | 5'- —(4-Cl-phenyl) | 2'-Cl | Cl |
| 11a.50 | Me | 4'-Cl | 5'- —(4-Cl-phenyl) | 2'-Cl | Cl |
| 11a.51 | H | 4'-Cl | 2'- —(4-Cl-phenyl) | 5'-Cl | Cl |
| 11a.52 | Me | 4'-Cl | 2'- —(4-Cl-phenyl) | 5'-Cl | Cl |
| 11a.53 | H | 4'-Cl | 5'- —(4-Cl-phenyl) | 2'-Cl | Br |
| 11a.54 | Me | 4'-Cl | 5'- —(4-Cl-phenyl) | 2'-Cl | Br |
| 11a.55 | H | 4'-Cl | 2'- —(4-Cl-phenyl) | 5'-Cl | Br |
| 11a.56 | Me | 4'-Cl | 2'- —(4-Cl-phenyl) | 5'-Cl | Br |
| 11a.57 | H | 4'-Cl | 5'- —(4-Cl-phenyl) | 2'-Cl | CF₃ |
| 11a.58 | Me | 4'-Cl | 5'- —(4-Cl-phenyl) | 2'-Cl | CF₃ |
| 11a.59 | H | 4'-Cl | 2'- —(4-Cl-phenyl) | 5'-Cl | CF₃ |
| 11a.60 | Me | 4'-Cl | 2'- —(4-Cl-phenyl) | 5'-Cl | CF₃ |
| 11a.61 | H | 4'-Cl | 5'- —(4-F-phenyl) | 2'-Cl | Cl |
| 11a.62 | Me | 4'-Cl | 5'- —(4-F-phenyl) | 2'-Cl | Cl |
| 11a.63 | H | 4'-Cl | 2'- —(4-F-phenyl) | 5'-Cl | Cl |
| 11a.64 | Me | 4'-Cl | 2'- —(4-F-phenyl) | 5'-Cl | Cl |
| 11a.65 | H | 4'-Cl | 5'- —(4-F-phenyl) | 2'-Cl | Br |

TABLE 11a-continued

Compounds of formula IAk (IAk)

| Compound Number | R₁ | R₃ | R₄ | R₅ | R₆ |
|---|---|---|---|---|---|
| 11a.66 | Me | 4'-Cl | 5'- ⟨C₆H₄⟩-F | 2'-Cl | Br |
| 11a.67 | H | 4'-Cl | 2'- ⟨C₆H₄⟩-F | 5'-Cl | Br |
| 11a.68 | Me | 4'-Cl | 2'- ⟨C₆H₄⟩-F | 5'-Cl | Br |
| 11a.69 | H | 4'-Cl | 5'- ⟨C₆H₄⟩-F | 2'-Cl | $CF_3$ |
| 11a.70 | Me | 4'-Cl | 5'- ⟨C₆H₄⟩-F | 2'-Cl | $CF_3$ |
| 11a.71 | H | 4'-Cl | 2'- ⟨C₆H₄⟩-F | 5'-Cl | $CF_3$ |
| 11a.72 | Me | 4'-Cl | 2'- ⟨C₆H₄⟩-F | 5'-Cl | $CF_3$ |

TABLE 12a

Compounds of formula IIaa

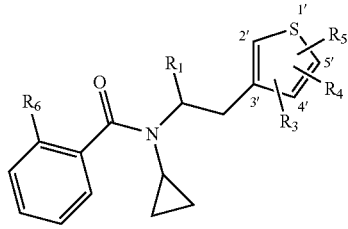

(IIaa)

| Compound Number | R₁ | R₃ | R₄ | R₅ | R₆ |
|---|---|---|---|---|---|
| 12a.1 | H | 4'-Cl | 5'- ≡⟨cyclopropyl⟩ | 2'-Cl | $CF_2H$ |
| 12a.2 | Me | 4'-Cl | 5'- ≡⟨cyclopropyl⟩ | 2'-Cl | $CF_2H$ |
| 12a.3 | H | 4'-Cl | 2'- ≡⟨cyclopropyl⟩ | 5'-Cl | $CF_2H$ |
| 12a.4 | Me | 4'-Cl | 2'- ≡⟨cyclopropyl⟩ | 5'-Cl | $CF_2H$ |
| 12a.5 | H | 4'-Cl | 5'- ≡⟨cyclopropyl⟩ | 2'-Cl | $CF_3$ |
| 12a.6 | Me | 4'-Cl | 5'- ≡⟨cyclopropyl⟩ | 2'-Cl | $CF_3$ |
| 12a.7 | H | 4'-Cl | 2'- ≡⟨cyclopropyl⟩ | 5'-Cl | $CF_3$ |
| 12a.8 | Me | 4'-Cl | 2'- ≡⟨cyclopropyl⟩ | 5'-Cl | $CF_3$ |
| 12a.9 | H | 4'-Cl | 5'- ≡⟨cyclopentyl⟩ | 2'-Cl | $CF_2H$ |
| 12a.10 | Me | 4'-Cl | 5'- ≡⟨cyclopentyl⟩ | 2'-Cl | $CF_2H$ |
| 12a.11 | H | 4'-Cl | 2'- ≡⟨cyclopentyl⟩ | 5'-Cl | $CF_2H$ |
| 12a.12 | Me | 4'-Cl | 2'- ≡⟨cyclopentyl⟩ | 5'-Cl | $CF_2H$ |
| 12a.13 | H | 4'-Cl | 5'- ≡⟨cyclopentyl⟩ | 2'-Cl | $CF_3$ |
| 12a.14 | Me | 4'-Cl | 5'- ≡⟨cyclopentyl⟩ | 2'-Cl | $CF_3$ |
| 12a.15 | H | 4'-Cl | 2'- ≡⟨cyclopentyl⟩ | 5'-Cl | $CF_3$ |
| 12a.16 | Me | 4'-Cl | 2'- ≡⟨cyclopentyl⟩ | 5'-Cl | $CF_3$ |

TABLE 12a-continued

Compounds of formula IIaa

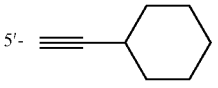
(IIaa)

| Compound Number | R₁ | R₃ | R₄ | R₅ | R₆ |
|---|---|---|---|---|---|
| 12a.17 | H | 4'-Cl | 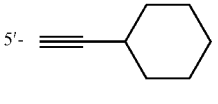 | 2'-Cl | CF₂H |
| 12a.18 | Me | 4'-Cl | 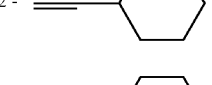 | 2'-Cl | CF₂H |
| 12a.19 | H | 4'-Cl | 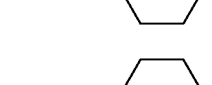 | 5'-Cl | CF₂H |
| 12a.20 | Me | 4'-Cl | 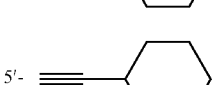 | 5'-Cl | CF₂H |
| 12a.21 | H | 4'-Cl | 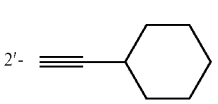 | 2'-Cl | CF₃ |
| 12a.22 | Me | 4'-Cl | 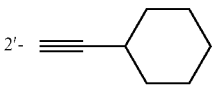 | 2'-Cl | CF₃ |
| 12a.23 | H | 4'-Cl | 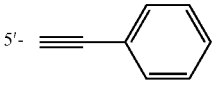 | 5'-Cl | CF₃ |
| 12a.24 | Me | 4'-Cl | 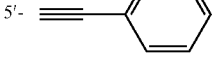 | 5'-Cl | CF₃ |
| 12a.25 | H | 4'-Cl | 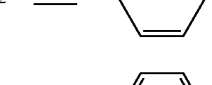 | 2'-Cl | CF₂H |
| 12a.26 | Me | 4'-Cl | 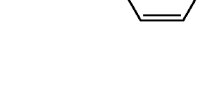 | 2'-Cl | CF₂H |
| 12a.27 | H | 4'-Cl |  | 5'-Cl | CF₂H |
| 12a.28 | Me | 4'-Cl | 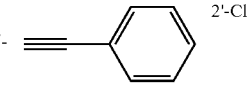 | 5'-Cl | CF₂H |

TABLE 12a-continued

Compounds of formula IIaa

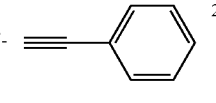
(IIaa)

| Compound Number | R₁ | R₃ | R₄ | R₅ | R₆ |
|---|---|---|---|---|---|
| 12a.29 | H | 4'-Cl | 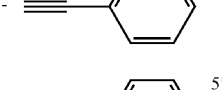 | 2'-Cl | CF₃ |
| 12a.30 | Me | 4'-Cl | 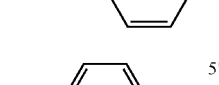 | 2'-Cl | CF₃ |
| 12a.31 | H | 4'-Cl |  | 5'-Cl | CF₃ |
| 12a.32 | Me | 4'-Cl | 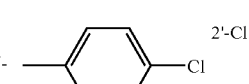 | 5'-Cl | CF₃ |
| 12a.33 | H | 4'-Cl | 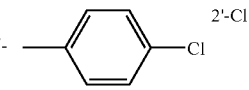 | 5'-Cl | CF₂H |
| 12a.34 | Me | 4'-Cl |  | 5'-Cl | CF₂H |
| 12a.35 | H | 4'-Cl | 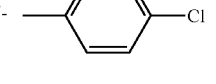 | 2'-Cl | CF₂H |
| 12a.36 | Me | 4'-Cl | 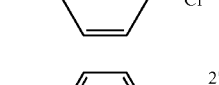 | 2'-Cl | CF₂H |
| 12a.37 | H | 4'-Cl | 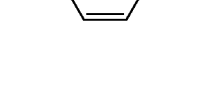 | 5'-Cl | CF₃ |
| 12a.38 | Me | 4'-Cl |  | 5'-Cl | CF₃ |
| 12a.39 | H | 4'-Cl |  | 2'-Cl | CF₃ |
| 12a.40 | Me | 4'-Cl |  | 2'-Cl | CF₃ |

TABLE 12a-continued

Compounds of formula IIaa (IIaa)

| Compound Number | R₁ | R₃ | R₄ | R₅ | R₆ |
|---|---|---|---|---|---|
| 12a.41 | H | 4'-Cl | 2'- (4-F-phenyl) | 5'-Cl | CF₂H |
| 12a.42 | Me | 4'-Cl | 2'- (4-F-phenyl) | 5'-Cl | CF₂H |
| 12a.43 | H | 4'-Cl | 5'- (4-F-phenyl) | 2'-Cl | CF₂H |
| 12a.44 | Me | 4'-Cl | 5'- (4-F-phenyl) | 2'-Cl | CF₂H |
| 12a.45 | H | 4'-Cl | 2'- (4-F-phenyl) | 5'-Cl | CF₃ |
| 12a.46 | Me | 4'-Cl | 2'- (4-F-phenyl) | 5'-Cl | CF₃ |
| 12a.47 | H | 4'-Cl | 5'- (4-F-phenyl) | 2'-Cl | CF₃ |
| 12a.48 | Me | 4'-Cl | 5'- (4-F-phenyl) | 2'-Cl | CF₃ |

TABLE 13a compounds of formula IAm:

(IAm)

| Compound Number | R₁ | R₃ | R₄ | R₅ | R₆ | R₇ | R₈ |
|---|---|---|---|---|---|---|---|
| 13a.1 | H | Cl | 5'- ethynyl-cyclopropyl | 6'-H | Me | Me | F |
| 13a.2 | Me | Cl | 5'- ethynyl-cyclopropyl | 6'-H | Me | Me | F |
| 13a.3 | H | Cl | 6'- ethynyl-cyclopropyl | 5'-H | Me | Me | F |
| 13a.4 | Me | Cl | 6'- ethynyl-cyclopropyl | 5'-H | Me | Me | F |
| 13a.5 | H | Cl | 5'- ethynyl-cyclopentyl | 6'-H | Me | Me | F |
| 13a.6 | Me | Cl | 5'- ethynyl-cyclopentyl | 6'-H | Me | Me | F |
| 13a.7 | H | Cl | 6'- ethynyl-cyclopentyl | 5'-H | Me | Me | F |
| 13a.8 | Me | Cl | 6'- ethynyl-cyclopentyl | 5'-H | Me | Me | F |
| 13a.9 | H | Cl | 5'- ethynyl-cyclohexyl | 6'-H | Me | Me | F |
| 13a.10 | Me | Cl | 5'- ethynyl-cyclohexyl | 6'-H | Me | Me | F |
| 13a.11 | H | Cl | 6'- ethynyl-cyclohexyl | 5'-H | Me | Me | F |
| 13a.12 | Me | Cl | 6'- ethynyl-cyclohexyl | 5'-H | Me | Me | F |

TABLE 13a-continued compounds of formula IAm:

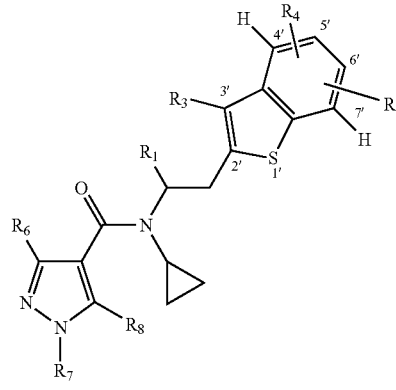

(IAm)

| Compound Number | R₁ | R₃ | R₄ | R₅ | R₆ | R₇ | R₈ |
|---|---|---|---|---|---|---|---|
| 13a.13 | H | Cl | 5'- 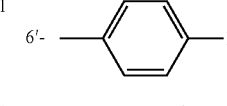 | 6'-H | Me | Me | F |
| 13a.14 | Me | Cl | 5'- 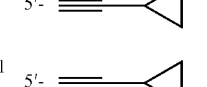 | 6'-H | Me | Me | F |
| 13a.15 | H | Cl | 6'- 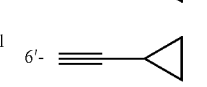 | 5'-H | Me | Me | F |
| 13a.16 | Me | Cl | 6'- 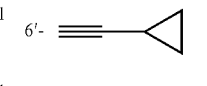 | 5'-H | Me | Me | F |
| 13a.17 | H | Cl | 5'- 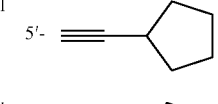 | 6'-H | Me | Me | F |
| 13a.18 | Me | Cl | 5'- 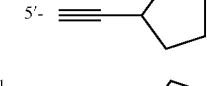 | 6'-H | Me | Me | F |
| 13a.19 | H | Cl | 6'- 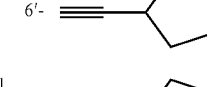 | 5'-H | Me | Me | F |
| 13a.20 | Me | Cl | 6'-  | 5'-H | Me | Me | F |
| 13a.21 | H | Cl | 5'- 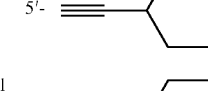 | 6'-H | Me | Me | F |
| 13a.22 | Me | Cl | 5'-  | 6'-H | Me | Me | F |
| 13a.23 | H | Cl | 6'- 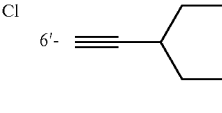 | 5'-H | Me | Me | F |
| 13a.24 | Me | Cl | 6'-  | 5'-H | Me | Me | F |
| 13a.25 | H | Cl | 5'-≡-cyclopropyl | 6'-H | CF₂H | Me | H |
| 13a.26 | Me | Cl | 5'-≡-cyclopropyl | 6'-H | CF₂H | Me | H |
| 13a.27 | H | Cl | 6'-≡-cyclopropyl | 5'-H | CF₂H | Me | H |
| 13a.28 | Me | Cl | 6'-≡-cyclopropyl | 5'-H | CF₂H | Me | H |
| 13a.29 | H | Cl | 5'-≡-cyclopentyl | 6'-H | CF₂H | Me | H |
| 13a.30 | Me | Cl | 5'-≡-cyclopentyl | 6'-H | CF₂H | Me | H |
| 13a.31 | H | Cl | 6'-≡-cyclopentyl | 5'-H | CF₂H | Me | H |
| 13a.32 | Me | Cl | 6'-≡-cyclopentyl | 5'-H | CF₂H | Me | H |
| 13a.33 | H | Cl | 5'-≡-cyclohexyl | 6'-H | CF₂H | Me | H |
| 13a.34 | Me | Cl | 5'-≡-cyclohexyl | 6'-H | CF₂H | Me | H |
| 13a.35 | H | Cl | 6'-≡-cyclohexyl | 5'-H | CF₂H | Me | H |

TABLE 13a-continued compounds of formula IAm:

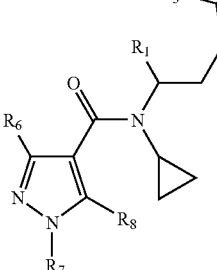

(IAm)

| Compound Number | R$_1$ | R$_3$ | R$_4$ | R$_5$ | R$_6$ | R$_7$ | R$_8$ |
|---|---|---|---|---|---|---|---|
| 13a.36 | Me | Cl | 6'- ≡— cyclohexyl | 5'-H | CF$_2$H | Me | H |
| 13a.37 | H  | Cl | 5'- ≡— phenyl | 6'-H | CF$_2$H | Me | H |
| 13a.38 | Me | Cl | 5'- ≡— phenyl | 6'-H | CF$_2$H | Me | H |
| 13a.39 | H  | Cl | 6'- ≡— phenyl | 5'-H | CF$_2$H | Me | H |
| 13a.40 | Me | Cl | 6'- ≡— phenyl | 5'-H | CF$_2$H | Me | H |
| 13a.41 | H  | Cl | 5'- 4-Cl-phenyl | 6'-H | CF$_2$H | Me | H |
| 13a.42 | Me | Cl | 5'- 4-Cl-phenyl | 6'-H | CF$_2$H | Me | H |
| 13a.43 | H  | Cl | 6'- 4-Cl-phenyl | 5'-H | CF$_2$H | Me | H |
| 13a.44 | Me | Cl | 6'- 4-Cl-phenyl | 5'-H | CF$_2$H | Me | H |
| 13a.45 | H  | Cl | 5'- 4-F-phenyl | 6'-H | CF$_2$H | Me | H |
| 13a.46 | Me | Cl | 5'- 4-F-phenyl | 6'-H | CF$_2$H | Me | H |
| 13a.47 | H  | Cl | 6'- 4-F-phenyl | 5'-H | CF$_2$H | Me | H |
| 13a.48 | Me | Cl | 6'- 4-F-phenyl | 5'-H | CF$_2$H | Me | H |
| 13a.49 | H  | Cl | 5'- ≡— cyclopropyl | 6'-H | CF$_3$ | Me | H |
| 13a.50 | Me | Cl | 5'- ≡— cyclopropyl | 6'-H | CF$_3$ | Me | H |
| 13a.51 | H  | Cl | 6'- ≡— cyclopropyl | 5'-H | CF$_3$ | Me | H |
| 13a.52 | Me | Cl | 6'- ≡— cyclopropyl | 5'-H | CF$_3$ | Me | H |
| 13a.53 | H  | Cl | 5'- ≡— cyclopentyl | 6'-H | CF$_3$ | Me | H |
| 13a.54 | Me | Cl | 5'- ≡— cyclopentyl | 6'-H | CF$_3$ | Me | H |
| 13a.55 | H  | Cl | 6'- ≡— cyclopentyl | 5'-H | CF$_3$ | Me | H |
| 13a.56 | Me | Cl | 6'- ≡— cyclopentyl | 5'-H | CF$_3$ | Me | H |
| 13a.57 | H  | Cl | 5'- ≡— cyclohexyl | 6'-H | CF$_3$ | Me | H |
| 13a.58 | Me | Cl | 5'- ≡— cyclohexyl | 6'-H | CF$_3$ | Me | H |

TABLE 13a-continued compounds of formula IAm:

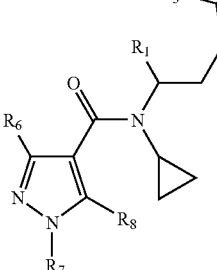

(IAm)

| Compound Number | R₁ | R₃ | R₄ | R₅ | R₆ | R₇ | R₈ |
|---|---|---|---|---|---|---|---|
| 13a.59 | H | Cl | 6'- ethynyl-cyclohexyl | 5'-H | CF₃ | Me | H |
| 13a.60 | Me | Cl | 6'- ethynyl-cyclohexyl | 5'-H | CF₃ | Me | H |
| 13a.61 | H | Cl | 5'- ethynyl-phenyl | 6'-H | CF₃ | Me | H |
| 13a.62 | Me | Cl | 5'- ethynyl-phenyl | 6'-H | CF₃ | Me | H |
| 13a.63 | H | Cl | 6'- ethynyl-phenyl | 5'-H | CF₃ | Me | H |
| 13a.64 | Me | Cl | 6'- ethynyl-phenyl | 5'-H | CF₃ | Me | H |
| 13a.65 | H | Cl | 5'- 4-chlorophenyl | 6'-H | CF₃ | Me | H |
| 13a.66 | Me | Cl | 5'- 4-chlorophenyl | 6'-H | CF₃ | Me | H |
| 13a.67 | H | Cl | 6'- 4-chlorophenyl | 5'-H | CF₃ | Me | H |
| 13a.68 | Me | Cl | 6'- 4-chlorophenyl | 5'-H | CF₃ | Me | H |
| 13a.69 | H | Cl | 5'- 4-fluorophenyl | 6'-H | CF₃ | Me | H |
| 13a.70 | Me | Cl | 5'- 4-fluorophenyl | 6'-H | CF₃ | Me | H |
| 13a.71 | H | Cl | 6'- 4-fluorophenyl | 5'-H | CF₃ | Me | H |
| 13a.72 | Me | Cl | 6'- 4-fluorophenyl | 5'-H | CF₃ | Me | H |

TABLE 14a compound of formula IAn (IAn)

| Compound Number | R₁ | R₃ | R₄ | R₅ | R₆ |
|---|---|---|---|---|---|
| 14a.1 | H | Cl | 5'- ethynyl-cyclopropyl | 6'-H | CF₃ |
| 14a.2 | Me | Cl | 6'- ethynyl-cyclopropyl | 5'-H | CF₃ |
| 14a.3 | H | Cl | 5'- ethynyl-cyclopentyl | 6'-H | CF₃ |

TABLE 14a-continued compound of formula IAn

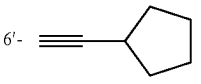

(IAn)

| Compound Number | R₁ | R₃ | R₄ | R₅ | R₆ |
|---|---|---|---|---|---|
| 14a.4 | Me | Cl | 6'- ≡ cyclopentyl | 5'-H | CF₃ |
| 14a.5 | H | Cl | 5'- ≡ cyclohexyl | 6'-H | CF₃ |
| 14a.6 | Me | Cl | 6'- ≡ cyclohexyl | 5'-H | CF₃ |
| 14a.7 | H | Cl | 5'- ≡ phenyl | 6'-H | CF₃ |
| 14a.8 | Me | Cl | 6'- ≡ phenyl | 5'-H | CF₃ |
| 14a.9 | H | Cl | 5'- —C₆H₄—Cl | 6'-H | CF₃ |
| 14a.10 | Me | Cl | 6'- —C₆H₄—Cl | 5'-H | CF₃ |
| 14a.11 | H | Cl | 5'- —C₆H₄—F | 6'-H | CF₃ |
| 14a.12 | Me | Cl | 6'- —C₆H₄—F | 5'-H | CF₃ |

Tables 15a-17a: Compounds of Formula IIaaa

The invention is further illustrated by the preferred individual compounds of formula (IIaaa) listed below in Tables 15-17a. Characterising data is given in Table 21a.

TABLE 15

Compounds of formula (IIa)

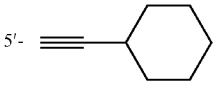

(IIaaa)

| Cpd No. | R₁ | R₃ | R₄ₐ | R₅ | A |
|---|---|---|---|---|---|
| Z1aa.1 | H | Cl | Br | H | 3-difluoromethyl-1-methyl-1H-pyrazol-4-yl |
| Z1aa.2 | Me | Cl | Br | H | 3-difluoromethyl-1-methyl-1H-pyrazol-4-yl |
| Z1aa.3 | H | Br | Br | H | 3-difluoromethyl-1-methyl-1H-pyrazol-4-yl |
| Z1aa.4 | Me | Br | Br | H | 3-difluoromethyl-1-methyl-1H-pyrazol-4-yl |
| Z1aa.5 | H | Cl | Br | H | 3-trifluoromethyl-1-methyl-1H-pyrazol-4-yl |
| Z1aa.6 | Me | Cl | Br | H | 3-trifluoromethyl-1-methyl-1H-pyrazol-4-yl |
| Z1aa.7 | H | Br | Br | H | 3-trifluoromethyl-1-methyl-1H-pyrazol-4-yl |
| Z1aa.8 | Me | Br | Br | H | 3-trifluoromethyl-1-methyl-1H-pyrazol-4-yl |
| Z1aa.9 | H | Cl | Br | H | 3-difluoromethyl-1-methyl-pyrrol-4-yl |
| Z1aa.10 | Me | Cl | Br | H | 3-difluoromethyl-1-methyl-pyrrol-4-yl |
| Z1aa.11 | H | Cl | Br | H | 3-difluoromethyl-1-methyl-1H-triazol-4-yl |
| Z1aa.12 | Me | Cl | Br | H | 3-difluoromethyl-1-methyl-1H-triazol-4-yl |
| Z1aa.13 | H | Cl | Br | H | 4-difluoromethyl-2-methyl-thiazol-5-yl |
| Z1aa.14 | Me | Cl | Br | H | 4-difluoromethyl-2-methyl-thiazol-5-yl |
| Z1aa.15 | H | Cl | Br | H | 2-chloro-pyridyl-3-yl |
| Z1aa.16 | Me | Cl | Br | H | 2-chloro-pyridyl-3-yl |
| Z1aa.17 | H | Cl | Br | H | 2-difluoromethyl-phenyl |
| Z1aa.18 | Me | Cl | Br | H | 2-difluoromethyl-phenyl |
| Z1aa.19 | H | Cl | Br | H | 2-trifluoromethyl-phenyl |
| Z1aa.20 | Me | Cl | Br | H | 2-trifluoromethyl-phenyl |

TABLE 16a

Compounds of formula IIab

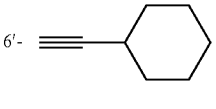

(IIab)

| Cpd No. | R₁ | R₃ | R₄ₐ | R₅ | A |
|---|---|---|---|---|---|
| Z1aa.21 | H | 4'-Cl | 5'-Br | 2'-Cl | 3-difluoromethyl-1-methyl-1H-pyrazol-4-yl |
| Z1aa.22 | Me | 4'-Cl | 5'-Br | 2'-Cl | 3-difluoromethyl-1-methyl-1H-pyrazol-4-yl |
| Z1aa.23 | H | 4'-Cl | 2'-Br | 5'-Cl | 3-difluoromethyl-1-methyl-1H-pyrazol-4-yl |

TABLE 16a-continued

Compounds of formula IIab

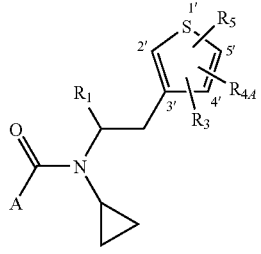

(IIab)

| Cpd No. | R₁ | R₃ | R₄ₐ | R₅ | A |
|---|---|---|---|---|---|
| Z1aa.24 | Me | 4'-Cl | 2'-Br | 5'-Cl | 3-difluoromethyl-1-methyl-1H-pyrazol-4-yl |

TABLE 17a

Compounds of formula IIac:

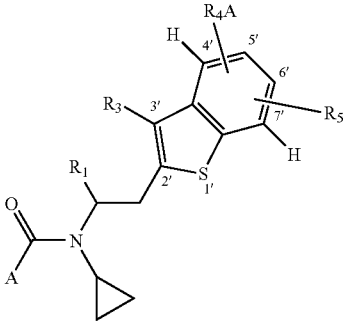

(IIac)

| Cpd No. | R₁ | R₃ | R₄ₐ | R₅ | A |
|---|---|---|---|---|---|
| Z1aa.25 | H | Cl | 5'-Br | 6'-H | 3-difluoromethyl-1-methyl-1H-pyrazol-4-yl |
| Z1aa.26 | Me | Cl | 5-Br | 6'-H | 3-difluoromethyl-1-methyl-1H-pyrazol-4-yl |
| Z1aa.27 | H | Cl | 6'-Br | 5'-H | 3-difluoromethyl-1-methyl-1H-pyrazol-4-yl |
| Z1aa.28 | Me | Cl | 6'-Br | 5'-H | 3-difluoromethyl-1-methyl-1H-pyrazol-4-yl |

Tables 18a-20a: Compounds of formula III

The invention is further illustrated by the preferred individual compounds of formula (III) listed below in Tables 18-20. Characterising data is given in Table 21a.

TABLE 18a

Compounds of formula (IIIaa)

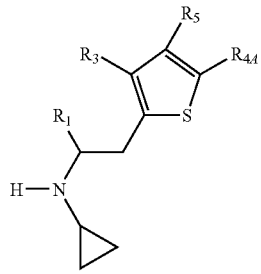

(IIIaa)

| Cpd No. | R₁ | R₃ | R₄ₐ | R₅ |
|---|---|---|---|---|
| Z2aa.1 | H | Cl | Br | H |
| Z2aa.2 | Me | Cl | Br | H |
| Z2aa.3 | H | Br | Br | H |
| Z2aa.4 | Me | Br | Br | H |

TABLE 19a

Compounds of formula IIIab

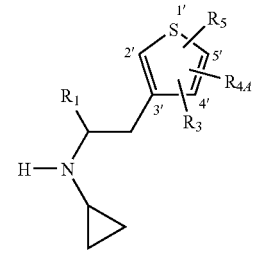

(IIIab)

| Cpd No. | R₁ | R₃ | R₄ₐ | R₅ |
|---|---|---|---|---|
| Z2aa.5 | H | 4'-Cl | 5'-Br | 2'-Cl |
| Z2aa.6 | Me | 4'-Cl | 5'-Br | 2'-Cl |
| Z2aa.7 | H | 4'-Cl | 2'-Br | 5'-Cl |
| Z2aa.8 | Me | 4'-Cl | 2'-Br | 5'-Cl |

TABLE 20a

Compounds of formula IIIac:

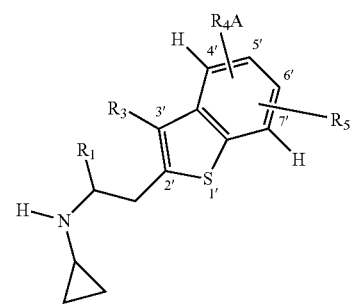

(IIIac)

| Cpd No. | R₁ | R₃ | R₄ₐ | R₅ |
|---|---|---|---|---|
| Z2aa.9 | H | Cl | 5'-Br | 6'-H |
| Z2aa.10 | Me | Cl | 5-Br | 6'-H |
| Z2aa.11 | H | Cl | 6'-Br | 5'-H |
| Z2aa.12 | Me | Cl | 6'-Br | 5'-H |

Formulation Examples for Compounds of Formula I

Example F-1.1 to F-1.2

Emulsifiable Concentrates

| Components | F-1.1 | F-1.2 |
|---|---|---|
| compound of Tables 1 to 14a | 25% | 50% |
| calcium dodecylbenzenesulfonate | 5% | 6% |
| castor oil polyethylene glycol ether (36 mol ethylenoxy units) | 5% | — |
| tributylphenolpolyethylene glycol ether (30 mol ethylenoxy units) | — | 4% |
| cyclohexanone | — | 20% |
| xylene mixture | 65% | 20% |

Emulsions of any desired concentration can be prepared by diluting such concentrates with water.

Example F-2

Emulsifiable Concentrate

| Components | F-2 |
|---|---|
| compound of Tables 1 to 14a | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Tables 1 to 14a | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Tables 1 to 14a | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Tables 1 to 14a | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Tables 1 to 14a | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Tables 1 to 14a | 40% |
| propylene glycol | 5% |
| copolymer butanol PO/EO | 2% |

| | |
|---|---|
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

Fungicidal Actions

Example B-1

Action against *Botrytis cinerea*/tomato (*Botrytis* on tomatoes)

4 week old tomato plants cv. Roter Gnom are treated with the formulated test compound (0.02% active ingredient) in a spray chamber. Two days after application tomato plants are inoculated by spraying a spore suspension ($1 \times 10^5$ conidia/ml) on the test plants. After an incubation period of 4 days at 20° C. and 95% r.h. in a growth chamber the disease incidence is assessed. Compounds 1.38, 7.27 and 7.38 show good activity in this test (<20% infestation).

Example B-2

Action Against *Uncinula necator*/Grape (Powdery Mildew on Grape)

5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% r.h. under a light regime of 14/10 hours (light/dark) the disease incidence is assessed. Compounds 1.38, 6.14, 7.27, 7.38, 12.6 and 12.30 show good activity in this test (<20% infestation).

Example B-3

Action Against *Puccinia recondita*/Wheat (Brownrust on Wheat)

1 week old wheat plants cv. Arina are treated with the formulated test compound (0.02% active ingredient) in a spray chamber. One day after application, the wheat plants are inoculated by spraying a spore suspension ($1 \times 10^5$ uredospores/ml) on the test plants. After an incubation period of 2 days at 20° C. and 95% r.h. the plants are kept in a greenhouse for 8 days at 20° C. and 60% r.h. The disease incidence is assessed 10 days after inoculation.

Compounds 1.38, 6.14 and 7.38 show good activity in this test (<20% infestation).

Example B-4

Action Against *Septoria tritici*/Wheat (Septoria Leaf Spot on Wheat)

2 week old wheat plants cv. Riband are treated with the formulated test compound (0.02% active ingredient) in a spray chamber. One day after application, wheat plants are inoculated by spraying a spore suspension ($10 \times 10^5$ conidia/ml) on the test plants. After an incubation period of 1 day at 23° C. and 95% r.h., the plants are kept for 16 days at 23° C. and 60% r.h. in a greenhouse. The disease incidence is assessed 18 days after inoculation. Compounds 1.38, 6.14 and 7.38 show good activity in this test (<20% infestation).

Example B-5

Action Against *Pyrenophora teres*/Barley (Net Blotch on Barley)

1 week old barley plants cv. Express are treated with the formulated test compound (0.02% active ingredient) in a spray chamber. Two days after application barley plants are inoculated by spraying a spore suspension ($3 \times 10^4$ conidia/ml) on the test plants. After an incubation period of 2 days at 20° C. and 95% r.h. plants are kept for 2 days at 20° C. and 60% r.h. in a greenhouse. The disease incidence is assessed 4 days after inoculation. Compounds 1.38, 6.14, 7.27, 7.38, 12.6 and 12.30 show good activity in this test (<20% infestation).

Example B-6

Action Against *Alternaria solani*/Tomato (Early Blight on Tomatoes)

4 week old tomato plants cv. Roter Gnom are treated with the formulated test compound (0.02% active ingredient) in a spray chamber. Two days after application, the tomato plants are inoculated by spraying a spore suspension ($2 \times 10^5$ conidia/ml) on the test plants. After an incubation period of 3 days at 20° C. and 95% r.h. in a growth chamber the disease incidence is assessed. Compounds 1.38, 7.27, 7.38, 12.6 and 12.30 show good activity in this test (<20% infestation).

What is claimed is:

1. A compound of the formula I

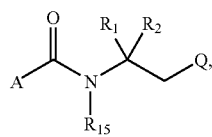

wherein
A is $A_1$

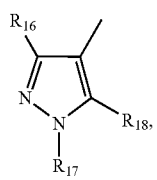

in which
$R_{16}$ is halogen, cyano, nitro, $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl;
$R_{17}$ is $C_1$-$C_4$alkyl, $C_1$-$C_4$halogenalkyl, $C_1$-$C_4$halogenalkoxy, $C_1$-$C_4$alkoxy-$C_1$-$C_4$alkyl or $C_1$-$C_4$halogenalkoxy-$C_1$-$C_4$alkyl; and
$R_{18}$ is hydrogen, halogen or cyano;
$R_1$ and $R_2$ independently of each other stand for hydrogen, halogen, $C_1$-$C_4$ alkyl or $C_1$-$C_4$ halogenalkyl;
Q is $Q_1$

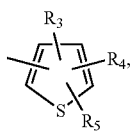

wherein
$R_3$ is halogen or $C_1$-$C_4$ halogenalkyl;
$R_4$ is $C_3$-$C_7$ cycloalkyl acetynyl, phenyl acetynyl, halogenphenyl acetynyl or halogenphenyl;
$R_5$ is hydrogen, halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl;
$R_{15}$ is hydrogen or $C_3$-$C_7$cycloalkyl;
and tautomers/isomers/enantiomers of the compound.

2. A compound of formula I according to claim 1, wherein $R_{15}$ is hydrogen.

3. A compound of formula I according to claim 1, wherein $R_{16}$ is $C_1$-$C_4$alkyl or $C_1$-$C_4$halogenalkyl; $R_{17}$ is $C_1$-$C_4$alkyl; and $R_{18}$ is hydrogen or halogen.

4. A compound of formula I according to claim 1, wherein $R_4$ is $C_3$-$C_7$ cycloalkyl acetynyl, phenyl acetynyl or halogenphenyl acetynyl.

5. A compound of formula I according to claim 1, wherein Q is $Q_{1A\text{-}1}$

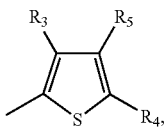

wherein
$R_3$ is halogen or $C_1$-$C_4$ halogenalkyl; $R_4$ is $C_3$-$C_7$ cycloalkyl acetynyl, phenyl acetynyl, halogenphenyl acetynyl or halogenphenyl; and $R_5$ is hydrogen, halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl.

6. A compound of formula I according to claim 1, wherein Q is $Q_{1B\text{-}1}$

wherein $R_3$ is halogen or $C_1$-$C_4$ halogenalkyl; $R_4$ is $C_3$-$C_7$ cycloalkyl acetynyl, phenyl acetynyl, halogenphenyl acetynyl or halogenphenyl; and $R_5$ is hydrogen, halogen, $C_1$-$C_4$ alkyl, $C_1$-$C_4$ halogenalkyl, phenyl, halogenphenyl, $C_3$-$C_7$ cycloalkyl acetynyl, phenyl acetynyl or halogenphenyl acetynyl.

7. A method of controlling infestation of useful plants by phytopathogenic microorganisms, the method comprising:
applying an effective amount of a compound of formula I according to claim 1 or a composition, comprising this compound as active ingredient, to the plants, to parts thereof or the locus thereof.

8. A composition for controlling and protecting against phytopathogenic microorganisms, comprising a compound of formula I according to claim 1 and an inert carrier.

9. The method of claim 7, wherein the phytopathogenic microorganisms include at least one member selected from the group consisting of a Fungi imperfecti class, a Basidiomycetes class, an Ascomycetes class, and an Oomycetes class.

10. The method of claim 7, wherein the phytopathogenic microorganisms include at least one member selected from the group consisting of a *Botrytis* species, a *Uncinula* species, a *Puccinia* species, a *Septoria* species, a *Pyrenophora* species, and an *Alternaria* species.

11. The method of claim 10, wherein
at least one of the *Botrytis* species is *Botrytis cinerea*,
at least one of the *Uncinula* species is *Uncinula necator*,
at least one of the *Puccinia* species is *Puccinia recondita*,
at least one of the *Septoria* species is *Septoria tritici*,
at least one of the *Pyrenophora* species is *Pyrenophora teres*, and
at least one of the *Alternaria* species is *Alternaria solani*.

* * * * *